US008288388B2

(12) United States Patent
Beswick et al.

(10) Patent No.: US 8,288,388 B2
(45) Date of Patent: Oct. 16, 2012

(54) 3-PYRIDYLCARBONYL-PIPERAZINYL ULFONYL DERIVATIVES

(75) Inventors: Paul John Beswick, Harlow (GB); Alister Campbell, Harlow (GB); Andrew Cridland, Harlow (GB); Robert James Gleave, Harlow (GB); Jag Paul Heer, Harlow (GB); Neville Hubert Nicholson, Harlow (GB); Lee William Page, Harlow (GB); Sadie Vile, Harlow (GB)

(73) Assignee: Convergence Pharmaceuticals Limited, London (GB)

( * ) Notice: Subject to any disclaimer, the term of this patent is extended or adjusted under 35 U.S.C. 154(b) by 244 days.

(21) Appl. No.: 12/503,125

(22) Filed: Jul. 15, 2009

(65) Prior Publication Data
US 2010/0022555 A1    Jan. 28, 2010

(30) Foreign Application Priority Data
Jul. 17, 2008    (GB) .................................. 0813142.7

(51) Int. Cl.
A61K 31/496    (2006.01)
C07D 401/06    (2006.01)
(52) U.S. Cl. .................................. 514/253.13; 544/365
(58) Field of Classification Search .......................... None
See application file for complete search history.

(56) References Cited

U.S. PATENT DOCUMENTS

| 5,112,824 | A | 5/1992 | Baldwin et al. |
| 5,880,128 | A | 3/1999 | Doll et al. |
| 7,759,339 | B2 | 7/2010 | Aertgeerts et al. |
| 2002/0115854 | A1 | 8/2002 | Lam et al. |
| 2005/0153981 | A1 | 7/2005 | Li et al. |
| 2007/0142394 | A1 | 6/2007 | Solomon et al. |
| 2008/0188484 | A1 | 8/2008 | Nettekoven et al. |
| 2008/0188487 | A1 | 8/2008 | Nettekoven et al. |

FOREIGN PATENT DOCUMENTS

| DE | 102004054053 A1 | 5/2006 |
| EP | 1314733 A1 | 11/2001 |
| EP | 2065369 | 6/2009 |
| WO | 9504062 A1 | 2/1995 |
| WO | 9630343 A1 | 10/1996 |
| WO | 9631501 A1 | 10/1996 |
| WO | 9728139 A1 | 8/1997 |
| WO | WO 9817625 | 4/1998 |
| WO | 9821188 A1 | 5/1998 |
| WO | 9854164 A1 | 12/1998 |
| WO | 8806371 A1 | 2/1999 |
| WO | 9937304 A1 | 7/1999 |
| WO | 0012074 A3 | 3/2000 |
| WO | 0042011 A1 | 7/2000 |
| WO | 0164676 A3 | 9/2001 |
| WO | 0166534 A2 | 9/2001 |
| WO | 0176693 A1 | 10/2001 |
| WO | 0209686 A2 | 2/2002 |
| WO | 0232874 A2 | 4/2002 |
| WO | 02088115 A1 | 11/2002 |
| WO | 03048139 A1 | 6/2003 |
| WO | 03062212 A1 | 7/2003 |
| WO | 03076422 A1 | 9/2003 |
| WO | 03087086 A3 | 10/2003 |
| WO | 03088967 A1 | 10/2003 |
| WO | 2005044797 A1 | 5/2005 |
| WO | 2005089502 A2 | 9/2005 |
| WO | 2005095362 A1 | 10/2005 |
| WO | 2005113542 A3 | 12/2005 |
| WO | 2006034341 A3 | 3/2006 |
| WO | 2006040181 A2 | 4/2006 |
| WO | 2006048209 A1 | 5/2006 |
| WO | 2006105127 A2 | 10/2006 |
| WO | 2006129199 A1 | 12/2006 |
| WO | 2007070760 A3 | 6/2007 |
| WO | 2007075524 A2 | 7/2007 |
| WO | 2007087068 A3 | 8/2007 |
| WO | 2007103456 A2 | 9/2007 |
| WO | 2007110449 A1 | 10/2007 |
| WO | 2007111921 A1 | 10/2007 |
| WO | 2007118853 A1 | 10/2007 |
| WO | 2007118854 A1 | 10/2007 |
| WO | 2008008398 A2 | 1/2008 |
| WO | 2008024284 A3 | 2/2008 |
| WO | 2008048914 A1 | 4/2008 |
| WO | 2008075019 A1 | 6/2008 |
| WO | 2008124118 A1 | 10/2008 |
| WO | 2008150447 A1 | 12/2008 |
| WO | 2008150470 A1 | 12/2008 |
| WO | 2009040659 A2 | 4/2009 |
| WO | 2009045382 A1 | 4/2009 |
| WO | 9906371 A1 | 8/2010 |
| ZA | 9710062 | 5/1998 |

OTHER PUBLICATIONS

CA Registry No. 1100114-27-9, entered into the Registry File on Feb. 3, 2009, supplied by UkroOrgSynthesis.*
CA Registry No. 1011033-34-3, entered into the Registry File on Mar. 31, 2008, supplied by Ambinter.*
CA Registry No. 1009920-66-4, entered into the Registry File on Mar. 25, 2008, supplied by Ambinter.*
CA Registry No. 930672-18-7, entered into the Registry File on Apr. 18, 2007, supplied by Enamine.*
CA Registry No. 1097172-57-0, entered into the Registry File on Jan. 28, 2009, supplied by UkroOrgSynthesis.* CA Registry No. 1095946-34-1, entered into the Registry File on Jan. 26, 2009, supplied by UkroOrgSynthesis.*
CA Registry No. 1012451-76-1, entered into the Registry File on Apr. 6, 2008, supplied by Ambinter.*
CA Registry No. 1012502-58-7, entered into the Registry File on Apr. 6, 2008, supplied by Ambinter.*
CA Registry No. 940735-57-9, entered into the Registry File on Jul. 2, 2007, supplied by Enamine.*
CA Registry No. 950047-33-3, entered into the Registry File on Oct. 10, 2007, supplied by Enamine.*
Registry File Document of CHEMCATS answers for U.S. Appl. No. 12/503,125, downloaded on Jun. 2012.*

(Continued)

*Primary Examiner* — Emily Bernhardt
(74) *Attorney, Agent, or Firm* — Womble Carlyle Sandridge & Rice, LLP

(57) ABSTRACT

The present invention relates to novel piperazine derivatives; to processes for their preparation; to pharmaceutical compositions containing the derivatives; and to the use of the derivatives in therapy to treat diseases for which blocking the $Ca_v2.2$ calcium channels is beneficial.

27 Claims, No Drawings

OTHER PUBLICATIONS

CA Registry No. 924155-24-8, entered into the Registry File on Mar. 1, 2007, supplied by Aurora Fine Chemicals.*

CA Registry No. 908501-86-0, entered into the Registry File on Sep. 26, 2006, supplied by Scientific Exchange Inc.*

CA Registry No. 849477-65-2, entered into the Registry File on Apr. 29, 2005, supplied by Enamine.*

CA Registry No. 849181-29-9, entered into the Registry File on Apr. 26, 2005, supplied by Enamine.*

CA Registry No. 746634-98-0, entered into the Registry File on Sep. 17, 2004, supplied by Enamine.*

Scapecchi et al., "Structure activity relationship studies on unifiram (DM232) and sunifiram (DM235), two novel and potent cognitiion enhancing drugs" Bioorganic and Medicinal Chemistry, Elservier Service Ltd GB, vol. 12, Jan. 1, 2004, pp. 71-85, xp002526662.

* cited by examiner

3-PYRIDYLCARBONYL-PIPERAZINYL ULFONYL DERIVATIVES

This application claims priority to GB Application No. 0813142.7 filed on Jul. 17, 2008 in the United Kingdom, the disclosure of which is incorporated herein by reference in its entirety.

The present invention relates to novel piperazine derivatives; to processes for their preparation; to pharmaceutical compositions containing the derivatives; and to the use of the derivatives in therapy to treat diseases for which blocking the $Ca_v2.2$ calcium channels is beneficial.

Pre-synaptic $Ca_v2.2$ (N-type) voltage-gated calcium channels in the dorsal horn of the spinal cord modulate the release of key pro-nociceptive neurotransmitters such as glutamate, substance P (SP) and calcitonin-gene-related peptide (CGRP), indicating the potential therapeutic use of $Ca_v2.2$ calcium channel blockers as analgesics.

Peptidic ω-conotoxins, isolated from the venom of cone snails, have been shown to be selective for $Ca_v2.2$ calcium channels and can block SP release in the spinal cord (Smith et al. (2002) Pain, 96: 119-127). Moreover, they have been shown to be antinociceptive in animal models of chronic pain following intrathecal administration (Bowersox et al. (1996) Journal of Pharmacology and Experimental Therapeutics, 279: 1243-1249; Smith et al. (2002) supra), and have been shown to be effective analgesics in clinical use, particularly in the treatment of neuropathic pain (Brose et al. (1997) Clinical Journal of Pain, 13: 256-259).

In addition, $Ca_v2.2$ calcium channels have been shown to be important for normal neuronal function (Winquist et al. (2005) Biochemical Pharmacology, 70: 489-499). Therefore, the aim is to identify novel molecules that preferentially block $Ca_v2.2$ under conditions of increased neuronal excitability, so-called use-dependent blockers, as is the case in chronic pain syndromes.

WO 2007/111921 (Amgen Inc) describes a series of diazaheterocyclic amide derivatives which are claimed to be useful in the treatment of diabetes, obesity and related conditions and disorders. DE 10155684 (Bayer AG) describes a series of 2-[[(aminosulfonyl)phenyl]ureido]thiazoles as antibiotics. WO 2008/024284 (Merck & Co) describes a series of sulfonylated piperazines as cannabinoid-1 (CB1) receptor modulators which are claimed to be useful in the treatment for example of psychosis, cognitive disorders and Alzheimer's disease.

The present invention provides compounds which are capable of blocking these $Ca_v2.2$ calcium channels.

In a first aspect there is provided a compound of formula (I), or a pharmaceutically acceptable salt thereof, for use in therapy, wherein:

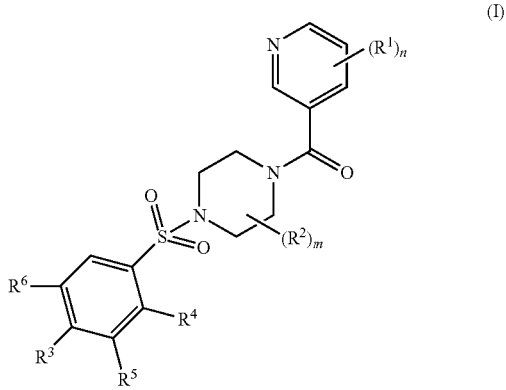

(I)

m and n are independently selected from 0, 1 and 2;

where present, each $R^1$ is independently selected from $C_{1-4}$ alkyl, $C_{1-4}$ alkoxy, $C_{3-6}$ cycloalkyl, cyano, $NR^{1a}R^{1b}$ and halogen;

$R^{1a}$ and $R^{1b}$ are independently selected from hydrogen, $C_{1-4}$ alkyl, $C_{3-6}$ cycloalkyl and a 4 to 6 membered heterocyclyl; or $R^{1a}$ and $R^{1b}$ together with the nitrogen atom to which they are attached form a 4 to 6 membered heterocyclic ring;

where present, each $R^2$ is $C_{1-4}$ alkyl;

$R^3$ is hydrogen, halogen, cyano, $C_{1-4}$ haloalkyl or $C_{1-4}$ haloalkoxy;

$R^4$ is hydrogen or $C_{1-4}$ alkyl;

$R^5$ is hydrogen, halogen, cyano, $C_{1-4}$ haloalkyl or $C_{1-4}$ haloalkoxy;

$R^6$ is hydrogen, halogen, cyano, $C_{1-4}$ haloalkyl or $C_{1-4}$ haloalkoxy;

such that at least 1 of $R^3$, $R^4$, $R^5$ and $R^6$ is a group other than hydrogen.

In a second aspect there is provided a compound of formula (I), or a salt thereof, wherein m and n are independently selected from 0, 1 and 2;

where present, each $R^1$ is independently selected from $C_{1-4}$ alkyl, $C_{1-4}$ alkoxy, $C_{3-6}$ cycloalkyl, cyano, $NR^{1a}R^{1b}$ and halogen;

$R^{1a}$ and $R^{1b}$ are independently selected from hydrogen, $C_{1-4}$ alkyl, $C_{3-6}$ cycloalkyl and a 4 to 6 membered heterocyclyl; or $R^{1a}$ and $R^{1a}$ together with the nitrogen atom to which they are attached form a 4 to 6 membered heterocyclic ring;

where present, each $R^2$ is $C_{1-4}$ alkyl;

$R^3$ is hydrogen, halogen, cyano, $C_{1-4}$ haloalkyl or $C_{1-4}$ haloalkoxy;

$R^4$ is hydrogen or $C_{1-4}$ alkyl;

$R^5$ is hydrogen, halogen, cyano, $C_{1-4}$ haloalkyl or $C_{1-4}$ haloalkoxy;

$R^6$ is hydrogen, halogen, cyano, $C_{1-4}$ haloalkyl or $C_{1-4}$ haloalkoxy;

such that at least 1 of $R^3$, $R^4$, $R^5$ and $R^6$ is a group other than hydrogen;

with the proviso that the compound is not

1-[(4-chlorophenyl)sulfonyl]-4-[(6-methyl-3-pyridinyl)carbonyl]piperazine;

1-[(5-bromo-3-pyridinyl)carbonyl]-4-[(4-chlorophenyl)sulfonyl]piperazine;

1-[(3-chlorophenyl)sulfonyl]-4-(3-pyridinylcarbonyl)piperazine;

1-[(5,6-dichloro-3-pyridinyl)carbonyl]-4-{[4-(trifluoromethyl)phenyl]sulfonyl}piperazine;

1-[(6-chloro-3-pyridinyl)carbonyl]-4-{[4-chloro-3-(trifluoromethyl)phenyl]sulfonyl}piperazine;

1-[(5,6-dichloro-3-pyridinyl)carbonyl]-4-({4-[(trifluoromethyl)oxy]phenyl}sulfonyl)piperazine;

1-[(5-bromo-3-pyridinyl)carbonyl]-4-{[4-(trifluoromethyl)phenyl]sulfonyl}piperazine;

1-[(6-chloro-3-pyridinyl)carbonyl]-4-{[4-(trifluoromethyl)phenyl]sulfonyl}piperazine;

1-{[4-chloro-3-(trifluoromethyl)phenyl]sulfonyl}-4-(3-pyridinylcarbonyl)piperazine;

1-(3-pyridinylcarbonyl)-4-{[3-(trifluoromethyl)phenyl]sulfonyl}piperazine;

1-(3-pyridinylcarbonyl)-4-{[4-(trifluoromethyl)phenyl]sulfonyl}piperazine;

1-(3-pyridinylcarbonyl)-4-({4-[(trifluoromethyl)oxy]phenyl}sulfonyl)piperazine;

1-{[4-chloro-3-(trifluoromethyl)phenyl]sulfonyl}-4-[(6-methyl-3-pyridinyl)carbonyl]piperazine;

1-[(6-methyl-3-pyridinyl)carbonyl]-4-({4-[(trifluoromethyl)oxy]phenyl}sulfonyl)piperazine;

1-{[6-(methyloxy)-3-pyridinyl]carbonyl}-4-({4-[(trifluoromethyl)oxy]phenyl}sulfonyl)piperazine;
4-({4-[(6-methyl-3-pyridinyl)carbonyl]-1-piperazinyl}sulfonyl)benzonitrile;
1-{[4-chloro-3-(trifluoromethyl)phenyl]sulfonyl}-4-{[2-(ethyloxy)-3-pyridinyl]carbonyl}piperazine;
1-{[2-(ethyloxy)-3-pyridinyl]carbonyl}-4-{[4-(trifluoromethyl)phenyl]sulfonyl}piperazine;
1-{[2-(ethyloxy)-3-pyridinyl]carbonyl}-4-({4-[(trifluoromethyl)oxy]phenyl}sulfonyl)piperazine;
1-[(3-chlorophenyl)sulfonyl]-4-{[2-(1-pyrrolidinyl)-3-pyridinyl]carbonyl}piperazine;
4-[(4-{[2-(1-pyrrolidinyl)-3-pyridinyl]carbonyl}-1-piperazinyl)sulfonyl]benzonitrile;
1-{[2-(ethyloxy)-3-pyridinyl]carbonyl}-4-[(3-fluorophenyl)sulfonyl]piperazine;
1-[(3-chlorophenyl)sulfonyl]-4-{[2-(1-pyrrolidinyl)-3-pyridinyl]carbonyl}piperazine;
1-[(5,6-dichloro-3-pyridinyl)carbonyl]-4-[(4-fluorophenyl)sulfonyl]piperazine;
1-[(4-fluorophenyl)sulfonyl]-4-{[2-(1-pyrrolidinyl)-3-pyridinyl]carbonyl}piperazine;
1-[(3-fluorophenyl)sulfonyl]-4-{[2-(1-pyrrolidinyl)-3-pyridinyl]carbonyl}piperazine; and
1-[(5-bromo-3-pyridinyl)carbonyl]-4-[(4-chlorophenyl)sulfonyl]piperazine.

It is understood that in formula (I), when present, $R^1$ may be attached to any one of the four possible carbon atoms in the pyridyl ring.

As used herein, the term "alkyl" (when used as a group or as part of a group) refers to a straight or branched hydrocarbon chain containing the specified number of carbon atoms. For example, $C_{1-6}$ alkyl means a straight or branched hydrocarbon chain containing at least 1 and at most 6 carbon atoms. Examples of alkyl include, but are not limited to; methyl (Me), ethyl (Et), n-propyl, i-propyl, t-butyl, n-hexyl and i-hexyl.

As used herein, the term "alkoxy" (when used as a group or as part of a group) refers to an —O-alkyl group wherein alkyl is as defined hereinbefore.

The term 'halogen' is used herein to describe, unless otherwise stated, a group selected from fluoro (fluorine), chloro (chlorine), bromo (bromine) or iodo (iodine). In one embodiment, the term 'halogen' is used herein to describe, unless otherwise stated, a group selected from chloro (chlorine) or bromo (bromine).

The term $C_{1-4}$ haloalkyl as used herein refers to a $C_{1-4}$ alkyl group as defined herein substituted with one or more halogen groups, e.g. $CF_3$, $CF_2H$ or $CF_3CH_2$.

The term $C_{1-4}$ haloalkoxy as used herein refers to an $C_{1-4}$ alkoxy group as defined herein substituted with one or more halogen groups, e.g. —O—$CF_3$.

The term $C_{3-6}$ cycloalkyl as used herein refers to a saturated monocyclic hydrocarbon ring of 3 to 6 carbon atoms. Examples of such groups include cyclopropyl, cyclobutyl, cyclopentyl and cyclohexyl.

The term 4 to 6 membered heterocyclic ring and its monovalent radical refers to a 4 to 6 membered saturated monocyclic ring which contains 1 or 2 heteroatoms independently selected from oxygen, nitrogen and sulphur. Suitable examples of such groups include pyrrolidinyl, piperidinyl, piperazinyl, morpholinyl, thiomorpholinyl and azetidinyl.

In one embodiment of the first or second aspect, $R^1$ is selected from $C_{1-4}$ alkyl, $C_{1-4}$ alkoxy, cyano and $NR^{1a}R^{1b}$. In another embodiment of the first or second aspect, $R^1$ is selected from $C_{1-4}$ alkyl and $C_{1-4}$ alkoxy. In one particular embodiment of the first or second aspect, $R^1$ is selected from methyl and methoxy. In a more particular embodiment of the first or second aspect, $R^1$ is selected from 2-methyl, 6-methyl, 2-methoxy and 6-methoxy. In an even more particular embodiment of the first or second aspect, $R^1$ is 2-methyl.

In one embodiment of the first or second aspect, $R^1$ is $NR^{1a}R^{1b}$ and $R^{1a}$ and $R^{1b}$ are independently selected from hydrogen and $C_{1-4}$ alkyl, or $R^{1a}$ and $R^{1b}$ together with the nitrogen atom to which they are attached form a 4 to 6 membered heterocyclic ring. In another embodiment of the first or second aspect, $R^{1a}$ and $R^{1b}$ are $C_{1-4}$ alkyl, or $R^{1a}$ and $R^{1b}$ together with the nitrogen atom to which they are attached form a 4 or 5 membered heterocyclic ring. In one particular embodiment of the first or second aspect, $R^{1a}$ and $R^{1b}$ are $C_{1-4}$ alkyl, or $R^{1a}$ and $R^{1b}$ together with the nitrogen atom to which they are attached form a morpholinyl, pyrrolidinyl or azetidinyl ring. In a more particular embodiment of the first or second aspect, $R^{1a}$ and $R^{1b}$ are $C_{1-4}$ alkyl. In an even more particular embodiment of the first or second aspect, $R^{1a}$ and $R^{1b}$ are selected from methyl and ethyl. In an even more particular embodiment, $R^{1a}$ and $R^{1b}$ together with the nitrogen atom to which they are attached form a morpholinyl, pyrrolidinyl or azetidinyl ring.

In one embodiment of the first or second aspect, n is 0 or 1. In another embodiment of the first or second aspect, n is 1. In a further embodiment of the first or second aspect, n is 0.

In one embodiment of the first or second aspect, $R^2$ is methyl. In another embodiment of the first or second aspect, $R^2$ is methyl and m is 1. In a particular embodiment of the first or second aspect, the compound of formula (I) is a compound of formula (Ia)

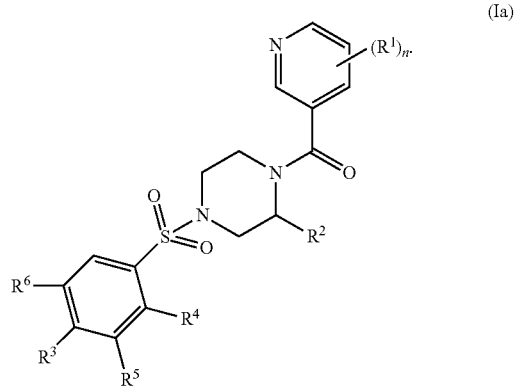

(Ia)

In a more particular embodiment of the first or second aspect, the compound of formula (I) is a compound of formula (Ib)

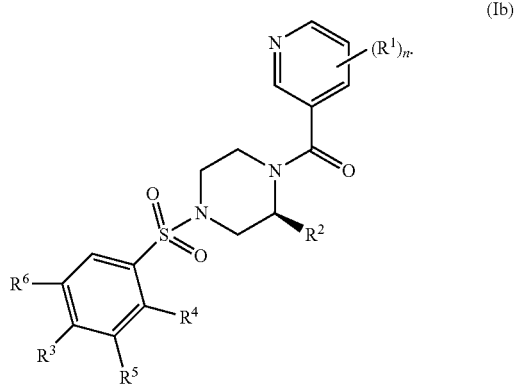

(Ib)

In one embodiment of the first or second aspect, $R^3$ is $C_{1-4}$ haloalkyl or $C_{1-4}$ haloalkoxy. In one particular embodiment of the first or second aspect, $R^3$ is trifluoromethyl, trifluoromethoxy or difluoromethoxy. In a more particular embodiment of the first or second aspect, $R^3$ is trifluoromethyl.

In one embodiment of the first or second aspect, $R^4$ is hydrogen or methyl. In one particular embodiment of the first or second aspect, $R^4$ is hydrogen.

In one embodiment of the first or second aspect, $R^5$ and $R^6$ are independently selected from hydrogen and $C_{1-4}$ haloalkyl. In one particular embodiment of the first or second aspect, $R^5$ and $R^6$ are independently selected from hydrogen and trifluoromethyl. In a more particular embodiment of the first or second aspect, $R^5$ and $R^6$ are hydrogen.

In one embodiment of the first or second aspect, $R^1$ is $C_{1-4}$ alkyl, $C_{1-4}$ alkoxy, cyano or $NR^{1a}R^{1b}$, particularly $R^1$ is $C_{1-4}$ alkyl or $C_{1-4}$ alkoxy, more particularly $R^1$ is methyl or methoxy, even more particularly $R^1$ is selected from 2-methyl, 6-methyl, 2-methoxy and 6-methoxy, yet even more particularly $R^1$ is 2-methyl; n is 0 or 1, particularly n is 1; $R^2$ is methyl, particularly $R^2$ is methyl and m is 1, more particularly 2-methyl relative to the piperazine carbonyl bond (as in formula (Ia)), even more particularly (2S)-2-methyl (as in formula (Ib)); $R^3$ is $C_{1-4}$ haloalkyl or $C_{1-4}$ haloalkoxy, particularly $R^3$ is trifluoromethyl, trifluoromethoxy or difluoromethoxy, more particularly $R^3$ is trifluoromethyl; $R^4$ is hydrogen or methyl, particularly $R^4$ is hydrogen; $R^5$ and $R^6$ are independently selected from hydrogen and $C_{1-4}$ haloalkyl, particularly $R^5$ and $R^6$ are independently selected from hydrogen and trifluoromethyl, more particularly $R^5$ and $R^6$ are hydrogen.

In one embodiment of the first or second aspect, $R^1$ is $C_{1-4}$ alkyl, $C_{1-4}$ alkoxy, cyano or $NR^{1a}R^{1b}$; n is 0 or 1; when present, $R^2$ is methyl; $R^3$ is $C_{1-4}$ haloalkyl or $C_{1-4}$ haloalkoxy; $R^4$ is hydrogen or methyl; $R^5$ and $R^6$ are independently selected from hydrogen and $C_{1-4}$ haloalkyl.

In one embodiment of the first or second aspect, $R^1$ is $C_{1-4}$ alkyl or $C_{1-4}$ alkoxy; n is 1; $R^2$ is methyl and m is 1; $R^3$ is trifluoromethyl, trifluoromethoxy or difluoromethoxy; $R^4$ is hydrogen; $R^5$ and $R^6$ are independently selected from hydrogen and trifluoromethyl.

In one embodiment of the first or second aspect, $R^1$ is methyl or methoxy; n is 1; $R^2$ is 2-methyl relative to the piperazine carbonyl bond (as in formula (Ia)) and m is 1; $R^3$ is trifluoromethyl, trifluoromethoxy or difluoromethoxy; $R^4$ is hydrogen; $R^5$ and $R^6$ are hydrogen.

In one embodiment of the first or second aspect, $R^1$ is selected from 2-methyl, 6-methyl, 2-methoxy and 6-methoxy; n is 1; $R^2$ is (2S)-2-methyl (as in formula (Ib)) and m is 1; $R^3$ is trifluoromethyl, trifluoromethoxy or difluoromethoxy; $R^4$ is hydrogen; $R^5$ and $R^6$ are hydrogen.

In one embodiment of the first or second aspect, $R^1$ is $NR^{1a}R^{1b}$ and $R^{1a}$ and $R^{1b}$ are independently hydrogen or $C_{1-4}$ alkyl, or $R^{1a}$ and $R^{1b}$ together with the nitrogen atom to which they are attached form a 4 to 6 membered heterocyclic ring, particularly $R^{1a}$ and $R^{1b}$ are independently $C_{1-4}$ alkyl, or $R^{1a}$ and $R^{1b}$ together with the nitrogen atom to which they are attached form a 4 or 5 membered heterocyclic ring, more particularly $R^{1a}$ and $R^{1b}$ are $C_{1-4}$ alkyl, or $R^{1a}$ and $R^{1b}$ together with the nitrogen atom to which they are attached form a morpholinyl, pyrrolidine or azetidinyl ring, even more particularly $R^{1a}$ and $R^{1b}$ are $C_{1-4}$ alkyl, yet even more particularly $R^{1a}$ and $R^{1b}$ are selected from methyl and ethyl; n is 0 or 1, particularly n is 1; $R^2$ is methyl, particularly $R^2$ is methyl and m is 1, more particularly 2-methyl relative to the piperazine carbonyl bond (as in formula (Ia)), even more particularly (2S)-2-methyl (as in formula (Ib)); $R^3$ is $C_{1-4}$ haloalkyl or $C_{1-4}$ haloalkoxy, particularly $R^3$ is trifluoromethyl, trifluoromethoxy or difluoromethoxy, more particularly $R^3$ is trifluoromethyl; $R^4$ is hydrogen or methyl, particularly $R^4$ is hydrogen; $R^5$ and $R^6$ are independently selected from hydrogen and $C_{1-4}$ haloalkyl, particularly $R^5$ and $R^6$ are independently selected from hydrogen and trifluoromethyl, more particularly $R^5$ and $R^6$ are hydrogen.

In one embodiment of the first or second aspect, $R^1$ is $NR^{1a}R^{1b}$ and $R^{1a}$ and $R^{1b}$ are independently hydrogen or $C_{1-4}$ alkyl, or $R^{1a}$ and $R^{1b}$ together with the nitrogen atom to which they are attached form a 4 to 6 membered heterocyclic ring; n is 0 or 1; when present, $R^2$ is methyl; $R^3$ is $C_{1-4}$ haloalkyl or $C_{1-4}$ haloalkoxy; $R^4$ is hydrogen or methyl; $R^5$ and $R^6$ are independently selected from hydrogen and $C_{1-4}$ haloalkyl.

In one embodiment of the first or second aspect, $R^{1a}$ and $R^{1b}$ are independently $C_{1-4}$ alkyl, or $R^{1a}$ and $R^{1b}$ together with the nitrogen atom to which they are attached form a 4 or 5 membered heterocyclic ring; n is 1; $R^2$ is methyl and m is 1; $R^3$ is trifluoromethyl, trifluoromethoxy or difluoromethoxy; $R^4$ is hydrogen or methyl; $R^5$ and $R^6$ are independently selected from hydrogen and trifluoromethyl.

In one embodiment of the first or second aspect, $R^{1a}$ and $R^{1b}$ are $C_{1-4}$ alkyl, or $R^{1a}$ and $R^{1b}$ together with the nitrogen atom to which they are attached form a morphonlinyl, pyrrolidine or azetidinyl ring, n is 1; $R^2$ is 2-methyl relative to the piperazine carbonyl bond; $R^3$ is trifluoromethyl, trifluoromethoxy or difluoromethoxy; $R^4$ is hydrogen; $R^5$ and $R^6$ are independently selected from hydrogen.

In one embodiment of the first or second aspect, the compound is selected from a compound of Examples 1 to 76, or a salt thereof.

In a third aspect, the compound is a compound of formula (Ic), or a pharmaceutically acceptable salt thereof, for use in therapy, wherein

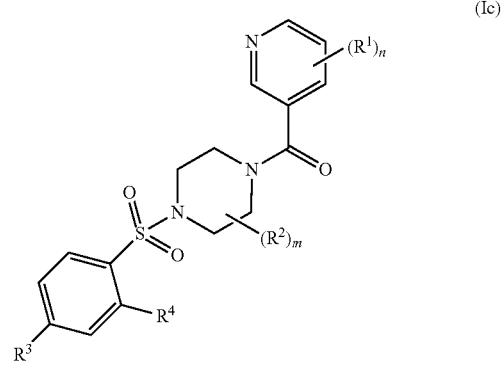

(Ic)

$R^1$ represents $C_{1-4}$ alkyl, $C_{1-4}$ alkoxy, cyano or morpholinyl;
m and n independently represent an integer from 0 to 1;
$R^2$ represents $C_{1-4}$ alkyl;
$R^3$ represents halogen, cyano, trifluoromethyl, trifluoromethoxy or difluoromethoxy;
$R^4$ represents hydrogen or methyl;
such that when $R^3$ represents cyano, $R^4$ represents a group other than hydrogen.

In a fourth aspect, the compound is a compound of formula (Ic), or a salt thereof, wherein
$R^1$ represents $C_{1-4}$ alkyl, $C_{1-4}$ alkoxy, cyano or morpholinyl;
m and n independently represent an integer from 0 to 1;
$R^2$ represents $C_{1-4}$ alkyl;
$R^3$ represents halogen, cyano, trifluoromethyl, trifluoromethoxy or difluoromethoxy;

$R^4$ represents hydrogen or methyl;

such that when $R^3$ represents cyano, $R^4$ represents a group other than hydrogen;

with the proviso that the compound is not

1-[(4-chlorophenyl)sulfonyl]-4-[(6-methyl-3-pyridinyl)carbonyl]piperazine;

1-(3-pyridinylcarbonyl)-4-{[4-(trifluoromethyl)phenyl]sulfonyl}piperazine;

1-(3-pyridinylcarbonyl)-4-({4-[(trifluoromethyl)oxy]phenyl}sulfonyl)piperazine;

1-[(6-methyl-3-pyridinyl)carbonyl]-4-({4-[(trifluoromethyl)oxy]phenyl}sulfonyl)piperazine;

1-{[6-(methyloxy)-3-pyridinyl]carbonyl}-4-({4-[(trifluoromethyl)oxy]phenyl}sulfonyl)piperazine;

4-({4-[(6-methyl-3-pyridinyl)carbonyl]-1-piperazinyl}sulfonyl)benzonitrile;

1-{[2-(ethyloxy)-3-pyridinyl]carbonyl}-4-{[4-(trifluoromethyl)phenyl]sulfonyl}piperazine; and 1-{[2-(ethyloxy)-3-pyridinyl]carbonyl}-4-({4-[(trifluoromethyl)oxy]phenyl}sulfonyl)piperazine.

In one embodiment of the third or fourth aspect, n represents 0 or 1. In a further embodiment of the third or fourth aspect, n represents 1. When present, in one embodiment of the third or fourth aspect, $R^1$ represents $C_{1-4}$ alkyl, $C_{1-4}$ alkoxy or cyano. In a further embodiment of the third or fourth aspect, $R^1$ represents $C_{1-4}$ alkyl. In a yet further embodiment of the third or fourth aspect, $R^1$ represents methyl, particularly 2-methyl or 6-methyl, even more particularly 2-methyl.

In one embodiment of the third or fourth aspect, m represents 0 or 1. In a further embodiment of the third or fourth aspect, m represents 1.

When present, in one embodiment of the third or fourth aspect, $R^2$ represents $C_{1-3}$ alkyl. In a further embodiment of the third or fourth aspect, $R^2$ represents methyl or ethyl. In a yet further embodiment of the third or fourth aspect, $R^2$ represents methyl.

In one embodiment of the third or fourth aspect, $R^3$ represents chlorine, cyano, trifluoromethyl, trifluoromethoxy or difluoromethoxy. In a further embodiment of the third or fourth aspect, $R^3$ represents trifluoromethyl.

In another embodiment of the first to fourth aspect, the compound is (2S)-2-Methyl-1-[(6-methyl-3-pyridinyl)carbonyl]-4-{[4-(trifluoromethyl)phenyl]sulfonyl}piperazine; or (2S)-2-Methyl-1-[(2-methyl-3-pyridinyl)carbonyl]-4-{[4-(trifluoromethyl)phenyl]sulfonyl}piperazine, or a salt thereof. More particularly the compound is (2S)-2-Methyl-1-[(2-methyl-3-pyridinyl)carbonyl]-4-{[4-(trifluoromethyl)phenyl]sulfonyl}piperazine, or a salt thereof.

Certain compounds as defined in the first to fourth aspect may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

It will be appreciated by those skilled in the art that certain protected derivatives of the compounds as defined in the first to fourth aspect, which may be made prior to a final deprotection stage, may not possess pharmacological activity as such, but may, in certain instances, be administered orally or parenterally and thereafter metabolised in the body to form compounds as defined in the first to fourth aspect which are pharmacologically active. Such derivatives may therefore be described as "prodrugs". All protected derivatives and prodrugs of compounds defined in the first to fourth aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds as defined in the first and second aspects. Therefore, in a further aspect, the invention provides a prodrug of a compound as defined in the first to fourth aspect.

It will be appreciated that certain compounds as defined in the first to fourth aspect, or their salts, may exist as solvates, such as hydrates. Where solvates exist, this invention includes within its scope stoichiometric and non-stoichiometric solvates.

It will be appreciated that certain compounds as defined in the first to fourth aspect, or their salts, may exist in more than one polymorphic form. The invention extends to all such forms whether in a pure polymorphic form or when admixed with any other material, such as another polymorphic form.

Certain compounds as defined in the first to fourth aspect are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The subject invention also includes isotopically-labelled compounds, which are identical to the compounds as defined in the first to fourth aspect, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$ and $^{18}F$.

Compounds as defined in the first to fourth aspect and salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labelled reagent. In one embodiment, compounds as defined in the first to fourth aspect or salts thereof are not isotopically labelled.

Throughout the specification, general formulae are designated by Roman numerals (I), (II), (III), (IV), etc. Subsets of these general formulae are defined as (Ia), (Ib), (Ic), etc. . . . (IVa), (IVb), (IVc), etc.

Compounds as defined in the first to fourth aspect may be prepared as set forth in the following Schemes and in the examples. The following processes form another aspect of the present invention.

The present invention also provides a process for the preparation of a compound as defined in the first to fourth aspect, or a salt thereof, which process comprises:

(a) reacting a compound of formula (II)

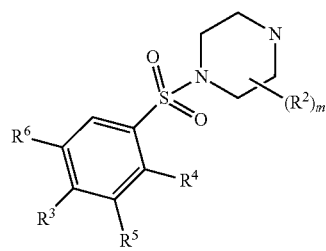

or a derivative thereof, with a compound of formula (III)

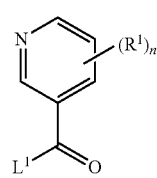

wherein $R^1$, $R^2$, $R^3$, $R^4$, $R^5$, $R^6$, m and n are as defined above and $L^1$ represents a suitable leaving group such as a halogen atom (e.g. chlorine or bromine) or a hydroxyl group activated by commercially available amide coupling reagents (for example, HOBT, HBTU or HATU);

(b) reacting a compound of formula (IV)

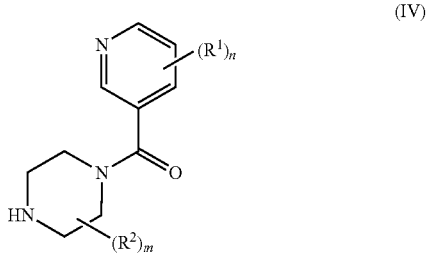

with a compound of formula (V)

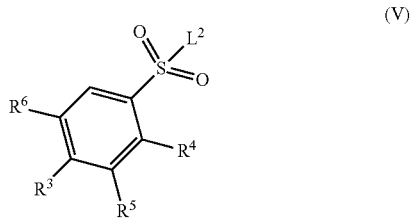

wherein $R^1$, $R^2$, $R^3$, $R^4$, $R^5$, $R^6$, m and n are as defined above and $L^2$ represents a suitable leaving group such as a halogen atom (e.g. chlorine or bromine);

(c) interconversion to other compounds as defined in the first to fourth aspect.

Process (a) typically comprises reaction of a compound of formula (II) with a compound of formula (III) in a suitable solvent such as acetonitrile, tetrahydrofuran, N,N-dimethylformamide or dichloromethane, in the presence of a suitable base, (for example, triethylamine, di-isopropylethylamine or DIPEA) at 0° C. to ambient temperature (for example, room temperature).

Process (b) typically comprises reaction of a compound of formula (IV) and (V) in the presence of a suitable solvent (such as dichloromethane or acetonitrile) in the presence of a suitable base, (for example triethylamine, di-isopropylethylamine or DI PEA) at 0° C. to ambient temperature (for example, room temperature). Alternatively, process (b) may typically comprise reaction of the intermediates in the presence of a suitable base as a solvent (for example pyridine).

Process (c) may be performed using conventional interconversion procedures such as epimerisation, oxidation, reduction, alkylation, nucleophilic or electrophilic aromatic substitution. One such example of interconversion may be interconversion of a compound as defined in the first to fourth aspect wherein $R^3$ represents bromine to a compound as defined in the first to fourth aspect wherein $R^3$ represents cyano. Such interconversion may be carried out by treating the bromine compound with a cyanide salt (for example copper (I) cyanide) in a suitable solvent (such as N,N-dimethylformamide) at elevated temperatures (such as 200° C. using microwave irradiation). Alternatively the interconversion may be carried out using a cyanide salt (for example zinc cyanide) in the presence of a source of a palladium catalyst (for example tris(dibenzylideneacetone)dipalladium(0) and ligand (for example 1,1′-bis(diphenylphosphino)ferrocene)

in a suitable solvent (such as N,N-dimethylformamide) at elevated temperatures (such as 120° C.).

This kind of interconversion may also be carried out on intermediates of compounds as defined in the first to fourth aspect, for example on compounds of formula (VII). Another example of interconversion is from a compound of formula (VII) where $R^4$ represents bromine to a compound where $R^4$ represents methyl. Such interconversion may be carried out by treating the bromine compound with a methylboronic acid or ester (eg trimethylboroxin) in the presence of a palladium catalyst (for example tetrakistriphenylphosphine palladium (0)) in a suitable solvent (such as 1,4-dioxane) at elevated temperatures (such as 100° C.).

A different example of an interconversion to other compounds as defined in the first to fourth aspect is shown in the Scheme below:

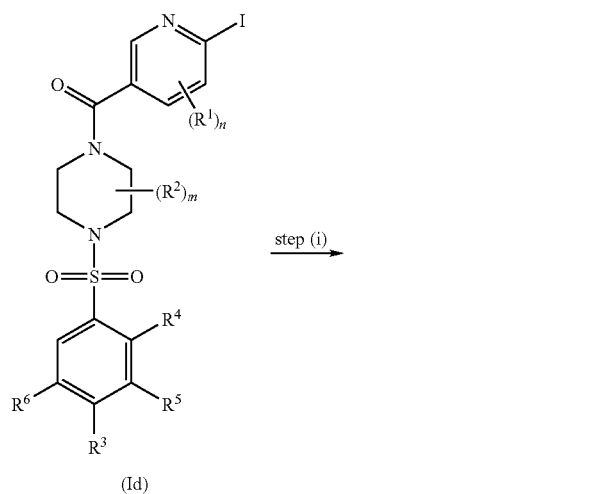

(Id)

step (i)

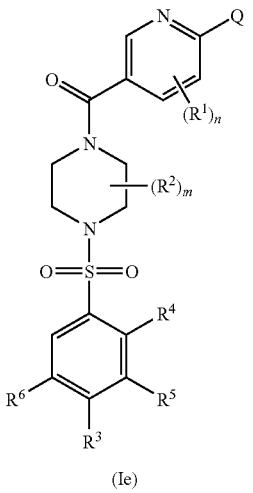

(Ie)

wherein $R^1$, $R^2$, $R^3$, $R^4$, $R^5$, $R^6$ and m are as defined above, n is 0 or 1, and Q is $C_{1-4}$ alkyl or $C_{3-6}$ cycloalkyl.

Step (i) typically comprises reacting a compound of formula (Id) with a $C_{1-4}$alkylzinc halide in the presence of a catalyst such as $PdCl_2(dppf)$ in a suitable solvent such as 1,4-dioxane at an elevated temperature (such as 100° C.). Alternatively, step (i) may comprise reacting a compound of formula (Id) with a suitable $C_{1-4}$alkylboronic acid or $C_{3-6}$ cycloalkylboronic acid in the presence of a catalyst such as palladium(II) acetate, ligand such as tricyclohexylphosphine and base such as potassium phosphate in a solvent such as a mixture of toluene and water at an elevated temperature.

A further example of an interconversion to other compounds as defined in the first to fourth aspect is shown in the Scheme below:

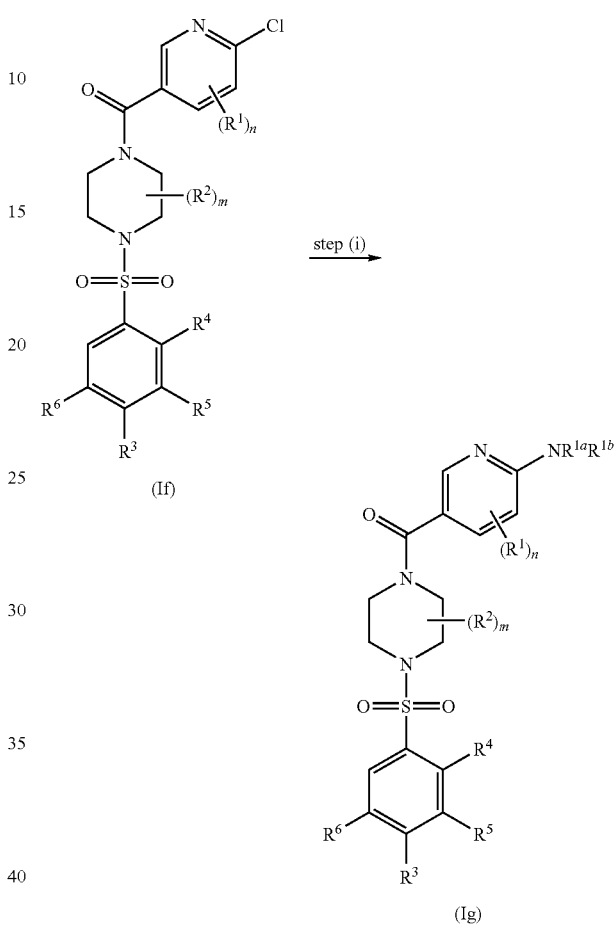

wherein $R^1$, $R^{1a}$, $R^{1b}$, $R^2$, $R^3$, $R^4$, $R^5$, $R^6$ and m are as defined above, and n is 0 or 1.

Step (i) typically comprises reacting a compound of formula (If) with an amine $HNR^{1a}R^{1b}$ in a suitable solvent such as isopropanol in the microwave in the temperature range 100-180° C. for the time required to achieve good conversion to (Ie), such as, for example, 1 h to 48 h.

Compounds of formula (II) may be prepared in accordance with the following Scheme:

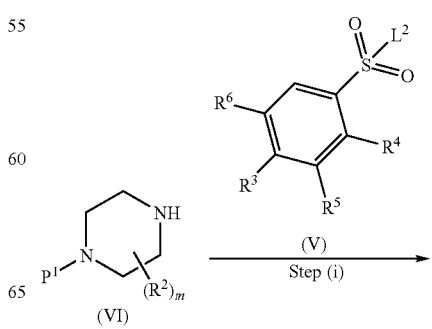

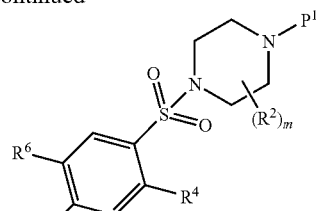

(VII)

↓ Step (ii)

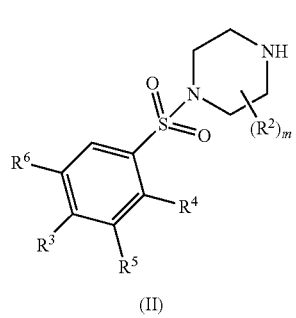

(II)

wherein $R^2$, $R^3$, $R^4$, $R^5$, $R^6$, m and $L^2$ are as defined above and $P^1$ represents a suitable protecting group such as t-butoxycarbonyl. Alternatively, if $P^1$ is H then step (ii) is not required.

Step (i) typically comprises reacting a compound of formula (V) and (VI) in a suitable solvent, such as DCM or MeCN in the presence of a base, (for example triethylamine, di-isopropylethylamine or DIPEA) at 0° C. to ambient temperature (for example ambient temperature). Alternatively, step (i) may typically be carried out using a suitable base as a solvent, for example pyridine, or step (i) may also be carried out in a solvent mixture of THF and water, using a suitable base such as sodium hydroxide.

Step (ii) typically comprises a deprotection reaction. For example, when $P^1$ represents t-butoxycarbonyl, step (ii) will typically comprise treatment with an acid, for example hydrochloric acid or trifluoroacetic acid, in a solvent (such as 1,4-dioxane, dichloromethane or a mixture of methanol and 1,4-dioxane).

Compounds of formula (IV) may be prepared in accordance with the following Scheme:

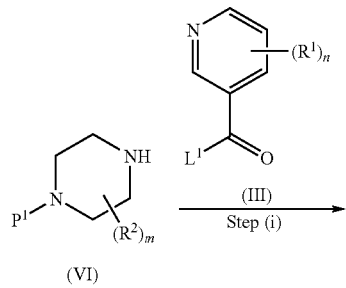

(VI)

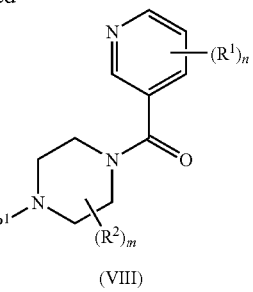

(VIII)

↓ Step (ii)

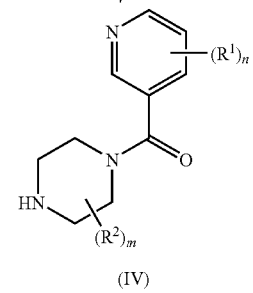

(IV)

wherein $R^2$, m, $R^1$, n and $P^1$ are as defined above.

Step (i) typically comprises reacting a compound of formula (VI) with a compound of formula (III) in a suitable solvent (such as MeCN, THF, DMF or DCM) in the presence of a suitable base (for example, triethylamine, di-isopropylethylamine or DIPEA) at 0° C. to ambient temperature (for example ambient temperature).

Step (ii) typically comprises a deprotection reaction which may be carried out in an analogous manner to Step (ii) above.

Compounds of formula (III), (V) and (VI) are either commercially available, or may be prepared by known methods.

Compounds which can block the $Ca_v2.2$ calcium channels may be useful in the treatment or prophylaxis of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

'Chronic articular pain' conditions include rheumatoid arthritis, osteoarthritis, rheumatoid spondylitis, gouty arthritis and juvenile arthritis.

'Pain associated with functional bowel disorders' includes non-ulcer dyspepsia, non-cardiac chest pain and irritable bowel syndrome.

'Neuropathic pain' syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions which could potentially be treated by compounds as defined in the first to fourth aspect include neurodegenerative diseases and neurodegeneration, neurodegeneration following trauma, tinnitus, dependence on a dependence-inducing agent such as opioids (e.g. morphine), CNS depressants (e.g. ethanol), psychostimulants (e.g. cocaine) and nicotine.

Neurodegenerative diseases include dementia, particularly degenerative dementia (including senile dementia, dementia with Lewy bodies, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment associated with ageing, particularly Age Associated Memory Impairment.

Compounds as defined in the first to fourth aspect may also be useful for neuroprotection and in the treatment or prophylaxis of neurodegeneration following trauma such as stroke, cardiac arrest, pulmonary bypass, traumatic brain injury, spinal cord injury or the like.

Another condition which could potentially be treated by compounds as defined in the first to fourth aspect is spasticity or muscular hypertonicity.

Thus, in an embodiment of the first and third aspect, the therapy is to the treatment or prophylaxis of any of the disorders described herein, in particular pain. In one particular embodiment, the therapy is to the treatment of any of the disorders described herein, in particular pain.

According to a further aspect, there is provided a use of a compound as defined in the first to fourth aspect, or a pharmaceutically acceptable salt thereof, in the manufacture of a medicament for the treatment or prophylaxis of any of the disorders herein, in particular pain. More particularly, there is provided a use of a compound as defined in the first to fourth aspect, or a pharmaceutically acceptable salt thereof, in the manufacture of a medicament for the treatment of any of the disorders herein.

According to another aspect, there is provided a method of treatment or prophylaxis of any of the disorders herein, in particular pain in humans, which method comprises the administration to the human in need of such treatment or prophylaxis, an effective amount of a compound as defined in the first to fourth aspect, or a pharmaceutically acceptable salt thereof.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

In order to use a compound as defined in the first to fourth aspect or a pharmaceutically acceptable salt thereof for the treatment or prophylaxis of humans and other mammals it is normally formulated in accordance with standard pharmaceutical practice as a pharmaceutical composition. Therefore in another aspect of the invention there is provided a pharmaceutical composition comprising a compound as defined in the first to fourth aspect, or a pharmaceutically acceptable salt thereof, adapted for use in human or veterinary medicine.

In order to use compounds as defined in the first to fourth aspect in therapy, they will normally be formulated into a pharmaceutical composition in accordance with standard pharmaceutical practice. The present invention also provides a pharmaceutical composition, which comprises a compound as defined in the first to fourth aspect, or a pharmaceutically acceptable salt thereof, and optionally a pharmaceutically acceptable excipient.

When used in the treatment or prophylaxis of pain, the compound as defined in the first to fourth aspect or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for Compound COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying antirheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for Compound sumatriptan, naratriptan, zolmitriptan, eletriptan, frovatriptan, almotriptan or rizatriptan; nicotinic acetyl choline (nACh) receptor modulators; glutamate receptor modulators, for Compound modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQKv7 channel openers, such as retigabine; Additional COX-2 inhibitors are disclosed in U.S. Pat. Nos. 5,474,995, 5,633,272; 5,466,823, 6,310,099 and 6,291,523; and in WO 96/25405, WO 97/38986, WO 98/03484, WO 97/14691, WO99/12930, WO00/26216, WO00/52008, WO00/38311, WO01/58881 and WO02/18374.

When used in the treatment or prophylaxis of Alzheimer's disease, the compound as defined in the first to fourth aspect or a pharmaceutically acceptable salt thereof may be used in combination with other medicaments indicated to be useful as either disease modifying or symptomatic treatments of Alzheimer's disease.

Suitable examples of such other therapeutic agents may be agents known to modify cholinergic transmission such as $5\text{-}HT_{1A}$ antagonists, (e.g. lecozotan), 5-HT6 antagonists, M1 muscarinic agonists, M2 muscarinic antagonist, acetylcholinesterase inhibitors (e.g tetrahydroaminoacridine, donepezil or rivastigmine), or allosteric modulators, nicotinic receptor agonists or allosteric modulators, symptomatic agents such as 5-HT6 receptor antagonists, e.g. SB742457, H3 receptor antagonists e.g. GSK189254 and GSK239512, 5-HT4 receptor agonist, PPAR agonists, also NMDA receptor antagonists or modulators, also disease modifying agents such as β or γ-secretase inhibitors (e.g. R-flurbiprofen), also AMPA positive modulators and Glycine Transporter Reuptake inhibitors.

When a compound as defined in the first to fourth aspect or a pharmaceutically acceptable salt thereof is used in combination with another therapeutic agent, the compounds may be administered either sequentially or simultaneously by any convenient route.

The invention thus provides, in a further aspect, a combination comprising a compound as defined in the first to fourth aspect or a pharmaceutically acceptable salt thereof together with a further therapeutic agent or agents.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 60% by weight, of the active material, depending on the method of administration. The dose of the compound as defined in the first to fourth aspect or a pharmaceutically acceptable salt thereof used in the treatment or prophylaxis of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks, months, years or even life.

A further aspect to the invention is a pharmaceutical composition comprising 0.05 to 1000 mg of a compound as defined in the first to fourth aspect or a pharmaceutically acceptable salt thereof, and 0 to 3 g more suitably 0 to 2 g of at least one pharmaceutically acceptable carrier.

All publications, including but not limited to patents and patent applications, cited in this specification are herein incorporated by reference as if each individual publication were specifically and individually indicated to be incorporated by reference herein as though fully set forth.

Abbreviations:

Ar: argon aq.: aqueous dba: dibenzylideneacetone

DCM: dichloromethane

DIPEA: N,N-diisopropylethylamine

DMF: N,N-dimethylformamide

DMSO: dimethylsulfoxide

DPPF: 1,1'-bis(diphenylphosphino)ferrocene

EDC: 1-ethyl-3-(3-dimethyllaminopropyl)carbodiimide hydrochloride

EtOAc: ethyl acetate

HATU: O-(7-azabenzotriazol-1-yl)-N,N,N',N'-tetramethyluronium hexafluorophosphate HBTU: O-benzotriazole-N,N,N',N'-tetramethyl-uronium-hexafluoro-phosphate HOBT: hydroxybenzotriazole iHex: isohexane LCMS: Liquid Chromatography Mass Spectrometry MS: mass spectrometry MeCN: acetonitrile MDAP: mass directed automated preparative liquid chromatography.

MeOH: methanol rt: room temperature sat.: saturated

SCX: strong cation exchange chromatography

SPE: solid phase extraction

SP4: Biotage—SP4® automated purification system

THF: tetrahydrofuran

TFA: trifluoroacetic acid $Pd_2(dba)_3$: tris(dibenzylideneacetone)dipalladium(0)

$Pd(PPh_3)_4$: tetrakis(triphenylphosphine)palladium h: hour(s)

min: minute(s)

Boc: t-butoxycarbonyl $PdCl_2(dppf)_3$: (1,1'-bis(diphenylphosphino)ferrocene) dichloropalladium(II)

API-ES: atmospheric pressure ionization electro-spray

EXAMPLES

The preparation of a number of supporting compounds as defined in the first to fourth aspect are described below.

In the procedures that follow, after each starting material, reference to an intermediate is typically provided. This is provided merely for assistance to the skilled chemist. The starting material may not necessarily have been prepared from the batch referred to.

Description 1

1-{[4-(Trifluoromethyl)phenyl]sulfonyl}piperazine

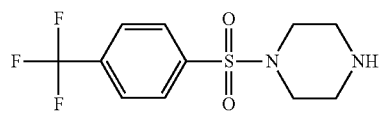

To a solution of 1,1-dimethylethyl 1-piperazinecarboxylate (5.00 g, 26.8 mmol) in DCM (200 ml) was added DIPEA (9.85 ml, 56.4 mmol) and then 4-(trifluoromethyl)benzenesulfonyl chloride (7.22 g, 29.5 mmol). The reaction mixture was stirred for 1.5 hours at room temperature. The reaction mixture was then reduced to dryness in vacuo, to yield the title compound.

m/z (API-ES) 295 [M+H−100]$^+$

To a solution of 1,1-dimethylethyl 4-{[4-(trifluoromethyl)phenyl]sulfonyl}-1-piperazinecarboxylate in 1,4-dioxane (100 ml) was added 4M HCl in 1,4-dioxane (50 ml, 200 mmol) and 3 drops of distilled water. The reaction mixture was stirred overnight. Reaction mixture was then reduced to dryness in vacuo.

The residue was dissolved in DCM (200 ml) and washed with 2M NaOH (50 ml), twice.

The organic layer was dried over magnesium sulphate, the insolubles removed by filtration, and filtrate reduced to dryness in vacuo to yield the title compound (6.60 g) as a pale yellow solid.

m/z (API-ES) 295 [M+H]$^+$
$^1$H NMR (400 MHz, CHLOROFORM-d) δ ppm 2.89-2.98 (m, 4 H), 2.99-3.09 (m, 4 H), 3.71 (s, 1 H), 7.77-7.85 (m, 2 H), 7.85-7.92 (m, 2 H).

Description 2

(3S)-3-Methyl-1-{[4-(trifluoromethyl)phenyl]sulfonyl}piperazine

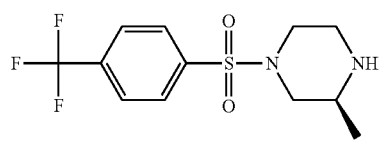

To a solution of 1,1-dimethylethyl (2S)-2-methyl-1-piperazinecarboxylate (5.00 g, 25.0 mmol, supplier Small Molecules Inc.) in DCM (200 ml) was added DIPEA (11.4 ml, 65.5 mmol) and 4-(trifluoromethyl)benzenesulfonyl chloride (5.68 g, 23.2 mmol). The reaction mixture was stirred for 1 hour. DCM (200 ml) was added to the reaction mixture which was transferred to a separating funnel. The solution was washed with saturated sodium bicarbonate solution (50 ml, twice) and then with distilled water (50 ml). The organic layer was dried over magnesium sulphate which was removed by filtration and the filtrate was evaporated to dryness on the rotary evaporator to give 8.90 g of white solid. The solid was dissolved in 1,4-dioxane (30 ml) and 4M HCl in 1,4-dioxane (10 ml) and a few drops of water were added and the reaction mixture was stirred for 1 hour. Then further 4M HCl in 1,4-dioxane (20 ml) was added and the reaction stirred overnight. The reaction mixture was evaporated to dryness in vacuo and the residue was dissolved in MeOH and loaded onto an SCX column (Biotage). The column was washed with MeOH (2 column volumes) and the product was eluted with 1M ammonia in MeOH. LCMS showed a large amount of desired product present in the MeOH wash, so this was evaporated to dryness on the rotary evaporator. The residue was dissolved in EtOAc (100 ml) and extracted with 2M aq. HCl (50 ml). The aqueous layer was basified with 2M aqueous NaOH solution until pH remained above 7 and extracted with EtOAc (100 ml). The organic layer was evaporated to dryness on the rotary evaporator to yield the title compound as a white solid (4.34 g).

m/z (API-ES) 309 [M+H]$^+$
1H NMR (400 MHz, MeOH-d4) δ ppm 1.36 (d, J=6.6 Hz, 3 H), 2.62-2.73 (m, 1 H), 2.85-2.97 (m, 1 H), 3.19-3.29 (m, 1 H), 3.45-3.54 (m, 2 H), 3.80-3.95 (m, 2 H), 7.95 (d, J=8.3 Hz, 2 H), 8.05 (d, J=8.3 Hz, 2 H).

Alternative Synthesis of (3S)-3-Methyl-1-{[4-(trifluoromethyl)phenyl]sulfonyl}piperazine: Description 2a (2S)-2-methylpiperazine (15 g, 150 mmol) was dissolved in tetrahydrofuran (300 mL) and the solution was cooled down to 0° C. Sodium hydroxide (150 mL, 449 mmol) was added, then 4-(trifluoromethyl)benzenesulfonyl chloride (40 g, 164 mmol) (dissolved in 200 ml THF) was added dropwise and the resulting mixture was stirred for 1 h. Further 4-(trifluoromethyl)benzenesulfonyl chloride (0.06 eq, 2.2 g) was added and mixture stirred for 10 min. The mixture was diluted with DCM (500 ml) and water (500 ml) and stirred for 5 min. The phases were separated, the aqueous layer was extracted with DCM (1000 ml) and the organic phases concentrated under reduced pressure. The residue was taken-up with 1 M HCl (500 ml) and washed with DCM in order to extracted impurities. The aqueous phase was basified to pH=9 with NaOH 3M, extracted with DCM (3×500 ml) and the combined organic phases dried over Na$_2$SO$_4$ before the solvent was removed under reduced pressure to give the title compound (30 g).

m/z (API-ES) 309 [M+H]$^+$
1H NMR (400 MHz, CDCl$_3$) δ ppm 1.06 (d, J=7.2 Hz, 3H), 1.94 (t, J=10.4 Hz, 1H), (td, J=11.2, 4.0 Hz, 1H), 2.88-3.07 (m, 3H), 3.66 (m, 2H), 7.83 (d, J=8.4 Hz, 2H), 7.90 (d, J=8.4 Hz, 2H).

Description 3

1,1-Dimethylethyl (3S)-4-[(4-chlorophenyl)sulfonyl]-3-methyl-1-piperazinecarboxylate

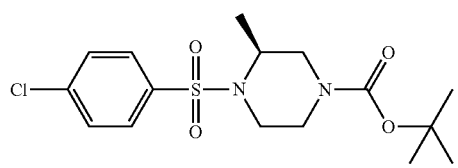

To a solution of 1,1-dimethylethyl (3S)-3-methyl-1-piperazinecarboxylate (10.0 g, 49.9 mmol, supplier Aldrich) in pyridine (30 ml) was added 4-chlorobenzenesulfonyl chloride (12.7 g, 59.9 mmol) portionwise. The reaction was stirred at room temperature under an argon atmosphere for 2 hours. The reaction was then evaporated, partitioned between 2N aq. HCl (70 ml) and DCM (80 ml). The aqueous was further extracted with DCM (2×80 ml) and the combined DCM layers were passed through a hydrophobic frit and evaporated. The product was dried under vacuum at 40° C. for 18 hours to yield the title compound as an orange solid (24.14 g).

¹H-NMR (400 MHz, CHLOROFORM-d) δ 1.03 (3H, dd, J=6.8, 0.4 Hz), 1.43 (9H, s), 3.05 (1H, m), 3.10 (1H, m), 3.15 (1H, m), 3.60 (1H, m), 3.80 (1H,m), 4.10 (2H, m), 7.48 (2H, m), 7.74 (2H, m).

Description 4

(2S)-1-[(4-Chlorophenyl)sulfonyl]-2-methylpiperazine hydrochloride

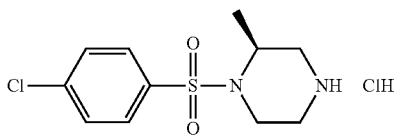

1,1-Dimethylethyl (3S)-4-[(4-chlorophenyl)sulfonyl]-3-methyl-1-piperazinecarboxylate (may be prepared as described in Description 3) (crude weight 24.14 g, theoretical 49.9 mmol) was suspended in 4M HCl in 1,4-dioxane (80 mL, excess) and stirred vigorously for 3 hours. The sample was evaporated, suspended in diethyl ether (100 mL) and filtered through a sinter. The collected solid was dried under vacuum at 40° C. for 18 hours to yield the title compound as a yellow solid (15.45 g).

m/z (API-ES) 275 [M+H]⁺

¹H NMR (MeOH-d4) δ 1.21 (3H, d, J=7.0 Hz), 2.91-3.45 (5H, br m), 3.89 (1H, m), 4.38 (1H, m), 7.64 (2H, m), 7.88 (2H, m).

Description 5

1,1-Dimethylethyl(3R)-3-methyl-4-{[4-(trifluoromethyl)phenyl]sulfonyl}-1-piperazinecarboxylate

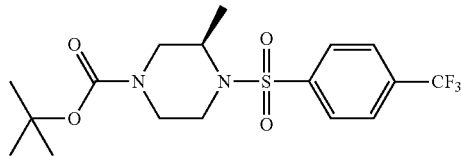

To a solution of 1,1-dimethylethyl (3R)-3-methyl-1-piperazinecarboxylate (1.5 g, 7.49 mmol, supplier Aldrich) in DCM (30 ml) was added DIPEA (1.962 ml, 11.23 mmol) and then portionwise addition of 4-(trifluoromethyl)benzenesulfonyl chloride (2.2 g, 8.99 mmol) at room temperature. The resultant mixture was stirred under an atmosphere of Ar for 2 hours before addition of 1M HCl solution (75 ml) and DCM (75 ml). The layers were separated and the aqueous layer was then re-extracted with DCM (75 ml), the organic layers were combined and washed with saturated brine solution (100 ml). The organic layers were then separated, dried (MgSO₄) and concentrated to dryness giving the title compound (3.39 g).

m/z (API-ES) 309 [M+H–100]⁺

¹H NMR (400 MHz, CHLOROFORM-d) δ ppm 1.03 (d, J=6.7 Hz, 3 H), 1.43 (s, 9 H), 2.65-3.22 (m, 3 H), 3.54-4.27 (m, 4 H), 7.78 (d, J=8.2 Hz, 2 H), 7.93 (d, J=8.2 Hz, 2 H).

Description 6

(2R)-2-methyl-1-{[4-(trifluoromethyl)phenyl]sulfonyl}piperazine hydrochloride

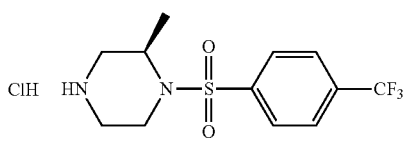

To a solution of 1,1-dimethylethyl (3R)-3-methyl-4-{[4-(trifluoromethyl)phenyl]sulfonyl}-1-piperazinecarboxylate (may be prepared as described in Description 5) (3.39 g, 8.30 mmol) in 1,4-dioxane (20 ml) was added HCl (4M in 1,4-dioxane) (10.37 ml, 41.5 mmol) and the resultant mixture stirred under an atmosphere of Ar for 16 hours. A further 5 ml of 4M HCl in dioxane was added and the mixture stirred at room temperature for 72 hours. The mixture was concentrated to dryness and the residue triturated with diethyl ether and the solid collected by filtration giving the the title compound (2.507 g) as a white powder.

m/z (API-ES) 309 [M+H]⁺

1H NMR (400MHz, DMSO-d₆) δ ppm 1.16 (d, J=7.0 Hz, 3H), 2.72-2.86 (m, 1 H), 2.96 (dd, J=13.0, 4.28 Hz, 1 H), 3.08-3.24 (m, 2 H), 3.26-3.34 (m, 1H), 3.70-3.84 (m, 1H), 4.16-4.32 (m, 1H), 8.03 (d, J=8.4 Hz, 2 H), 8.09 (d, J=8.3 Hz, 2 H), 9.16 (br. s. 2H).

Description 7

1,1-Dimethylethyl (3S)-3-methyl-4-{[4-(trifluoromethyl)phenyl]sulfonyl}-1-piperazinecarboxylate

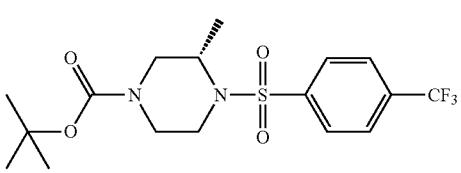

To a solution of 1,1-dimethylethyl (3S)-3-methyl-1-piperazinecarboxylate (2.05 g, 10.24 mmol) in DCM (50 ml) was added DIPEA (2.68 ml, 15.35 mmol) and the mixture stirred at room temperature for 10 minutes before addition of 4-(trifluoromethyl)benzenesulfonyl chloride (3.00 g, 12.28 mmol) at 0° C. The resultant mixture stirred under an atmosphere of Argon for 16 hours before addition of water (50 ml) and DCM (30 ml). The layers were separated using a hydrophobic frit and the organic layers concentrated to dryness giving the title compound (4.4 g) as a white solid.

m/z (API-ES) 309 [M+H−100]⁺

¹H NMR (400 MHz, CHLOROFORM-d) δ ppm 1.03 (d, J=6.7 Hz, 3 H) 1.43 (s, 9 H) 2.59-3.33 (m, 3 H) 3.43-4.35 (m, 4 H) 7.77 (d, J=8.3 Hz, 2 H) 7.93 (d, J=8.3 Hz, 2 H).

Description 8

(2S)-2-Methyl-1-{[4-(trifluoromethyl)phenyl]sulfonyl}piperazine hydrochloride

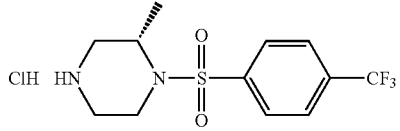

To a solution of 1,1-dimethylethyl (3S)-3-methyl-4-{[4-(trifluoromethyl)phenyl]sulfonyl}-1-piperazinecarboxylate (may be prepared as described in Description 7) (4.4 g, 10.77 mmol) in 1,4-dioxane (30 ml) was added HCl (4M in 1,4-dioxane) (5.39 ml, 21.55 mmol) and the mixture stirred at room temperature for 2 hours. A further portion of HCl (4M in 1,4-dioxane) (16.16 ml, 64.6 mmol) was then added and the mixture stirred for a further 16 hours. The volatiles were then removed in vacuo giving the title compound (3.8 g) as a white solid.

m/z (API-ES) 309 [M+H]⁺

¹H NMR (400 MHz, MeOH-d4) δ ppm 1.20 (d, J=7.1 Hz, 3 H) 2.95-3.25 (m, 3 H) 3.36-3.45 (m, 1 H) 3.56-3.77 (m, 1 H) 3.87-4.00 (m, 1 H) 4.34-4.51 (m, 1 H) 7.94 (d, J=8.3 Hz, 2 H) 8.08 (d, J=8.2 Hz, 2 H)

Description 9

1,1-Dimethylethyl (2S)-4-[(4-bromo-2-methyl phenyl)sulfonyl]-2-methyl-1-piperazinecarboxylate

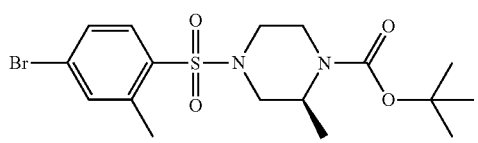

To a solution of 1,1-dimethylethyl (2S)-2-methyl-1-piperazinecarboxylate (2.00 g, 9.99 mmol) and DIPEA (2.62 ml, 14.98 mmol) in dry DCM (25 ml) at 0° C. under Ar was added 4-bromo-2-methylbenzenesulfonyl chloride (2.96 g, 10.98 mmol) and the resulting yellow solution allowed to warm to rt, then stirred at rt for 18 hours. Semi-saturated aq NH₄Cl (40 ml) was added, then the aq extracted with DCM (30 ml). The combined organic layers were passed through a hydrophobic frit, then concentrated in vacuo to give a yellow oil (5.01 g). Flash chromatography (silica; Flash 40M; linear gradient (6-50%) EtOAc in isohexane) gave the title compound as a pale yellow oil (3.52 g).

m/z (API-ES) 333 and 335, 1:1, [M+H−100]⁺

¹H NMR (400 MHz, CHLOROFORM-d) δ ppm 1.19 (d, J=6.7 Hz, 3 H), 1.44 (s, 9 H), 2.59 (td, J=12.0, 3.4 Hz, 1 H), 2.61 (s, 3 H), 2.78 (dd, J=12.0, 3.8 Hz, 1 H), 3.11 (td, J=12.0, 3.2 Hz, 1 H), 3.44 (dt, J=12.0, 2.0 Hz, 1 H), 3.59-3.65 (m, 1 H), 3.93 (d, J=12.0 Hz, 1 H), 4.33 (br. s., 1 H), 7.45-7.51 (m, 2 H), 7.72 (d, J=8.4 Hz, 1 H).

Description 10

1,1-Dimethylethyl (2S)-4-[(4-cyano-2-methylphenyl)sulfonyl]-2-methyl-1-piperazinecarboxylate

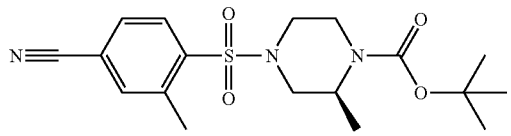

Ar was bubbled through a solution of 1,1-dimethylethyl (2S)-4-[(4-bromo-2-methylphenyl)sulfonyl]-2-methyl-1-piperazinecarboxylate (may be prepared as described in Description 9) (3.51 g, 8.10 mmol) in dry DMF (40 ml) for 0.5 hours, then Zn(CN)₂ (0.523 g, 4.45 mmol), Pd₂(dba)₃ (0.223 g, 0.243 mmol) and DPPF (0.269 g, 0.486 mmol) were added and the resulting brown solution stirred at 120° C. under Ar for 2.5 hours. The mixture was cooled to room temperature, concentrated in vacuo and the residue partitioned between DCM (100 ml) and water (100 ml). The aqueous layer was extracted with DCM (2×100 ml), then the combined organic layers passed through a hydrophobic frit. Concentration gave a brown residue (4.31 g). Flash chromatography (silica; linear gradient (6-50%) EtOAc in isohexane) gave the title compound as a yellow solid (2.88 g).

m/z (API-ES) 280 [M+H−100]⁺

¹H NMR (400 MHz, CHLOROFORM-d) δ ppm 1.20 (d, J=6.8 Hz, 3 H), 1.44 (s, 9 H), 2.65 (td, J=12.0, 3.4 Hz, 1 H), 2.68 (s, 3 H), 2.86 (dd, J=12.0, 4.2 Hz, 1 H), 3.13 (td, J=12.0, 2.8 Hz, 1 H), 3.49 (dt, J=12.0, 1.8 Hz, 1 H), 3.63-3.69 (m, 1 H), 3.95 (d, J=12.0 Hz, 1 H), 4.35 (br. s., 1 H), 7.61-7.65 (m, 2 H), 7.96 (d, J=6.8 Hz, 1 H).

Description 11

3-Methyl-4-{[(3S)-3-methyl-1-piperazinyl]sulfonyl}benzonitrile

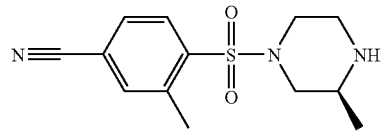

A solution of 1,1-dimethylethyl (2S)-4-[(4-cyano-2-methylphenyl)sulfonyl]-2-methyl-1-piperazinecarboxylate (may be prepared as described in Description 10) (2.88 g, 7.59 mmol) and TFA (10 ml, 130 mmol) in dry DCM (10 ml) was stirred at room temperature for 1 hour, then concentrated in vacuo, azeotroping with toluene (25 ml) to give a brown oil. This was partitioned between DCM (50 ml) and saturated aqueous NaHCO₃ (50 ml), then the aqueous layer was extracted with DCM (50 ml). The combined organic layers were passed through a hydrophobic frit and concentrated in vacuo to give the title compound as a yellow oil (2.29 g).

m/z (API-ES) 280 [M+H]+

1H NMR (400 MHz, CHLOROFORM-d) δ ppm 1.06 (d, J=6.4 Hz, 3 H), 2.33 (dd, J=11.6, 10.2 Hz, 1 H), 2.67 (s, 3 H), 2.69-2.75 (td, J=11.5, 3.1 Hz, 1 H), 2.82-2.92 (m, 2 H), 3.03 (dt, J=12.1, 2.6 Hz, 1 H), 3.54-3.65 (m, 2 H), 7.59-7.67 (m, 2 H), 7.99 (d, J=8.6 Hz, 1 H).

Description 12

(3R)-3-Methyl-1-{[4-(trifluoromethyl)phenyl]sulfonyl}piperazine

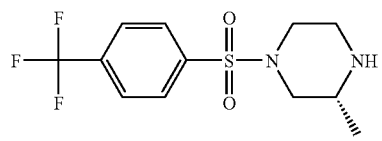

To a solution of 1,1-dimethylethyl (2R)-2-methyl-1-piperazinecarboxylate (2.95 g, 14.73 mmol) in DCM (120 ml) was added DIPEA (5.40 ml, 30.9 mmol) and then 4-(trifluoromethyl)benzenesulfonyl chloride (3.96 g, 16.20 mmol). The reaction mixture was stirred 2.5 hours at room temperature then washed with water (250 ml), dried on a phase separation cartridge and concentrated in vacuo. The obtained product was dissolved in 1,4-dioxane (60 ml) and treated with 4M aq. HCl in 1,4-dioxane (18.41 ml, 73.6 mmol) overnight. The mixture was concentrated under vacuo then dissolved in EtOAc (150 ml), washed with 2N aq. NaOH solution (200 ml) then dried on a phase separation cartridge and concentrated in vacuo. The product was then dissolved in EtOAc (100 ml) and extracted with 2M aq. HCl (2×200 ml). 2M aq. NaOH solution was added to the aqueous layer until basic pH then the product was extracted with EtOAc (500 ml). The organic layer was dried on a phase separation cartridge and concentrated under vacuo to give the title compound (3.76 g).

m/z (API-ES) 309 [M+H]+

1H NMR (400 MHz, CHLOROFORM-d) δ ppm 1.05 (d, J=6.4 Hz, 3 H) 1.93 (t, J=10.6 Hz, 1 H) 2.31 (td, J=11.2, 3.4 Hz, 1 H) 2.86-3.08 (m, 3 H) 3.59-3.73 (m, 2 H) 7.82 (d, J=8.3 Hz, 2 H) 7.89 (d, J=8.2 Hz, 2 H).

Description 13

(2S)-2-Methyl-1-[(6-methyl-3-pyridinyl)carbonyl]piperazine

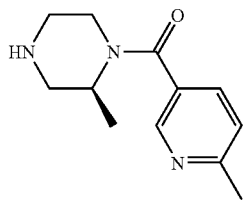

To a solution of 1,1-dimethylethyl (3S)-3-methyl-1-piperazinecarboxylate (1 g, 4.99 mmol) in DMF (5 ml) was added 6-methyl-3-pyridinecarboxylic acid (0.685 g, 0.340 mmol), HOBT.H2O (0.765 g, 4.99 mmol) and HBTU (1.894 g, 4.99 mmol). Finally DIPEA (2.62 ml, 14.98 mmol) was added and the reaction mixture was stirred at room temperature for 20 hours. Solvent was removed by evaporation and EtOAc was added to the residue and the solution was extracted with saturated aqueous sodium bicarbonate and sodium chloride solutions. The organic layer was evaporated to dryness and dissolved in dioxane (100 ml) and stirred with 4M HCl in dioxane (15 ml) and water (0.25 ml) overnight. The solution was evaporated to dryness and purified using an ion exchange column (SCX, Biotage) to give the title compound as an oil (1.04 g)

1H NMR (400 MHz, CHLOROFORM-d) δ ppm 1.36 (dd, J=6.8, 1.8 Hz, 3 H), 2.02-3.35 (m, 7 H), 2.60 (s, 3 H), 7.22 (d, J=8.0 Hz, 1 H), 7.63 (d, J=8.0, 2.3 Hz, 1 H), 8.53 (d, J=1.8 Hz, 1 H).

Description 14

1-[(6-methyl-3-pyridinyl)carbonyl]piperazine

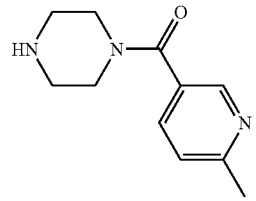

This compound was prepared in a similar manner as the compound of Description 13.

1H NMR (400 MHz, CDCl3) δ ppm 2.60 (s, 3H), 2.8-3.1 (m, 4H), 3.4-3.6 (m, 2H), 3.7-3.9 (m, 2H), 7.22 (d, J=8.0 Hz, 1H), 7.66 (dd, J=8.0, 2.4 Hz, 1H), 8.55 (d, J=2.4 Hz, 1H).

Description 15

1,1-Dimethylethyl (3S)-4-[(4-bromo-2-methyl phenyl)sulfonyl]-3-methyl-1-piperazinecarboxylate

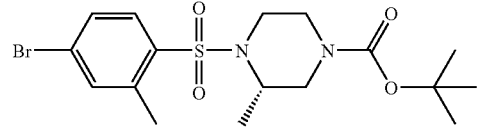

To a solution of 1,1-dimethylethyl (3S)-3-methyl-1-piperazinecarboxylate (2.00 g, 9.99 mmol) and DIPEA (2.62 ml, 15.0 mmol) in dry DCM (25 ml) at 0° C. under Ar was added 4-bromo-2-methylbenzenesulfonyl chloride (2.96 g, 11.0 mmol) and the resulting yellow solution allowed to warm to rt, then stirred at rt for 90 min. Semi-saturated NH4Cl (25 ml) was added, then the aqueous extracted with DCM (20 ml). The combined organic layers were passed through a hydrophobic frit, then concentrated under vacuum to give a pale yellow oil (4.99 g). Flash chromatography (silica; Flash 40M; linear gradient (6-50%) EtOAc in isohexane) gave the title compound as a viscous clear oil (4.46 g).

m/z (API-ES) 333 and 335 [M+H−100]+

1H NMR (400 MHz, CHLOROFORM-d) δ ppm 1.18 (d, J=6.7 Hz, 3 H), 1.45 (s, 9 H), 2.56 (s, 3 H), 2.69-2.91 (m, 1 H), 2.93-3.12 (m, 1 H), 3.20 (td, J=12.8 and 3.3 Hz, 1 H), 3.37 (d, J=12.8 Hz, 1 H), 3.78-4.06 (m, 3 H), 7.47 (s, 2 H), 7.83 (d, J=8.3 Hz, 1 H).

Description 16

1,1-dimethylethyl(3S)-4-[(4-cyano-2-methylphenyl)sulfonyl]-3-methyl-1-piperazinecarboxylate

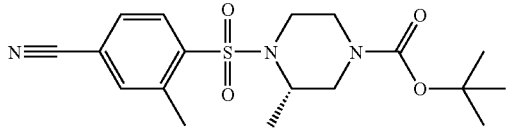

Ar was bubbled through a solution of 1,1-dimethylethyl (3S)-4-[(4-bromo-2-methylphenyl)sulfonyl]-3-methyl-1-piperazinecarboxylate (may be prepared as described in Description 15) (4.32 g, 9.98 mmol) in dry DMF (40 ml) for 30 min, then Zn(CN)$_2$ (0.645 g, 5.49 mmol), Pd$_2$(dba)$_3$ (0.274 g, 0.299 mmol) and DPPF (0.332 g, 0.599 mmol) were added and the resulting brown solution stirred at 120° C. under Ar for 40 min. The mixture was cooled to room temperature, concentrated under vacuum and the residue partitioned between DCM (50 ml) and semi-saturated brine (50 ml). The aqueous layer was extracted with DCM (2×50 ml), then the combined organic layers passed through a hydrophobic frit. Concentration under vaccum gave a brown residue (5.75 g). Flash chromatography (silica; Flash 40M; linear gradient (6-50%) EtOAc in isohexane) gave the title compound as a white solid (3.71 g).

m/z (API-ES) 280 [M+H−100]$^+$ $^1$H NMR (400 MHz, CHLOROFORM-d) δ ppm 1.18 (d, J=6.7 Hz, 3 H), 1.44 (s, 9 H), 2.62 (s, 3 H), 2.70-2.90 (m, 1 H), 2.94-3.14 (m, 1 H), 3.23 (td, J=12.8 and 3.2 Hz, 1 H), 3.41 (d, J=12.8 Hz, 1 H), 3.80-4.19 (m, 3 H), 7.59-7.64 (m, 2 H), 8.07 (d, J=8.4 Hz, 1 H)

Description 17

3-methyl-4-{[(2S)-2-methyl-1-piperazinyl]sulfonyl}benzonitrile

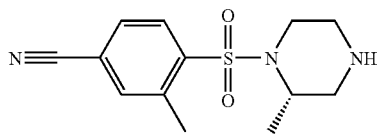

A solution of 1,1-dimethylethyl (3S)-4-[(4-cyano-2-methylphenyl)sulfonyl]-3-methyl-1-piperazinecarboxylate (may be prepared as described in Description 16) (3.71 g, 9.78 mmol) and TFA (5.00 ml, 64.9 mmol) in dry DCM (15 ml) was stirred at rt for 1 h, then concentrated under vacuum, azeotroping with toluene (25 ml). The residue was dissolved in MeOH (20 ml) and added to an SCX-2 cartridge (50 g), washing with MeOH. The product was eluted with 2M NH$_3$ in MeOH; concentration under vacuum gave the title compound as a white solid (2.50 g).

m/z (API-ES) 280 [M+H]$^+$ $^1$H NMR (400 MHz, CHLOROFORM-d) δ ppm 1.30 (d, J=6.8 Hz, 3 H), 2.63 (s, 3 H), 2.66 (td, J=11.9 and 3.9 Hz, 1 H), 2.79 (d, J=12.3 Hz, 1 H), 2.94 (dd, J=12.3 and 3.5 Hz, 2 H), 3.24 (td, J=11.6 and 3.0 Hz, 1 H), 3.27-3.33 (m, 1 H), 3.91-3.98 (m, 1 H), 7.58-7.62 (m, 2 H), 8.07 (d, J=8.6 Hz, 1 H)

Description 18

1,1-dimethylethyl (2R)-4-[(4-bromo-2-methyl phenyl)sulfonyl]-2-methyl-1-piperazinecarboxylate

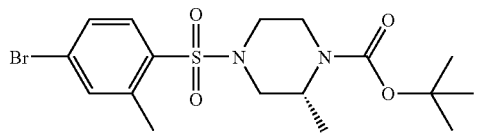

To a solution of 1,1-dimethylethyl (2R)-2-methyl-1-piperazinecarboxylate (2.00 g, 9.99 mmol) and DIPEA (2.62 ml, 15.0 mmol) in dry DCM (25 ml) at 0° C. under Ar was added 4-bromo-2-methylbenzenesulfonyl chloride (2.96 g, 11.0 mmol) and the resulting pale yellow solution stirred at 0° C. for 1 h. Semi-saturated NH$_4$Cl (20 ml) was added, then the aqueous extracted with DCM (30 ml). The combined organic layers were passed through a hydrophobic frit, then concentrated under vacuum to give a yellow oil (5.12 g). Flash chromatography (silica; Flash 40M; linear gradient (6-50%) EtOAc in isohexane) gave the title compound as a clear viscous oil (4.34 g).

m/z (API-ES) 333 and 335 [M+H−100]$^+$ $^1$H NMR (400 MHz, CHLOROFORM-d) δ ppm 1.19 (d, J=6.7 Hz, 3 H), 1.44 (s, 9 H), 2.59 (td, J=12.0, 3.2 Hz, 1 H), 2.61 (s, 3 H), 2.78 (dd, J=11.9, 3.8 Hz, 1 H), 3.11 (td, J=12.9, 3.5 Hz, 1 H), 3.44 (dt, J=11.9, 1.9 Hz, 1 H), 3.62 (ddt, J=11.8, 3.5, 1.8 Hz, 1 H), 3.93 (d, J=13.3 Hz, 1 H), 4.29-4.37 (m, 1 H), 7.44-7.51 (m, 2 H), 7.72 (d, J=8.4 Hz, 1 H).

Description 19

1,1-dimethylethyl (2R)-4-[(4-cyano-2-methyl phenyl)sulfonyl]-2-methyl-1-piperazinecarboxylate

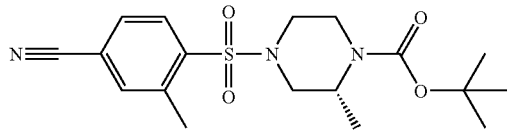

Ar was bubbled through a solution of 1,1-dimethylethyl (2R)-4-[(4-bromo-2-methylphenyl)sulfonyl]-2-methyl-1-piperazinecarboxylate (may be prepared as described in Description 18) (4.34 g, 10.0 mmol) in dry DMF (40 ml) for 30 min, then Zn(CN)$_2$ (0.647 g, 5.51 mmol), Pd$_2$(dba)$_3$ (0.275 g, 0.300 mmol) and DPPF (0.333 g, 0.601 mmol) were added and the resulting brown solution stirred at 120° C. under Ar for 1 h. The mixture was cooled to room temperature, concentrated under vacuum and the residue partitioned between DCM (100 ml) and water (100 ml). The aqueous layer was extracted with DCM (2×50 ml), then the combined organic layers passed through a hydrophobic frit. Concentration gave a brown residue that was purified by flash chromatography (silica; Flash 40M; linear gradient (8-66%) EtOAc in isohexane) to give the title compound as a viscous pale yellow oil (3.42 g).

m/z (API-ES) 280 [M+H−100]+

1H NMR (400 MHz, CHLOROFORM-d) δ ppm 1.19 (d, J=6.8 Hz, 3 H), 1.44 (s, 9 H), 2.65 (td, J=12.1, 3.5 Hz, 1 H), 2.68 (s, 3 H), 2.85 (dd, J=12.1, 3.7 Hz, 1 H), 3.12 (td, J=13.0, 3.5 Hz, 1 H), 3.48 (dt, J=12.0, 1.9 Hz, 1 H), 3.66 (ddt, J=11.9, 3.5, 1.8 Hz, 1 H), 3.94 (d, J=13.4 Hz, 1 H), 4.30-4.39 (m, 1 H), 7.61-7.65 (m, 2 H), 7.96 (d, J=8.6 Hz, 1 H).

Description 20

3-methyl-4-{[(3R)-3-methyl-1-piperazinyl]sulfonyl}benzonitrile

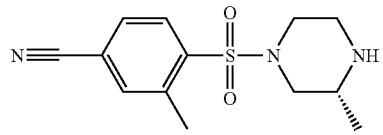

A solution of 1,1-dimethylethyl (2R)-4-[(4-cyano-2-methylphenyl)sulfonyl]-2-methyl-1-piperazinecarboxylate (may be prepared as described in Description 19) (3.24 g, 8.54 mmol) and TFA (7.00 ml, 91.0 mmol) in dry DCM (10 ml) was stirred at rt for 1 h, then concentrated under vacuum, azetroping with toluene (25 ml) to give an orange oil. This was redissolved in MeOH (10 ml) then applied to an SCX-2 cartridge (50 g), washing with MeOH. The product was eluted with 2M NH3 in MeOH; concentration under vacuum gave the title compound as a pale orange oil (8.17 mmol).

m/z (API-ES) 280 [M+H]+

1H NMR (400 MHz, CHLOROFORM-d) δ ppm 1.06 (d, J=6.4 Hz, 3 H), 2.30 (dd, J=11.7, 10.4 Hz, 1 H), 2.67 (s, 3 H), 2.70 (td, J=11.6, 3.1 Hz, 1 H), 2.81-2.88 (m, 1 H), 2.89 (td, J=11.5, 3.1 Hz, 1 H), 3.04 (dt, J=12.1, 2.5 Hz, 1 H), 3.54-3.63 (m, 2 H), 7.60-7.64 (m, 2 H), 7.98 (d, J=8.6 Hz, 1 H).

Description 21

(3S)-3-methyl-1-({4-[(trifluoromethyl)oxy]phenyl}sulfonyl)piperazine

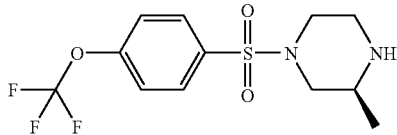

A solution of 4-[(trifluoromethyl)oxy]benzenesulfonyl chloride (3.25 g, 12.48 mmol), 1,1-dimethylethyl(2S)-2-methyl-1-piperazinecarboxylate (2.5 g, 12.48 mmol) and DIPEA (4.58 ml, 26.2 mmol) in DCM (200 ml) was stirred at room temperature overnight. The mixture was washed with saturated aqueous NaHCO3 then brine. The organics were concentrated under vacuum, then re-dissolved in dioxane (200 ml). A 4M solution of HCl in dioxane (20 ml) and water (0.5 ml) were added and the mixture stirred overnight. The mixture was concentrated under vacuum, applied to an SCX-2 cartridge (20 g) washing with MeOH and eluting with 0.5M NH3 in MeOH; concentration under vacuum gave the title compound as a white solid (2.56 g).

m/z (API-ES) 325[M+H]+

1H NMR (400 MHz, CHLOROFORM-d) δ ppm 1.04 (d, J=6.4 Hz, 3 H), 1.93 (t, J=10.6 Hz, 1 H), 2.31 (td, J=11.2, 3.4 Hz, 1 H), 2.86-3.07 (m, 3 H), 3.58-3.68 (m, 2 H), 7.37 (d, J=8.9 Hz, 2 H), 7.77-7.84 (m, 2 H)

Description 22

(3R)-3-methyl-1-({4-[(trifluoromethyl)oxy]phenyl}sulfonyl)piperazine

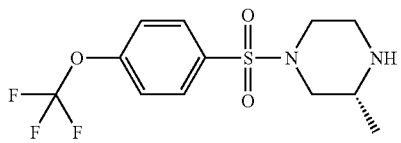

To a solution of 1,1-dimethylethyl (2R)-2-methyl-1-piperazinecarboxylate (2.00 g, 9.99 mmol) in DCM (200 ml) was added DIPEA (3.66 ml, 20.97 mmol) and then 4-[(trifluoromethyl)oxy]benzenesulfonyl chloride (1.69 ml, 9.99 mmol) and the resulting mixture stirred at room temperature for 90 min. The reaction mixture was then concentrated under vacuum and re-dissolved in 1,4-dioxane (100 ml). A 4M solution of HCl in 1,4-dioxane (100 ml, 400 mmol) and a few drops of distilled water were added and the mixture stirred for 3 h. The reaction mixture was concentrated under vacuum, re-dissolved in DCM (200 ml) and washed with 2M aqueous NaOH (2×50 ml). The organic layer was dried (MgSO4), filtered and concentrated under vacuum. The residue was dissolved in ether and concentrated under vacuum. The oil was dissolved in MeOH (150 ml), applied to an SCX cartridge (50 g), which was washed with MeOH, DCM and MeOH again. The product was eluted from the column with 2M ammonia in methanol, DCM and then 2M ammonia in methanol; concentration under vacuum gave the title compound as a yellow transparent oil (2.92 g).

m/z (API-ES) 325 [M+H]+

1H NMR (400 MHz, CHLOROFORM-d) δ ppm 1.04 (d, J=6.4 Hz, 3 H), 1.93 (t, J=10.6 Hz, 1 H), 2.31 (td, J=11.2, 3.5 Hz, 1 H), 2.86-3.07 (m, 3 H), 3.58-3.69 (m, 2 H), 7.37 (d, J=8.1 Hz, 2 H), 7.77-7.85 (m, 2 H)

Description 23

1,1-dimethylethyl (2S)-4-{[2-bromo-4-(trifluoromethyl)phenyl]sulfonyl}-2-methyl-1-piperazinecarboxylate

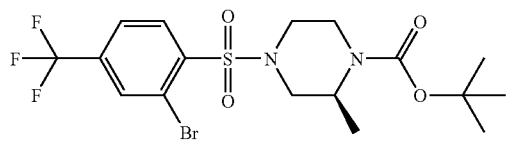

To a solution of 1,1-dimethylethyl (2S)-2-methyl-1-piperazinecarboxylate (1.20 g, 5.99 mmol) and DIPEA (5.45 ml, 31.2 mmol) in dry DCM (60 ml) at 0° C. under Ar was added 2-bromo-4-(trifluoromethyl)benzenesulfonyl chloride (2.04 g, 6.29 mmol) and the resulting clear solution stirred at 0° C. for 2 h. EtOAc (100 ml) and saturated aqueous NaHCO₃ (100 ml) were added, the layers separated, then the organic layers washed with 2M aqueous HCl (100 ml) and passed through an hydrophobic frit. The solvent was removed to leave the title compound (2.36 g).

m/z (API-ES) 387 and 389 [M+H−100]⁺

¹H NMR (400 MHz, DMSO-d₆) δ ppm 1.02 (d, J=6.7 Hz, 3 H), 1.38 (s, 9 H), 2.83 (td, J=12.3, 3.4 Hz, 1 H), 3.00 (dd, J=12.6, 3.8 Hz, 1 H), 3.07 (td, J=12.8, 3.0 Hz, 1 H), 3.45 (d, J=12.6 Hz, 1 H), 3.73 (d, J=12.2 Hz, 1 H), 3.81 (d, J=12.8 Hz, 1 H), 4.15-4.24 (m, 1 H), 7.99 (dd, J=8.2, 1.3 Hz, 1 H), 8.18 (d, J=8.2 Hz, 1 H), 8.30 (d, J=1.1 Hz, 1 H)

Description 24

(3S)-3-methyl-1-{[2-methyl-4-(trifluoromethyl)phenyl]sulfonyl}piperazine

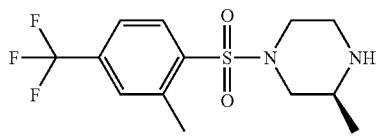

A solution of 1,1-dimethylethyl (2S)-4-{[2-bromo-4-(trifluoromethyl)phenyl]sulfonyl}-2-methyl-1-piperazinecarboxylate (may be prepared as described in Description 23) (1.00 g, 2.05 mmol), potassium carbonate (0.737 g, 5.34 mmol) in 1,4-dioxane (43 ml) were stirred for 5 min then trimethylboroxin (0.743 ml, 5.34 mmol) and Pd(Ph₃P)₄ (0.403 g, 0.349 mmol) were added and the reaction mixture heated at 100° C. overnight. EtOAc (100 ml) was added, then the mixture was washed with aqueous sodium bicarbonate (100 ml), water (100 ml) and concentrated under vacuum. Flash chromatography (silica; linear gradient (0-20%) EtOAc in isohexane) gave 1,1-dimethylethyl (2S)-2-methyl-4-{[2-methyl-4-(trifluoromethyl)phenyl]sulfonyl}-1-piperazinecarboxylate (0.785 g). This material was re-dissolved in DCM (10 ml) and 1,4-dioxane (3 ml), then HCl in dioxane (5 eq) was added and the mixture stirred at room temperature for 4 h. Aqueous sodium bicarbonate (20 ml) and EtOAc (20 ml) were added and the organic phase washed with aqueous sodium bicarbonate (2×10 ml), brine (10 ml) and dried using a hydrophobic frit. The solvent was removed under vacuum. The residue was re-dissolved in DCM (10 ml) and 1,4-dioxane (3 ml), then 4M HCl in 1,4-dioxane (6.97 mL, 27.9 mmol) added. The mixture was stirred at room temperature for 4 h. The solvent was evaporated under vacuum to give the title compound (0.615 g) as the hydrochloride salt.

m/z (API-ES) 323 [M+H]⁺

¹H NMR (400 MHz, DMSO-d₆) δ ppm 1.22 (d, J=6.5 Hz, 3 H), 2.66 (s, 3 H), 2.77 (dd, J=12.8, 10.5 Hz, 1 H), 2.93-3.11 (m, 2 H), 3.29-3.39 (m, 2 H), 3.63-3.75 (m, 2 H), 7.84 (d, J=8.3 Hz, 1 H), 7.94 (s, 1 H), 8.03 (d, J=8.3 Hz, 1 H), 9.18 (br. s., 2 H)

Description 25

1,1-dimethylethyl (2S)-4-{[2-bromo-5-(trifluoromethyl)phenyl]sulfonyl}-2-methyl-1-piperazinecarboxylate

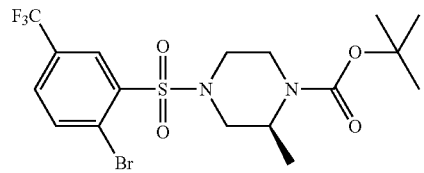

To a solution of 1,1-dimethylethyl (2S)-2-methyl-1-piperazinecarboxylate (1.18 g, 4.98 mmol) in dichloromethane (40 ml) was added DIPEA (2.70 ml, 15.45 mmol) and then 2-bromo-5-(trifluoromethyl)benzenesulfonyl chloride (1.613 g, 4.98 mmol). The reaction mixture was stirred for 1 h 20 min at room temperature. The reaction mixture was then washed with water (50 ml), dried on a phase separation cartridge and concentrated under vacuum to give the crude title compound (2.5 g) which was used directly in the next step.

m/z (API-ES) 387+389 (1:1) [(M-Boc)+H]⁺

Description 26

1,1-dimethylethyl (2S)-2-methyl-4-{[2-methyl-5-(trifluoromethyl)phenyl]sulfonyl}-1-piperazinecarboxylate

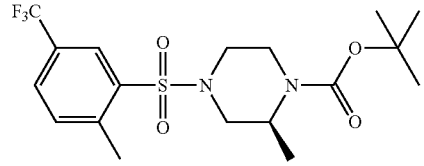

1,1-dimethylethyl (2S)-4-{[2-bromo-5-(trifluoromethyl)phenyl]sulfonyl}-2-methyl-1-piperazinecarboxylate (may be prepared as described in Description 25) (2.5 g, 5.13 mmol), potassium carbonate (1.134 g, 8.21 mmol) in 1,4-dioxane (80 ml) were stirred for 5 min then trimethylboroxin (1.142 ml, 8.21 mmol) and Pd(PPh₃)₄ (0.593 g, 0.513 mmol) were added and the reaction mixture heated at 100° C. for 1.5 h. Further trimethylboroxin (0.5 mL) was added and the reaction heated for 30 min before it was allowed to cool overnight.

The mixture was concentrated under vacuum then EtOAc (120 ml) added, washed with 200 ml of water, dried on a phase separation cartridge and evaporated under vacuum. The crude material (2.8 g) was purified via Biotage (40+M silica column) using a gradient EtOAc/i-Hex from 0/100 to 30/70. Desired fractions collected and concentrated under vacuum to give the title compound (2.1 g).

m/z (API-ES) 323 [(M-Boc)+H]⁺

Description 27

(3S)-3-methyl-1-{[2-methyl-5-(trifluoromethyl)phenyl]sulfonyl}piperazine

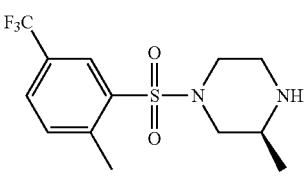

1,1-dimethylethyl (2S)-2-methyl-4-{[2-methyl-5-(trifluoromethyl)phenyl]sulfonyl}-1-piperazinecarboxylate (may be prepared as described in Description 26) (2.1 g, 4.97 mmol) in 1,4-Dioxane (50 mL) was treated by 4 M HCl in dioxane (6.21 mL, 24.85 mmol). The reaction mixture was stirred overnight at room temperature. LCMS showed a 1:1 ratio between starting material and expected product. 4 M HCl in dioxane (6.21 mL, 24.85 mmol) was added and the reaction mixture stirred for 4 h. LCMS showed about 10% of remaining starting material. 4 M HCl in dioxane (6.21 mL, 24.85 mmol) was added and the reaction mixture stirred for 1 h.

The reaction mixture was then concentrated under vacuum, dissolved in EtOAc (100 ml) and extracted with 2N HCl (3×75 ml). 2N NaOH was added to the aqueous until basic then product extracted with EtOAc, dried on a phase separation cartridge and concentrated under vacuum to give the title compound (1.16 g).

m/z (API-ES) 323 [M+H]$^+$

Description 28

1,1-dimethylethyl 4-{[2-bromo-5-(trifluoromethyl)phenyl]sulfonyl}-1-piperazinecarboxylate

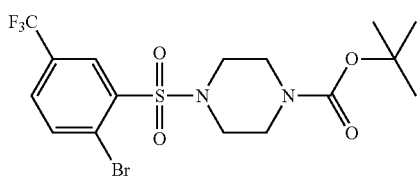

To a solution of 1,1-dimethylethyl 1-piperazinecarboxylate (1 g, 5.37 mmol) in DCM (40 ml) was added DIPEA (1.969 ml, 11.28 mmol) and then 2-bromo-5-(trifluoromethyl)benzenesulfonyl chloride (1.737 g, 5.37 mmol). The mixture was stirred for 1 h 20 min at room temperature before it was washed with water (50 ml), dried on a phase separation cartridge and concentrated under vacuum.

Crude product was dissolved in MeOH and eluted through a 10 g SCX cartridge (elution with MeOH), concentrated under vacuum to give (2.59 g).

m/z (API-ES) 373+375 (1:1) [(M-Boc)+H]$^+$

Description 29

1,1-dimethylethyl 4-{[2-methyl-5-(trifluoromethyl)phenyl]sulfonyl}-1-piperazinecarboxylate

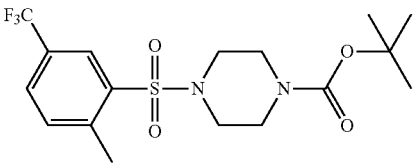

1,1-dimethylethyl 4-{[2-bromo-5-(trifluoromethyl)phenyl]sulfonyl}-1-piperazinecarboxylate (may be prepared as described in Description 28) (2.59 g, 5.47 mmol), potassium carbonate (1.513 g, 10.94 mmol) in 1,4-dioxane (80 ml) were stirred for 5 min then trimethylboroxin (1.523 ml, 10.94 mmol) and Pd(PPh$_3$)$_4$ (0.632 g, 0.547 mmol) were added and the reaction mixture heated at 100° C. for 1.5 h. Further trimethylboroxin (0.5 mL) was added and the mixture heated at 100° C. for 30 min before allowing to cool overnight. The mixture was concentrated under vacuum then EtOAc (150 ml) added, washed with 200 ml of water, dried on a phase separation cartridge and evaporated under vacuum. The crude material (3.1 g) was purified via Biotage (40+M silica column) using a gradient EtOAc/i-hex from 10/90 to 30/70. Desired fractions were collected and concentrated under vacuum to give the title compound (2.1 g).

m/z (API-ES) 309 [(M-Boc)+H]$^+$

Description 30

1-{[2-methyl-5-(trifluoromethyl)phenyl]sulfonyl}piperazine

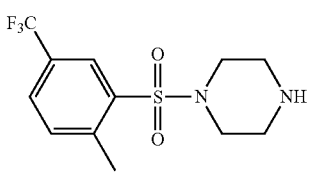

1,1-dimethylethyl 4-{[2-methyl-5-(trifluoromethyl)phenyl]sulfonyl}-1-piperazinecarboxylate (may be prepared as described in Description 29) (2.1 g, 5.14 mmol) in 1,4-dioxane (50 mL) was treated by HCl 4M in dioxane (6.43 mL, 25.7 mmol). The reaction mixture was stirred overnight at room temperature. LCMS showed a mixture of starting material and product so 8 ml of 4M HCl in dioxane were added. LCMS after 2 h showed still some starting material so 5 ml of 4M HCl in dioxane were added. LCMS after 2 h showed traces of starting material.

The reaction mixture was concentrated under vacuum, dissolved in EtOAc (70 ml) and extracted with 2N HCl (3×80 ml). 2N NaOH was added to the aqueous layer until basic, then the product extracted with EtOAc, dried on a phase separation cartridge and concentrated under vacuum to give the title compound (1.38 g).

m/z (API-ES) 309 [M+H]$^+$

Description 31

(2S)-4-{[2-bromo-4-(trifluoromethyl)phenyl]sulfonyl}-2-methyl-1-[(6-methyl-3-pyridinyl)carbonyl]piperazine

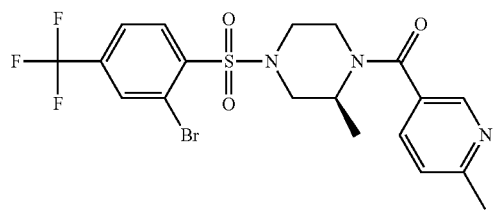

To a solution of (2S)-2-methyl-1-[(6-methyl-3-pyridinyl)carbonyl]piperazine (may be prepared as described in Description 13) (200 mg, 0.912 mmol) in DCM (10 mL) was added 2-bromo-4-(trifluoromethyl)benzenesulfonyl chloride (295 mg, 0.912 mmol) followed by DIPEA (0.159 mL, 0.912 mmol). The reaction mixture was left stirring at room temperature for 15 h. The solvent was removed by evaporation and the crude residue was dissolved in DCM (30 ml), washed with saturated sodium bicarbonate (40 ml), dried (hydrophobic frit) and evaporated under vacuum. The crude product was purified by silica chromatography using a gradient EtOAc/iso-hexane from 20/80 to 100/0. The desired fractions were combined and concentrated under vacuum to give the title compound (216 mg).

m/z (API-ES) 506+508 (1:1) [M+H]$^+$ $^1$H NMR (400 MHz, DMSO-d$_6$) δ ppm 1.34 (d, J=6.8 Hz, 3H), 2.60 (s, 3H), 2.88 (td, J=12.0, 3.2 Hz, 1H), 3.08 (dd, J=12.8, 3.4 Hz, 1H), 3.40 (m, 1H), 3.64 (d, J=12.8 Hz, 1H), 3.87 (d, J=12.4 Hz, 1H), 3.9-4.8 (brm, 2H), 7.23 (d, J=8.0 Hz, 1H), 7.54 (d, J=8.0 Hz, 1H), 7.62 (d, J=8.4 Hz, 1H), 8.02 (s, 1H), 8.21 (d, J=8.4 Hz, 1H), 8.51 (s, 1H)

Description 32

1-{[2-bromo-4-(trifluoromethyl)phenyl]sulfonyl}-4-[(6-methyl-3-pyridinyl)carbonyl]piperazine

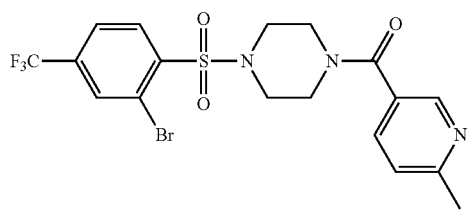

This compound was prepared in a similar manner as the compound of Description 31 using the corresponding reactants.

m/z (API-ES) 492+494 (1:1) [M+H]$^+$

Description 33

2-methyl-3-pyridinecarbonyl chloride

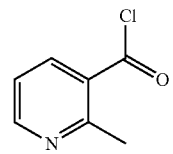

2-methyl-3-pyridinecarboxylic acid (20 g, 146 mmol) was dissolved in thionyl chloride (60 ml, 822 mmol) and stirred at room temperature for 24 h. The reaction was concentrated under reduced pressure, to obtain the title compound as a white solid (28.1 g, 146 mmol). Acyl chloride was checked by quenching a sample in MeOH, LCMS showed methyl ester derivative. {[M+H]$^+$=152}

Example 1

(2S)-2-Methyl-1-[(6-methyl-3-pyridinyl)carbonyl]-4-{[4-(trifluoromethyl)phenyl]sulfonyl}piperazine

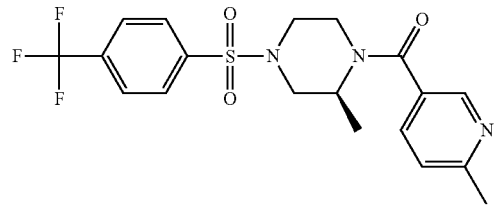

To a solution of (3S)-3-methyl-1-{[4-(trifluoromethyl)phenyl]sulfonyl}piperazine (Description 2) (100 mg, 0.324 mmol) in DMF (5 ml) was added DIPEA (0.170 ml, 0.973 mmol), HOBT.H$_2$O (49.7 mg, 0.324 mmol), HBTU (123 mg, 0.324 mmol) and 6-methyl-3-pyridinecarboxylic acid (44.5 mg, 0.324 mmol) and the reaction mixture was stirred overnight at room temperature. The reaction mixture was evaporated in vacuo, DCM (50 ml) was added and the solution was washed with NaHCO$_3$ (5 ml×2). The organic layer was dried with dried magnesium sulphate which was removed by filtration and the filtrate evaporated to dryness in vacuo. The residual oil was dissolved in 1:1 MeCN/DMSO (1.8 ml) and purified by MDAP in two batches. The fractions containing the desired product were combined and evaporated to dryness in vacuo. The residue was azeotroped with toluene to remove any remaining water to yield the title compound (86 mg).

m/z (API-ES) 428 [M+H]$^+$ $^1$H NMR (400 MHz, CHLOROFORM-d) δppm 1.42 (d, J=6.8 Hz, 3 H) 2.56-2.58 (m, 5 H) 3.28-3.47 (m, 1 H) 3.55-

3.64 (m, 1 H) 3.72-3.83 (m, 1 H) 3.82-4.93 (m, 2 H) 7.21 (d, J=8.0 Hz, 1 H) 7.58 (dd, J=8.0, 2.0 Hz, 1 H) 7.75-7.88 (m, 4 H) 8.44 (d, J=2.0 Hz, 1 H).

Example 2

(2S)-2-Methyl-1-[(2-methyl-3-pyridinyl)carbonyl]-4-{[4-(trifluoromethyl)phenyl]sulfonyl}piperazine hydrochloride

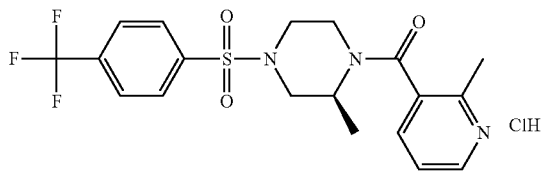

To a solution of (3S)-3-methyl-1-{[4-(trifluoromethyl)phenyl]sulfonyl}piperazine (Description 2) (100 mg, 0.324 mmol) in DMF (5 ml) was added 2-methyl-3-pyridinecarboxylic acid (44.5 mg, 0.324 mmol), HOBT.H₂O (49.7 mg, 0.324 mmol) and HATU (123 mg, 0.324 mmol). Finally DIPEA (0.170 ml, 0.973 mmol) was added and the reaction mixture was stirred at room temperature for 20 h. Solvent was removed by evaporation and MDAP purification yielded the title compound as the formate salt. The formate salt was suspended in saturated aqueous sodium bicarbonate and the free base extracted in to DCM. Evaporation yielded the free base as a light yellow oil. The oil was treated with 1M ethereal HCl to yield the title compound (118 mg) as a cream powder.

m/z (API-ES) 428 [M+H]$^+$ $^1$H NMR (400 MHz, CHLOROFORM-d) (NMR of free base; rotameric mixture) δ ppm 1.28-1.53 (m, 3 H), 1.98 (br. s., 1 H), 2.16-2.64 (m, 4 H), 3.17-3.33 (m, 1 H), 3.38-3.98 (m, 3 H), 4.61-4.75 (m, 0.5 H), 4.99-5.15 (m, 0.5 H), 7.10-7.23 (m, 1 H), 7.31-7.52 (m, 1 H), 7.84 (d, J=8.5 Hz, 2 H), 7.87 (d, J=8.5 Hz, 2 H), 8.47-8.59 (m, 1 H).

Alternative synthesis of (2S)-2-Methyl-1-[(2-methyl-3-pyridinyl)carbonyl]-4-{[4-(trifluoromethyl)phenyl]sulfonyl}piperazine Example 2a (3S)-3-methyl-1-{[4-(trifluoromethyl)phenyl]sulfonyl}piperazine (may be prepared as described in Description 2 or 2a) (30 g, 97 mmol) was dissolved in tetrahydrofuran (300 mL) before sodium hydroxide 3M (97 mL, 292 mmol) was added dropwise at 0° C. and the reaction stirred for 10 min. 2-methyl-3-pyridinecarbonyl chloride (may be prepared as described in Description 33) (26.2 g, 136 mmol) was added portionwise and the resulting mixture was stirred at room temperature for 10 min. The THF was removed from the mixture under reduced pressure and the resulting suspension was extracted with DCM (2×300 ml). The organic phase was washed with brine, dried over Na₂SO₄, filtered and concentrated to dryness to give the title compound (39.9 g).

m/z (API-ES) 428 [M+H]$^+$

NMR shows rotameric mixture:

$^1$H NMR (400 MHz, CDCl₃) δ ppm 1.33-1.50 (m, 3H), 2.20-2.62 (m, 5H), 3.27 (m, 1H), 3.45-3.97 (m, 3H), 4.70+ 5.10 (m, 1H), 7.17 (m, 1H), 7.39 (m, 1H), 7.85 (d, J=8.8 Hz, 2H), 7.89 (d, J=8.8 Hz, 2H), 8.56 (m, 1H).

Example 2b (2S)-2-methyl-1-[(2-methyl-3-pyridinyl)carbonyl]-4-{[4-(trifluoromethyl)phenyl]sulfonyl}piperazine (may be prepared as described in Example 2 or 2a) (39.9 g, 93 mmol) was dissolved in diethyl ether (500 ml). HCl 1.0M in ether (103 ml, 103 mmol) was added dropwise (a solid crashed out from the solution) and the mixture was stirred for 20 min. The white solid was recovered by filtration and dried under vacuum at 70° C. for 36 h to give the title compound (41.48 g) as the hydrochloride salt.

m/z (API-ES) 428 [M+H]$^+$

NMR shows rotameric mixture:

$^1$H NMR (400 MHz, DMSO) δ ppm 1.19-1.34 (m, 3H), 2.36-2.69 (m, 2H), 2.48 (s, 3H), 3.18-3.26 (m, 1H), 3.34-3.47 (m, 1H), 3.49-3.63 (m, 1H), 3.65-3.84 (m, 1H), 4.44+4.85 (m, 1H), 7.68 (m, 1H), 7.97 (d, J=8.4 Hz, 2H), 8.07 (d, J=8.4 Hz, 2H), 8.88-8.21 (m, 1H), 8.68-8.73 (m, 1H).

Example 3

1-(3-Pyridinylcarbonyl)-4-{[4-(trifluoromethyl)phenyl]sulfonyl}piperazine

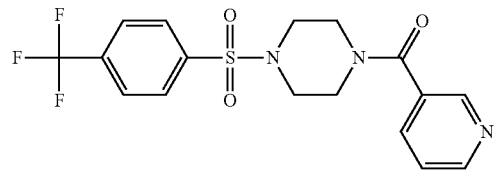

To a solution of 1-{[4-(trifluoromethyl)phenyl]sulfonyl}piperazine (Description 1) (100 mg, 0.340 mmol) in DMF (5 ml) was added HOBT.H₂O (52.0 mg, 0.340 mmol), HBTU (129 mg, 0.340 mmol), 3-pyridinecarboxylic acid (41.8 mg, 0.340 mmol) and DIPEA (0.178 ml, 1.019 mmol). The reaction mixture was stirred for 2 hours at room temperature. Reaction mixture was transferred to a 100 ml round bottom flask and was reduced to dryness in vacuo. The residue was dissolved in DCM (50 ml) and was transferred to a separating funnel then washed with saturated NaHCO₃ solution (5 ml), twice. The organic layer was collected and dried with dried magnesium sulphate. The solid was removed by filtration and the filtrate collected in a 250 ml round bottom flask and reduced to dryness in vacuo. The residue was then dissolved in 1.8 ml 1:1 MeCN/DMSO and purified by MDAP in 2 batches. The fractions containing desired product were combined in a 250 ml round bottom flask and reduced in vacuo to yield the title compound (63 mg).

m/z (API-ES) 400 [M+H]$^+$ $^1$H NMR (400 MHz, CHLOROFORM-d) δ ppm 3.11 (br. s., 4 H), 3.38-4.15 (m, 4 H), 7.37 (ddd, J=7.8, 4.9, 0.7 Hz, 1 H), 7.71 (dt, J=7.9, 1.93 Hz, 1 H), 7.80-7.95 (m, 4 H), 8.59 (d, J=1.5 Hz, 1H), 8.68 (dd, J=4.9, 1.6 Hz, 1H).

Example 4

1-[(6-Methyl-3-pyridinyl)carbonyl]-4-{[4-(trifluoromethyl)phenyl]sulfonyl}piperazine

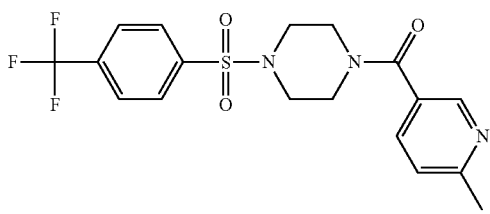

To a solution of 1-{[4-(trifluoromethyl)phenyl]sulfonyl}piperazine (Description 1) (100 mg, 0.340 mmol) in DMF (5 ml) was added HOBT.H$_2$O (52.0 mg, 0.340 mmol), HBTU (129 mg, 0.340 mmol), 6-methyl-3-pyridinecarboxylic acid (46.6 mg, 0.340 mmol) and DIPEA (0.18 ml, 1.02 mmol). The reaction mixture was stirred for 2 h at room temperature. Reaction mixture was transferred to a 100 ml round bottom flask and was reduced to dryness in vacuo. The residue was dissolved in DCM (50 ml) and was transferred to a separating funnel then washed with saturated NaHCO$_3$ solution (5 ml), twice. The organic layer was collected and dried with dried magnesium sulphate. The solid was removed by filtration and the filtrate collected in a 250 ml round bottom flask and reduced to dryness in vacuo. The residue was then dissolved in 1.8 ml 1:1 MeCN/DMSO and purified by MDAP in 2 batches. The fractions containing desired product were combined in a 250 ml round bottom flask and reduced in vacuo to yield the title compound (69 mg).

m/z (API-ES) 414 [M+H]$^+$ $^1$H NMR (400 MHz, CHLOROFORM-d) δ ppm 2.59 (s, 3 H), 3.09 (m, 4 H), 3.40-4.08 (m, 4 H), 7.21 (d, J=8.0 Hz, 1 H), 7.60 (dd, J=8.0, 2.0 Hz, 1 H), 7.83 (d, J=8.4 Hz, 2H), 7.89 (d, J=8.4 Hz, 2H), 8.47 (d, J=2.0 Hz, 1 H).

Example 5

1-[(2-Methyl-3-pyridinyl)carbonyl]-4-{[4-(trifluoromethyl)phenyl]sulfonyl}piperazine

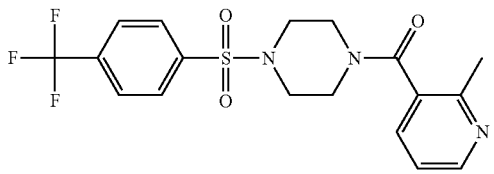

To a solution of 1-{[4-(trifluoromethyl)phenyl]sulfonyl}piperazine (Description 1) (100 mg, 0.340 mmol) in DMF (5 ml) was added HOBT.H$_2$O (52.0 mg, 0.340 mmol), HBTU (129 mg, 0.340 mmol), 2-methyl-3-pyridinecarboxylic acid (46.6 mg, 0.340 mmol) and DIPEA (0.178 ml, 1.019 mmol). The reaction mixture was stirred for 2 hours at room temperature.

Reaction mixture was transferred to a 100 ml round bottom flask and was reduced to dryness in vacuo. The residue was dissolved in DCM (50 ml) and transferred to a separating funnel then was washed with saturated NaHCO$_3$ solution (5 ml), twice. The organic layer was collected and dried with dried magnesium sulphate. The solid was removed by filtration and the filtrate collected in a 250 ml round bottom flask and reduced to dryness in vacuo.

The residue was then dissolved in 1.8 ml 1:1 MeCN/DMSO and purified by MDAP in 2 batches. The fractions containing desired product were combined in a 250 ml round bottom flask and reduced in vacuo to yield the title compound (107 mg).

m/z (API-ES) 414 [M+H]$^+$ $^1$H NMR (400 MHz, CHLOROFORM-d) δ ppm 2.45 (s, 3 H), 2.83-3.43 (m, 6 H), 3.75-4.12 (m, 2 H), 7.12-7.20 (m, 1 H), 7.41 (dd, J=8.0, 2.0 Hz, 1 H), 7.81-7.93 (M, 4 H), 8.55 (dd, J=5.0, 2.0 Hz, 1 H).

Example 6

4-{5-[(4-{[4-(Trifluoromethyl)phenyl]sulfonyl}-1-piperazinyl)carbonyl]-2-pyridinyl}morpholine

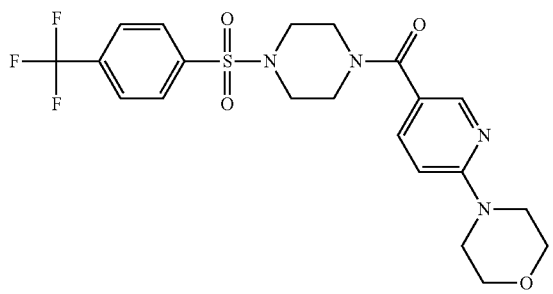

To a solution of 1-{[4-(trifluoromethyl)phenyl]sulfonyl}piperazine (Description 1) (80 mg, 0.272 mmol) in DMF (5 ml) were added 6-(4-morpholinyl)-3-pyridinecarboxylic acid (56.6 mg, 0.272 mmol), HOBT.H$_2$O (41.6 mg, 0.272 mmol), HBTU (103 mg, 0.272 mmol) and DIPEA (0.142 ml, 0.816 mmol) and the reaction mixture was stirred at room temperature for 2 h. The DMF was evaporated in vacuo then 5 ml of DCM were added and washed with saturated aqueous NaHCO$_3$ solution (5 ml), dried on a phase separation cartridge and evaporated in vacuo. The crude material was dissolved in MeCN/DMSO 1:1 and purified by MDAP. The desired fractions were collected and concentrated under vacuo giving the title compound (103 mg).

m/z (API-ES) 485 [M+H]$^+$ $^1$H NMR (400 MHz, CHLOROFORM-d) δppm 3.01-3.15 (m, 4 H), 3.53-3.62 (m, 4 H), 3.70-3.79 (m, 4 H), 3.79-3.85 (m, 4 H), 6.60 (d, J=8.9 Hz, 1 H), 7.58 (dd, J=8.9, 2.4 Hz, 1 H), 7.84 (d, J=8.3 Hz, 2 H), 7.89 (d, J=8.3 Hz, 2 H), 8.19 (d, J=2.4 Hz, 1 H).

Example 7

4-[5-({(3S)-4-[(4-Chlorophenyl)sulfonyl]-3-methyl-1-piperazinyl}carbonyl)-2-pyridinyl]morpholine

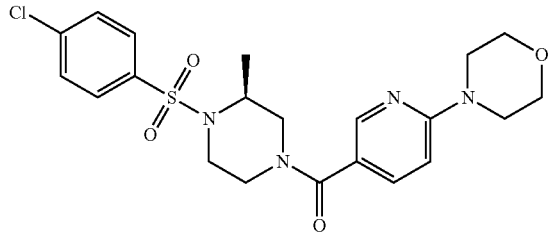

To a suspension of (2S)-1-[(4-chlorophenyl)sulfonyl]-2-methylpiperazine hydrochloride (Description 4) (105 mg, 0.338 mmol), EDC (71.3 mg, 0.372 mmol), HOBT.H$_2$O (56.9 mg, 0.372 mmol) and 6-(4-morpholinyl)-3-pyridinecarboxylic acid (77 mg, 0.372 mmol) in DCM (5 ml) was added N-ethyl morpholine (0.090 mL, 0.710 mmol). The reaction was stirred for 18 h at ambient temperature. To the reaction was added water (3 ml) and the organic layer collected via a hydrophobic frit. The organic layer was reduced in volume to approximately 2 ml then loaded onto a silica SP4 chromatography cartridge. The cartridge was eluted with a gradient from 60% ethyl acetate in iso-hexane to ethyl acetate then ethyl acetate. Fractions containing the desired product were combined and reduced in vacuo to yield the title compound as a white solid (88 mg).

m/z (API-ES) 465 [M+H]$^+$

Example 8

(2S)-1-[(4-Chlorophenyl)sulfonyl]-2-methyl-4-[(6-methyl-3-pyridinyl)carbonyl]piperazine

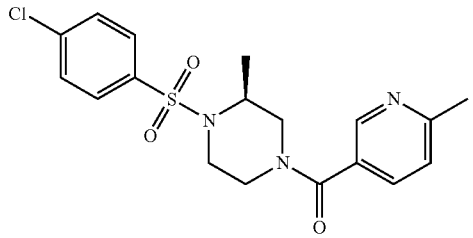

To a suspension of (2S)-1-[(4-chlorophenyl)sulfonyl]-2-methylpiperazine hydrochloride (Description 4) (105 mg, 0.338 mmol), EDC (71.2 mg, 0.371 mmol), HOBT.H$_2$O (56.9 mg, 0.371 mmol) and 6-methyl-3-pyridinecarboxylic acid (51.0 mg, 0.372 mmol) in DCM (5 ml) was added N-ethyl-morpholine (0.090 ml, 0.710 mmol). The reaction was stirred for 18 h at ambient temperature. To the reaction was added water (3 ml) and the organic layer collected via a hydrophobic frit. The organic layer was reduced in volume to approximately 2 ml then loaded onto a silica SP4 chromatography cartridge. The cartridge was eluted with ethyl acetate then a gradient from 0-10% (20% methanol in dichloromethane) in ethyl. Fractions containing the desired product were combined and reduced in vacuo to yield the title compound as a white solid (55 mg).

m/z (API-ES) 394 [M+H]$^+$ $^1$H NMR (400 MHz, CHLOROFORM-d) δ ppm 1.0 (br s, 3 H), 2.6 (s, 3 H), 3.2 (br s, 2 H), 3.7 (br s, 2 H), 4.0-4.8 (br m, 3 H), 7.2 (d, J=8.1 Hz, 1 H), 7.5 (m, 2 H), 7.6 (d, J=2.2 Hz, 1 H), 7.7 (m, 2 H), 8.5 (d, J=1.5 Hz, 1 H)

Example 9

(2R)-2-Methyl-4-[(6-methyl-3-pyridinyl)carbonyl]-1-{[4-(trifluoromethyl)phenyl]sulfonyl}piperazine formic acid salt

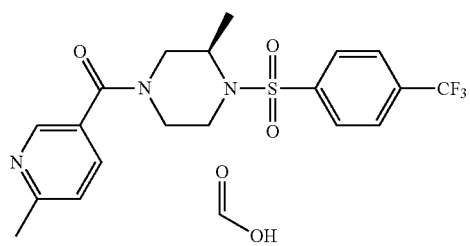

To a solution of 6-methyl-3-pyridinecarboxylic acid (47.7 mg, 0.348 mmol) in DCM (2.00 ml) was added HATU (132 mg, 0.348 mmol) and DIPEA (0.152 ml, 0.870 mmol) and the mixture stirred for 15 min before addition of (2R)-2-methyl-1-{[4-(trifluoromethyl)phenyl]sulfonyl}piperazine hydrochloride (Description 6) (100 mg, 0.290 mmol) in DMF (2 ml). The resultant mixture was stirred for 16 h at room temperature then the reaction mixture was concentrated and the residue taken up in DMSO and purified by MDAP. The collected fractions were concentrated in vacuo and triturated with isohexane giving the title compound (77.7 mg) as a white solid.

m/z (API-ES) 428 [M+H]$^+$ $^1$H NMR (400 MHz, DMSO-d$_6$) rotameric mixture δppm 0.74-1.17 (m, 3 H), 2.53 (s, 3 H), 2.73-3.09 (m, 1 H), 3.34-4.56 (m, 6 H), 7.42 (d, J=8.0 Hz, 1 H), 7.68-7.94 (m, 1 H), 7.95-8.10 (m, 4 H), 8.41-8.64 (m, 1 H).

Example 10

(2R)-2-Methyl-4-[(2-methyl-3-pyridinyl)carbonyl]-1-{[4-(trifluoromethyl)phenyl]sulfonyl}piperazine formic acid salt

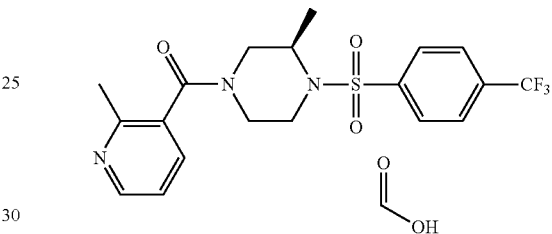

To a solution of 2-methyl-3-pyridinecarboxylic acid (47.7 mg, 0.348 mmol) in DCM (2.000 ml) was added HATU (132 mg, 0.348 mmol) and DIPEA (0.152 ml, 0.870 mmol) and the mixture stirred for 15 minutes before addition of (2R)-2-methyl-1-{[4-(trifluoromethyl)phenyl]sulfonyl}piperazine hydrochloride (Description 6) (100 mg, 0.290 mmol) in DMF (2 ml). The resultant mixture was stirred for 16 h at room temperature then the reaction mixture was then concentrated and the residue taken up in DMSO and purified by reverse phase MDAP. The collected fractions were concentrated in vacuo giving the the title compound (80.7 mg) as a white solid.

m/z (API-ES) 428 [M+H]$^+$ $^1$H NMR (400 MHz, DMSO-d$_6$) rotameric mixture δ ppm 0.79-1.10 (m, 3 H), 2.23-2.48 (m, 3 H), 2.80-2.96 (m, 1 H), 3.00-3.13 (m, 1 H), 3.19-3.33 (m, 1 H), 3.54-3.81 (m, 2 H), 3.97-4.49 (m, 2 H), 7.26-7.43 (m, 1 H), 7.60-7.87 (m, 1 H), 7.93-8.12 (m, 4 H), 8.55 (td, J=5.1, 1.4 Hz, 1 H).

Example 11

(2S)-2-Methyl-4-[(6-methyl-3-pyridinyl)carbonyl]-1-{[4-(trifluoromethyl)phenyl]sulfonyl}piperazine formic acid salt

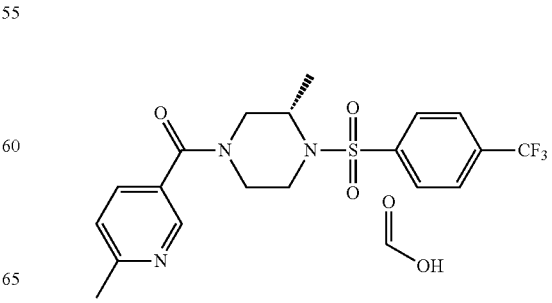

To a solution of (2S)-2-methyl-1-{[4-(trifluoromethyl)phenyl]sulfonyl}piperazine hydrochloride (Description 8) (100 mg, 0.270 mmol) in THF (5 ml) was added HOBT.H₂O (41.3 mg, 0.270 mmol), HBTU (102 mg, 0.270 mmol) and 6-methyl-3-pyridinecarboxylic acid (40.7 mg, 0.297 mmol). The mixture was stirred for 5 min before addition of DIPEA (0.118 ml, 0.674 mmol) and the resultant solution stirred at room temperature for 16 h. The mixture was then concentrated and the residue partitioned between DCM (10 ml) and water (10 ml), the layers were separated using a hydrophobic frit, the organic layers were then concentrated to dryness and the crude material dissolved in DMSO and purified by MDAP giving the title compound (100.2 mg) as a colourless oil which solidified on standing.

m/z (API-ES) 428 [M+H]⁺

¹H NMR (400 MHz, CHLOROFORM-d) δ ppm 1.04 (br. s., 3 H), 2.61 (s, 3 H), 2.85-3.41 (m, 4 H), 3.62-3.84 (m, 1 H), 3.91-4.92 (m, 2 H), 7.25 (d, J=8.0 Hz, 1 H), 7.65 (dd, J=8.0, 2.1 Hz, 1 H), 7.80 (d, J=8.2 Hz, 2 H), 7.94 (d, J=8.2 Hz, 2 H), 8.52 (s, 1 H).

Example 12

(2S)-2-Methyl-4-[(2-methyl-3-pyridinyl)carbonyl]-1-{[4-(trifluoromethyl)phenyl]sulfonyl}piperazine formic acid salt

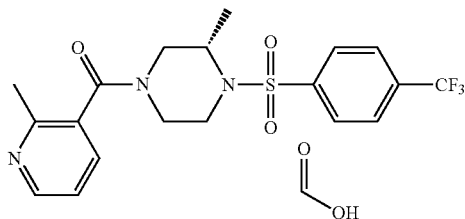

To a solution of (2S)-2-methyl-1-{[4-(trifluoromethyl)phenyl]sulfonyl}piperazine hydrochloride (Description 8) (100 mg, 0.270 mmol) in THF (5 ml) was added HOBT.H₂O (41.3 mg, 0.270 mmol), HBTU (102 mg, 0.270 mmol) and 2-methyl-3-pyridinecarboxylic acid (40.7 mg, 0.297 mmol). The mixture was stirred for 5 min before addition of DIPEA (0.118 ml, 0.674 mmol) and the resultant solution stirred at room temperature for 16 h. The mixture was then concentrated and the residue partitioned between DCM (10 ml) and water (10 ml), the layers were separated using a hydrophobic frit and the organic layers concentrated to dryness and the crude dissolved in DMSO and purified by MDAP giving the title compound (61.2 mg) as a white solid.

m/z (API-ES) 428 [M+H]⁺

¹H NMR (400 MHz, CHLOROFORM-d) rotameric mixture δppm 0.88-1.19 (m, 3 H), 2.41-2.62 (m, 3 H), 2.88-3.44 (m, 4 H), 3.58-3.88 (m, 1 H), 4.03-4.44 (m, 1 H), 4.51-4.87 (m, 1 H), 7.13-7.26 (m, 1 H), 7.35-7.60 (m, 1 H), 7.80 (d, J=8.3 Hz, 2 H), 7.93 (d, J=8.3 Hz, 2 H), 8.51-8.64 (m, 1 H).

Example 13

5-[((2S)-2-Methyl-4-{[4-(trifluoromethyl)phenyl]sulfonyl}-1-piperazinyl)carbonyl]-2-pyridinecarbonitrile

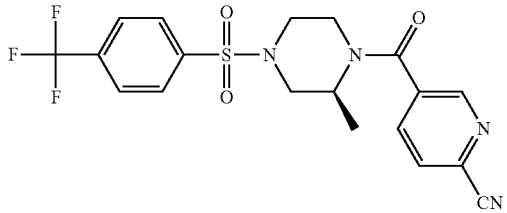

To a solution of (3S)-3-methyl-1-{[4-(trifluoromethyl)phenyl]sulfonyl}piperazine (Description 2) (100 mg, 0.324 mmol) in DMF (5 ml) was added HOBT.H₂O (49.7 mg, 0.324 mmol), HBTU (123 mg, 0.324 mmol), 6-cyano-3-pyridinecarboxylic acid (48.0 mg, 0.324 mmol) and DIPEA (0.170 ml, 0.973 mmol) and the reaction mixture was stirred for 1 h at room temperature. The reaction mixture was reduced in vacuo. The residue was dissolved in DCM (50 ml), transferred to a separating funnel and the solution was washed with NaHCO₃ (5 ml), twice. The organic layer was dried with magnesium sulphate which was removed by filtration and the filtrate evaporated to dryness in vacuo. The residual oil was dissolved in 1:1 MeCN/DMSO (1.8 ml) and purified by MDAP in two batches. The fractions containing the desired product were combined and evaporated to dryness in vacuo to yield the title compound (77 mg).

m/z (API-ES) 439 [M+H]⁺, 480 [M+H+41]⁺

Example 14

(2S)-2-Methyl-1-{[6-(methyloxy)-3-pyridinyl]carbonyl}-4-{[4-(trifluoromethyl)phenyl]sulfonyl}piperazine

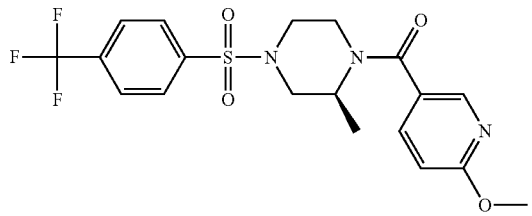

To a solution of (3S)-3-methyl-1-{[4-(trifluoromethyl)phenyl]sulfonyl}piperazine (Description 2) (100 mg, 0.324 mmol) in DMF (5 ml) was added HOBT.H₂O (49.7 mg, 0.324 mmol), HBTU (123 mg, 0.324 mmol), 6-(methyloxy)-3-pyridinecarboxylic acid (49.7 mg, 0.324 mmol) and DIPEA (0.170 ml, 0.973 mmol) and the reaction mixture was stirred for 1 h at room temperature. The reaction mixture was evaporated in vacuo. The residue was dissolved in DCM (50 ml), transferred to a separating funnel and the solution was washed with NaHCO₃ (5 ml), twice. The organic layer was dried with magnesium sulphate which was removed by filtration and the filtrate evaporated to dryness in vacuo. The residual oil was dissolved in 1:1 MeCN/DMSO (1.8 ml) and purified by MDAP in two batches. The fractions containing the desired product were combined and evaporated to dryness in vacuo to yield the title compound (85 mg).

m/z (API-ES) 444 [M+H]+

$^1$H NMR (400 MHz, CHLOROFORM-d) δ ppm 1.45 (d, J=6.8 Hz, 3 H) 2.29-2.41 (m, 1 H) 2.43-2.56 (m, 1 H) 3.34-3.49 (m, 1 H) 3.55-3.66 (m, 1 H) 3.75-3.85 (m, 1 H) 3.95 (s, 3 H) 4.01-4.25 (m, 1 H) 4.37-4.68 (m, 1 H) 6.76 (dd, J=8.6, 0.7 Hz, 1 H) 7.59 (dd, J=8.6, 2.4 Hz, 1 H) 7.78-7.91 (m, 4 H) 8.16 (d, J=2.4 Hz, 1 H)

Example 15

(2S)-2-Methyl-1-{[2-(methyloxy)-3-pyridinyl]carbonyl}-4-{[4-(trifluoromethyl)phenyl]sulfonyl}piperazine

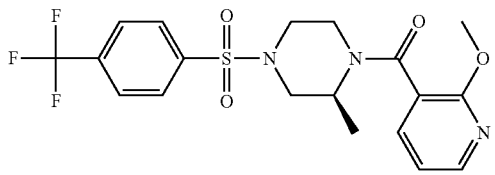

To a solution of (3S)-3-methyl-1-{[4-(trifluoromethyl)phenyl]sulfonyl}piperazine (Description 2) (100 mg, 0.324 mmol) in DMF (5 ml) was added HOBT.H$_2$O (49.7 mg, 0.324 mmol), HBTU (123 mg, 0.324 mmol), 2-(methyloxy)-3-pyridinecarboxylic acid (49.7 mg, 0.324 mmol) and DIPEA (0.170 ml, 0.973 mmol) and the reaction mixture was stirred for 1 h at room temperature. The reaction mixture was reduced in vacuo. The residue was dissolved in DCM (50 ml), transferred to a separating funnel and the solution was washed with NaHCO$_3$ (5 ml), twice. The organic layer was dried with magnesium sulphate which was removed by filtration and the filtrate evaporated to dryness in vacuo. The residual oil was dissolved in 1:1 MeCN/DMSO (1.8 ml) and purified by MDAP in two batches. The fractions containing the desired product were combined and evaporated to dryness in vacuo to yield the title compound (95 mg).

m/z (API-ES) 443 [M+H]+

$^1$H NMR (400 MHz, CHLOROFORM-d) Rotameric mixture δ ppm 1.23-1.55 (m, 3 H), 2.06-2.79 (m, 2 H), 3.05-4.21 (m, 7 H), 4.53+5.14 (m, 1 H), 6.93 (br. s., 1 H), 7.36-7.63 (m, 1 H), 7.69-7.95 (m, 4 H), 8.20 (d, J=4.8 Hz, 1 H).

Example 16

(2S)-2-Methyl-1-[(5-methyl-3-pyridinyl)carbonyl]-4-{[4-(trifluoromethyl)phenyl]sulfonyl}piperazine

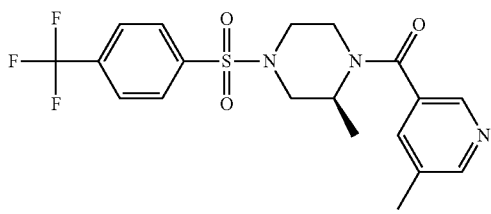

To a solution of (3S)-3-methyl-1-{[4-(trifluoromethyl)phenyl]sulfonyl}piperazine (Description 2) (100 mg, 0.324 mmol) in DMF (5 ml) was added HOBT.H$_2$O (49.7 mg, 0.324 mmol), HBTU (123 mg, 0.324 mmol), 5-methyl-3-pyridinecarboxylic acid (44.5 mg, 0.324 mmol) and DIPEA (0.170 ml, 0.973 mmol) and the reaction mixture was stirred for 1 h at room temperature. The reaction mixture was evaporated in vacuo. The residue was dissolved in DCM (50 ml), transferred to a separating funnel and the solution was washed with aqueous NaHCO$_3$ (5 ml), twice. The organic layer was dried with magnesium sulphate which was removed by filtration and the filtrate evaporated to dryness in vacuo. The residual oil was dissolved in 1:1 MeCN/DMSO (1.8 ml) and purified by MDAP in two batches. The fractions containing the desired product were combined and evaporated to dryness in vacuo to the title compound (95 mg).

m/z (API-ES) 428 [M+H]+

$^1$H NMR (400 MHz, CHLOROFORM-d) δ ppm 1.45 (d, J=6.9 Hz, 3 H), 2.34 (m, 1H), 2.37 (s, 3H), 2.51 (m, 1H), 3.2-5.0 (m, 5 H), 7.50 (s, 1 H), 7.84 (d, J=8.4 Hz, 2H), 7.88 (d, J=8.4 Hz, 2H), 8.35 (d, J=1.6 Hz, 1 H), 8.50 (d, J=1.6 Hz, 1 H).

Example 17

3-Methyl-4-({(3S)-3-methyl-4-[(6-methyl-3-pyridinyl)carbonyl]-1-piperazinyl}sulfonyl)benzonitrile

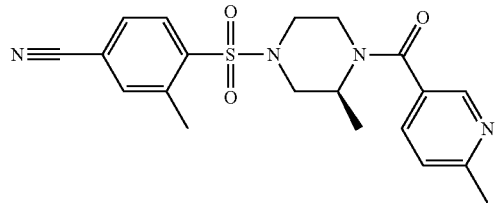

To a solution of 3-methyl-4-{[(3S)-3-methyl-1-piperazinyl]sulfonyl}benzonitrile (Description 11) (75 mg, 0.268 mmol), 6-methyl-3-pyridinecarboxylic acid (40.5 mg, 0.295 mmol) and DIPEA (0.070 ml, 0.403 mmol) in dry DMF (3 ml) at room temperature under Ar was added HATU (122 mg, 0.322 mmol) and the resulting yellow solution stirred at room temperature for 1 h. Concentration in vacuo gave a yellow oil, that was purified by MDAP purification; concentration of the desired fractions gave a clear film (78.8 mg). Flash chromatography (silica; Flash 12S; linear gradient (1-8%) [2M NH$_3$ in MeOH] in DCM) gave the title compound as a clear film (54.5 mg) that became a white solid on standing in vacuo (1 mbar) for 1 hour.

m/z (API-ES) 399 [M+H]+

$^1$H NMR (400 MHz, CHLOROFORM-d) δ ppm 1.36 (d, J=6.8 Hz, 3 H), 2.59 (s, 3 H), 2.67 (s, 3 H), 2.72 (td, J=11.8, 3.2 Hz, 1 H), 2.90 (dd, J=12.3, 3.2 Hz, 1 H), 3.28-3.43 (m, 1 H), 3.58 (d, J=12.2 Hz, 1 H), 3.72 (d, J=11.7 Hz, 1 H), 3.88-4.82 (m, 2 H), 7.22 (d, J=7.9 Hz, 1 H), 7.60 (dd, J=8.0, 2.3 Hz, 1 H), 7.62-7.66 (m, 2 H), 7.95 (d, J=8.7 Hz, 1 H), 8.49 (d, J=1.7 Hz, 1 H).

Example 18

(2S)-2-Methyl-1-[(4-methyl-3-pyridinyl)carbonyl]-4-{[4-(trifluoromethyl)phenyl]sulfonyl}piperazine

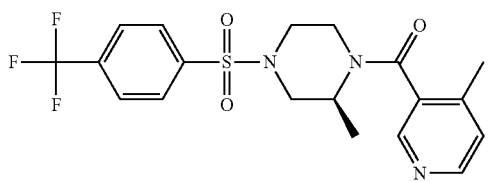

To a solution of (3S)-3-methyl-1-{[4-(trifluoromethyl)phenyl]sulfonyl}piperazine (Description 2) (100 mg, 0.324 mmol) in DMF (5 ml) was added HOBT.H₂O (49.7 mg, 0.324 mmol), HBTU (123 mg, 0.324 mmol), 4-methyl-3-pyridinecarboxylic acid (44.5 mg, 0.324 mmol) and DIPEA (0.170 ml, 0.973 mmol) and the reaction mixture was stirred for 1 h at room temperature. The reaction mixture was reduced in vacuo. The residue was dissolved in DCM (50 ml), transferred to a separating funnel and the solution was washed with aqueous NaHCO₃ (5 ml), twice. The organic layer was dried with dried magnesium sulphate which was removed by filtration and the filtrate evaporated to dryness in vacuo. The residual oil was dissolved in 1:1 MeCN/DMSO (1.8 ml) and purified by MDAP in two batches. The fractions containing the desired product were combined and evaporated to dryness in vacuo. The residue was then dissolved in diethyl ether (50 ml) and transferred to a 100 ml round bottom flask and reduced to dryness in vacuo to yield the title compound (67 mg).

m/z (API-ES) 428 [M+H]⁺

¹H NMR (400 MHz, CHLOROFORM-d) (rotameric mixture) δ ppm 1.26-1.52 (m, 3 H), 2.60-2.64 (m, 10H), 7.43-7.62 (m, 1 H), 7.87 (d, J=6.5 Hz, 4 H), 8.44-8.66 (m, 2 H).

Example 19

(2R)-2-methyl-1-[(6-methyl-3-pyridinyl)carbonyl]-4-{[4-(trifluoromethyl)phenyl]sulfonyl}piperazine formic acid salt (1:1)

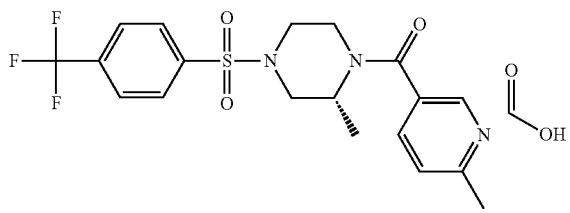

To a solution of (3R)-3-methyl-1-{[4-(trifluoromethyl)phenyl]sulfonyl}piperazine (Description 12) (80 mg, 0.259 mmol) in DMF (4 ml) was added 6-methyl-3-pyridinecarboxylic acid (35.6 mg, 0.259 mmol), HOBT.H₂O (39.7 mg, 0.259 mmol), HBTU (98 mg, 0.259 mmol) and DIPEA (0.136 ml, 0.778 mmol) and the reaction mixture was stirred at room temperature for 1 h. The DMF was evaporated in vacuo then 5 ml of DCM were added and washed with saturated NaHCO₃ solution (5 ml), dried on a phase separation cartridge and evaporated in vacuo. The crude material was dissolved in MeCN/DMSO 1:1 and purified by MDAP to give the title compound (93 mg).

m/z (API-ES) 428 [M+H]⁺

¹H NMR (400 MHz, CHLOROFORM-d) δ ppm 1.45 (d, J=6.9 Hz, 3 H) 2.37 (td, J=11.9, 2.9 Hz, 1 H) 2.52 (dd, J=11.4, 2.4 Hz, 1 H) 2.61 (s, 3 H) 3.33-3.49 (m, 1 H) 3.62 (d, J=11.8 Hz, 1 H) 3.75-3.87 (m, 1 H) 4.00-4.90 (m, 2 H) 7.25 (s, 1 H) 7.65 (dd, J=8.0, 2.2 Hz, 1 H) 7.80-7.91 (m, 4 H) 8.47 (d, J=1.8 Hz, 1 H)

Example 20

(2R)-2-methyl-1-[(2-methyl-3-pyridinyl)carbonyl]-4-{[4-(trifluoromethyl)phenyl]sulfonyl}piperazine formic acid salt (1:1)

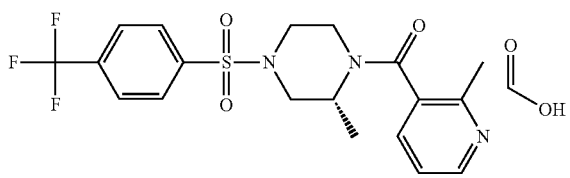

To a solution of (3R)-3-methyl-1-{[4-(trifluoromethyl)phenyl]sulfonyl}piperazine (Description 12) (80 mg, 0.259 mmol) in DMF (4 ml) was added 2-methyl-3-pyridinecarboxylic acid (35.6 mg, 0.259 mmol), HOBT.H₂O (39.7 mg, 0.259 mmol), HBTU (98 mg, 0.259 mmol) and DIPEA (0.136 ml, 0.778 mmol) and the reaction mixture was stirred at room temperature for 1 h. The DMF was evaporated under vacuum, 5 ml of DCM added and then washed with saturated NaHCO₃ solution (5 ml), dried on a phase separation cartridge and evaporated under vacuo. The crude material was dissolved in MeCN/DMSO 1:1 and purified by MDAP to give the title compound (75 mg).

m/z (API-ES) 428 [M+H]⁺

¹H NMR (400 MHz, CHLOROFORM-d) (rotameric mixture) δ ppm 1.28-1.41 (m, 1.5 H), 1.41-1.55 (m, 1.5 H), 2.19-2.34 (m, 1 H), 2.37-2.51 (m, 3 H), 2.51-2.66 (m, 1 H), 3.17-3.36 (m, 1 H), 3.38-3.62 (m, 1 H), 3.62-3.85 (m, 1.5 H), 3.85-4.01 (m, 0.5 H), 4.61-4.76 (m, 0.5 H), 5.01-5.16 (m, 0.5 H), 7.13-7.26 (m, 1 H), 7.34-7.59 (m, 1 H), 7.79-7.93 (m, 4 H), 8.54 (d, J=3.5 Hz, 1 H).

Example 21

(2S)-2-Methyl-1-[(6-methyl-3-pyridinyl)carbonyl]-4-({4-[(trifluoromethyl)oxy]phenyl}sulfonyl)piperazine

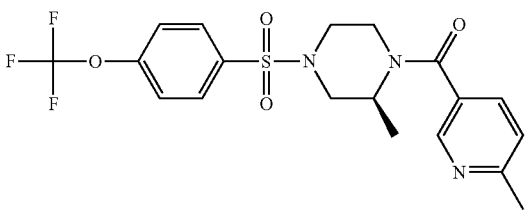

To a solution of (2S)-2-methyl-1-[(6-methyl-3-pyridinyl)carbonyl]piperazine (Description 13) (100 mg, 0.456 mmol) in DMF (10 ml) was added 4-[(trifluoromethyl)oxy]benzenesulfonyl chloride (143 mg, 0.547 mmol). Finally DIPEA (0.239 ml, 1.368 mmol) was added and the reaction mixture was stirred at room temperature for 20 h. Solvent was removed by evaporation, the residue was dissolved in ethyl acetate and the solution extracted with saturated aqueous NaHCO$_3$. The organic layer was dried over MgSO$_4$, filtered and evaporated to dryness and the residue was purified by MDAP to yield the title compound (32 mg) as a white powder.

m/z (API-ES) 444 [M+H]$^+$ $^1$H NMR (400 MHz, CHLOROFORM-d) δ ppm 1.45 (d, J=6.8 Hz, 3 H) 2.15-4.94 (m, 7 H) 2.65 (s, 3 H) 7.31 (d, J=8.0 Hz, 1 H) 7.39 (dd, J=8.8, 0.8 Hz, 2 H) 7.71 (dd, J=8.0, 2.2 Hz, 1 H) 7.76-7.83 (m, 2 H) 8.56 (d, J=1.8 Hz, 1 H)

Example 22

(2S)-4-({4-[(Difluoromethyl)oxy]phenyl}sulfonyl)-2-methyl-1-[(6-methyl-3-pyridinyl)carbonyl]piperazine

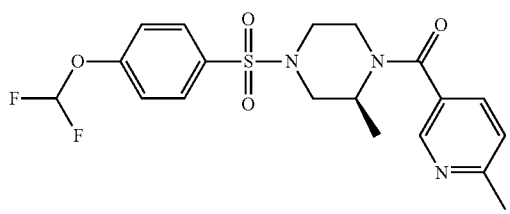

To a solution of (2S)-2-methyl-1-[(6-methyl-3-pyridinyl)carbonyl]piperazine (Description 13) (100 mg, 0.456 mmol) in DMF (10 ml) was added 4-[(difluoromethyl)oxy]benzenesulfonyl chloride (133 mg, 0.547 mmol). Finally DIPEA (0.239 ml, 1.368 mmol) was added and the reaction mixture was stirred at room temperature for 20 h. Solvent was removed by evaporation, the residue was dissolved in ethyl acetate and the solution washed with saturated aqueous NaHCO$_3$. The organic layer was dried over MgSO$_4$, filtered and evaporated to dryness and the residue was purified by MDAP to yield the title compound (72 mg) as a white powder.

m/z (API-ES) 426 [M+H]$^+$.

1H NMR (400 MHz, CHLOROFORM-d) δ ppm 1.43 (d, J=6.8 Hz, 3 H) 2.12-4.80 (m, 7 H) 2.60 (s, 3 H) 6.63 (t, J=72.2 Hz, 1 H) 7.23 (d, J=8.0 Hz, 1 H) 7.25-7.33 (m, 2 H) 7.61 (dd, J=8.0, 2.3 Hz, 1 H) 7.71-7.79 (m, 2 H) 8.48 (d, J=1.8 Hz, 1 H)

Example 23

1-[(6-Methyl-3-pyridinyl)carbonyl]-4-({4-[(trifluoromethyl)oxy]phenyl}sulfonyl)piperazine

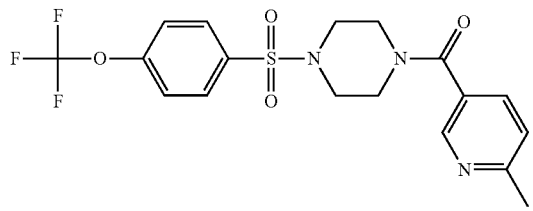

To a solution of 1-[(6-methyl-3-pyridinyl)carbonyl]piperazine (may be prepared as described in Description 14) (100 mg, 0.487 mmol) in DMF (10 ml) was added 4-[(trifluoromethyl)oxy]benzenesulfonyl chloride (152 mg, 0.585 mmol). Finally DIPEA (0.255 ml, 1.462 mmol) was added and the reaction mixture was stirred at room temperature for 20 h. Solvent was removed by evaporation, the residue was dissolved in ethyl acetate and the solution extracted with saturated aqueous NaHCO$_3$. The organic layer was dried over MgSO$_4$, filtered and evaporated to dryness and the residue was purified by MDAP to yield the title compound (42 mg) as a white powder.

m/z (API-ES) 430 [M+H]$^+$

1H NMR (400 MHz, CHLOROFORM-d) δ ppm 2.63 (s, 3 H) 2.91-4.10 (m, 8 H) 7.25-7.30 (m, 1 H) 7.40 (dd, J=8.9, 0.85 Hz, 2 H) 7.69 (dd, J=8.0, 2.3 Hz, 1 H) 7.78-7.84 (m, 2 H) 8.54 (d, J=1.8 Hz, 1 H).

Example 24

(2S)-1-[(6-Chloro-2-methyl-3-pyridinyl)carbonyl]-2-methyl-4-{[4-(trifluoromethyl)phenyl]sulfonyl}piperazine

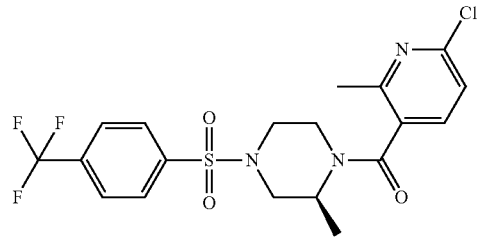

HATU (460 mg, 1.21 mmol) was added to a solution of 6-chloro-2-methyl-3-pyridinecarboxylic acid (commercially available, e.g. from Anichem, or may be prepared according to known methods) (173 mg, 1.01 mmol) in DMF (4 ml) and the mixture was treated with DIPEA (0.440 ml, 2.52 mmol). This mixture was stirred for ca. 10 min at ambient temperature. (3S)-3-Methyl-1-{[4-(trifluoromethyl)phenyl]sulfonyl}piperazine (may be prepared as described in Description 2) (371 mg, 1.20 mmol) was then added and stirring was continued for one hour. The reaction mixture was partitioned between DCM and sat aq. NaHCO$_3$ solution (20 ml each). The layers were separated and the aqueous was washed with further DCM (2×20 ml). The combined organic layers were concentrated to leave a dark brown gum. Purification by silica chromatography (Biotage SP4, 25S cartridge), eluting with 12-100% ethyl acetate in isohexane, gave the title compound (456 mg) as a pale yellow gum.

m/z (API-ES) 462/464 [M+H]$^+$ (Cl isotopes)

Example 25

4-({(3S)-4-[(6-Chloro-2-methyl-3-pyridinyl)carbonyl]-3-methyl-1-piperazinyl}sulfonyl)-3-methylbenzonitrile

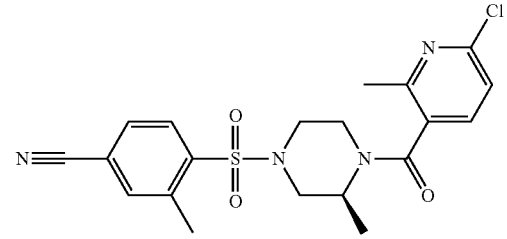

HATU (425 mg, 1.12 mmol) was added to a solution of 6-chloro-2-methyl-3-pyridinecarboxylic acid (commercially available, e.g. from Anichem, or may be prepared according to known methods) (160 mg, 0.93 mmol) in DMF (3 ml) and the mixture was treated with DIPEA (0.407 ml, 2.33 mmol). This mixture was stirred for ca. 10 min at ambient temperature. 3-Methyl-4-{[(3S)-3-methyl-1-piperazinyl]sulfonyl}benzonitrile (may be prepared as described in Description 11) (313 mg, 1.12 mmol) was added as a solution in DMF (2 ml) and stirring was continued for ca. 1 hour. The reaction mixture was partitioned between DCM and sat aq. NaHCO₃ solution (20 ml each). The layers were separated and the aqueous was washed with further DCM (2×20 ml). The combined organic layers were dried (hydrophobic frit) and concentrated to leave a dark brown gum. Purification by silica chromatography (Biotage SP4, 25S cartridge), eluting with 12-100% ethyl acetate in isohexane, gave the title compound as a pale cream foam (376 mg).

m/z (API-ES) 433/435 [M+H]⁺ (Cl isotopes)

Example 26

(2S)-1-[(6-Chloro-3-pyridinyl)carbonyl]-2-methyl-4-{[4-(trifluoromethyl)phenyl]sulfonyl}piperazine

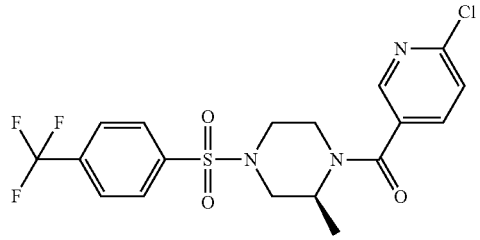

HATU (458 mg, 1.21 mmol) was added to a solution of 6-chloro-3-pyridinecarboxylic acid (supplied by Aldrich) (174 mg, 1.10 mmol) in DMF (4 ml) and the mixture was treated with DIPEA (0.437 ml, 2.50 mmol). This mixture was stirred for ca. 10 min at ambient temperature. (3S)-3-Methyl-1-{[4-(trifluoromethyl)phenyl]sulfonyl}piperazine (may be prepared as described in Description 2) (308 mg, 1.0 mmol) was added and stirring was continued for 1.25 h. The reaction mixture was partitioned between DCM and saturated aqueous NaHCO₃ solution (20 ml each). The layers were separated and the aqueous layer was washed with further DCM (2×20 ml). The combined organic layers were concentrated to leave a dark brown gum. Purification by silica chromatography (Biotage SP4, 25S cartridge), eluting with 12-100% ethyl acetate in pentane, gave the title compound (439 mg) as a pale yellow gum.

m/z (API-ES) 448/450 [M+H]⁺ (Cl isotopes)

Example 27

(2S)-1-[(6-Fluoro-4-methyl-3-pyridinyl)carbonyl]-2-methyl-4-{[4-(trifluoromethyl)phenyl]sulfonyl}piperazine

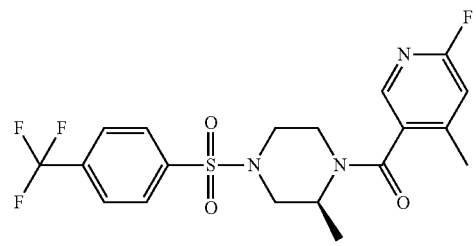

HATU (440 mg, 1.16 mmol) was added to a solution of 6-fluoro-4-methyl-3-pyridinecarboxylic acid (supplied by Frontior Scientific) (150 mg, 0.97 mmol) in DMF (4 ml) and the mixture was treated with DIPEA (0.422 ml, 2.42 mmol). This mixture was stirred for ca. 10 min at ambient temperature. (3S)-3-Methyl-1-{[4-(trifluoromethyl)phenyl]sulfonyl}piperazine (may be prepared as described in Description 2) (358 mg, 1.16 mmol) was added and stirring was continued for 1.25 h. The reaction mixture was partitioned between DCM and saturated aqueous NaHCO₃ solution (20 ml each). The layers were separated and the aqueous was washed with further DCM (2×20 ml). The combined organic layers were concentrated to leave a dark brown gum. Purification by silica chromatography (Biotage SP4, 25S cartridge), eluting with 12-100% ethyl acetate in hexanes, gave the title compound (432 mg) as a yellow gum.

m/z (API-ES) 446 [M+H]⁺

Example 28

(2S)-1-[(5-Bromo-3-pyridinyl)carbonyl]-2-methyl-4-{[4-(trifluoromethyl)phenyl]sulfonyl}piperazine

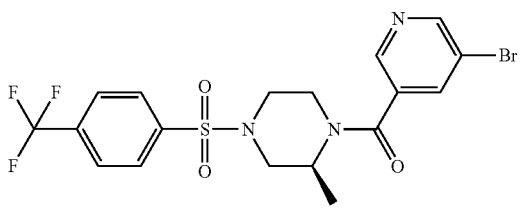

HATU (458 mg, 1.21 mmol) was added to a solution of 5-bromo-3-pyridinecarboxylic acid (supplied by Aldrich) (203 mg, 1.01 mmol) in DMF (4 ml) and the mixture was treated with DIPEA (0.438 ml, 2.51 mmol). This mixture was stirred for ca. 10 min at ambient temperature. (3S)-3-Methyl-1-{[4-(trifluoromethyl)phenyl]sulfonyl}piperazine (may be prepared as described in Description 2) (372 mg, 1.21 mmol) was added and stirring was continued for 1.5 h. The reaction mixture was partitioned between DCM and sat aq. NaHCO₃ solution (20 ml each). The layers were separated and the aqueous was washed with further DCM (2×20 ml). The combined organic layers were concentrated to leave an dark brown gum.

Purification by silica chromatography (Biotage SP4, 25S cartridge), eluting with 12-100 % ethyl acetate in isohexane, gave the title compound (496 mg) as a yellow gum, which became a yellow foam when dried in vacuo.

m/z (API-ES) 492/494 [M+H]⁺ (Br isotopes)

Example 29

(2S)-1-[(2,6-Dimethyl-3-pyridinyl)carbonyl]-2-methyl-4-{[4-(trifluoromethyl)phenyl]sulfonyl}piperazine

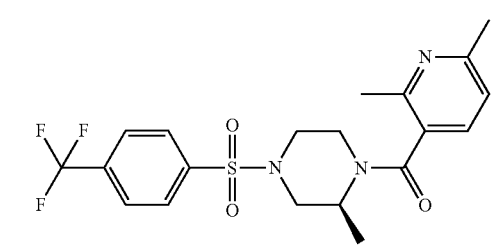

2,6-Dimethyl-3-pyridinecarboxylic acid (GSK1770624A, Atlantic) (98 mg, 0.65 mmol) and HATU (247 mg, 0.65 mmol) were suspended in DMF (2 ml) and DIPEA (0.170 ml, 0.97 mmol) was added. This mixture was stirred for 40 min at ambient temperature. (3S)-3-Methyl-1-{[4-(trifluoromethyl) phenyl]sulfonyl}piperazine (may be prepared as described in Description 2) (100 mg, 0.32 mmol) was added and stirring continued for 3 h. The reaction mixture was partitioned between DCM and sat aq. NaHCO₃ solution (10 ml each). The layers were separated and the aqueous was washed with further DCM (2×5 ml). The combined organic layers were concentrated to leave a brown oil. This was purified by MDAP to give the title compound (92 mg) as an orange solid.

m/z (API-ES) 442 [M+H]⁺

Example 30

4-[((3S)-4-{[6-(Dimethylamino)-2-methyl-3-pyridinyl]carbonyl}-3-methyl-1-piperazinyl)sulfonyl]-3-methylbenzonitrile hydrochloride

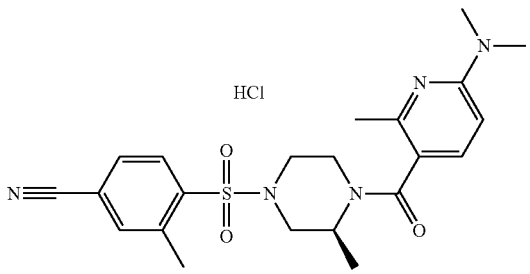

4-({(3S)-4-[(6-Chloro-2-methyl-3-pyridinyl)carbonyl]-3-methyl-1-piperazinyl}sulfonyl)-3-methylbenzonitrile (may be prepared as described in Example 25) (60 mg, 0.14 mmol) was weighed into a microwave vial, and suspended in isopropanol (1 ml). Dimethylamine, 2M in methanol (0.7 ml, 1.4 mmol) was added and the mixture was heated in the microwave to 100° C. for 30 min with stirring. LCMS analysis showed incomplete reaction (~13% conversion). The mixture was treated with further dimethylamine, 2M in methanol (0.35 ml, 0.7 mmol) and heated with stirring in the microwave at 100° C. for 6 h, after which LCMS analysis indicated >50% conversion. The reaction mixture was concentrated to give the crude material as a yellow gum which was purified by MDAP to give the free base of the product as a colourless gum (25 mg).

m/z (API-ES) 442 [M+H]⁺

The material was dissolved in THF (0.5 ml), treated with ethereal HCl (0.5 ml) and reconcentrated. The resulting colourless gum was triturated with ether, then dried, to give the title compound (17.6 mg) as a colourless solid m/z (API-ES) 442 [M+H]⁺

Example 31

N,N,6-Trimethyl-5-[((2S)-2-methyl-4-{[4-(trifluoromethyl)phenyl]sulfonyl}-1-piperazinyl)carbonyl]-2-pyridinamine hydrochloride

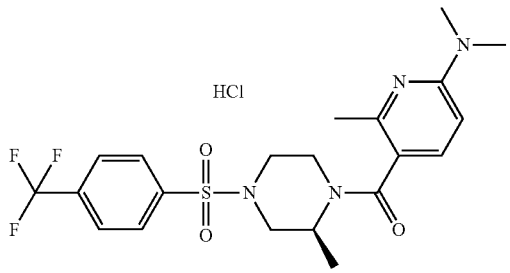

(2S)-1-[(6-Chloro-2-methyl-3-pyridinyl)carbonyl]-2-methyl-4-{[4-(trifluoromethyl)phenyl]sulfonyl}piperazine (may be prepared as described in Example 24) (65 mg, 0.14 mmol) was weighed into a microwave vial, and suspended in isopropanol (0.7 ml). Dimethylamine, 2M in methanol (0.7 ml, 1.40 mmol) was added, and the mixture was stirred briefly to give a clear solution. This was heated in the microwave to 120° C. for 4 h with stirring. The reaction mixture was concentrated to give the crude material as a yellow gum, which was purified by MDAP to give the free base of the title compound as a colourless gum (47 mg).

m/z (API-ES) 471 [M+H]⁺

¹H NMR (400 MHz, CHLOROFORM-d) δ ppm 1.37 (br s, 3 H), 2.23-2.35 (m, 4 H), 2.42-2.53 (m, 1 H), 3.08 (s, 6 H), 3.24-3.50 (m, 1 H), 3.54-3.66 (m, 1 H), 3.68-3.84 (m, 1 H), 4.0-4.5 (v br, 1 H), 4.8-5.2 (v br, 1 H), 6.29 (d, J=8.5 Hz, 1 H), 7.14 (d, J=8.5 Hz, 1 H), 7.80-7.89 (m, 4 H).

The material was dissolved in THF (0.5 ml) and treated with ethereal HCl (0.5 ml) and reconcentrated. The resulting colourless gum was triturated with ether, then dried, to give the title compound (37.6 mg) as a colourless solid.

m/z (API-ES) 471 [M+H]⁺

¹H NMR (400MHz, DMSO-d₆) δ ppm 1.23 (br s, 3 H), 2.30 (br s, 3 H), 2.33-2.46 (m, 1 H), 2.50-2.59 (m, 1 H), 3.14 (s, 6 H), 3.0-4.0 (m, obscured by water, 3 H), 4.2-4.5 (v br, 1 H), 4.6-4.9 (v br, 1 H), 6.82 (br s, 1 H), 7.59 (br s, 1 H), 7.95 (d, J=8.5 Hz, 2 H), 8.06 (d, J=8.5 Hz, 2 H).

Example 32

N,N-Diethyl-6-methyl-5-[((2S)-2-methyl-4-{[4-(trifluoromethyl)phenyl]sulfonyl}-1-piperazinyl)carbonyl]-2-pyridinamine hydrochloride

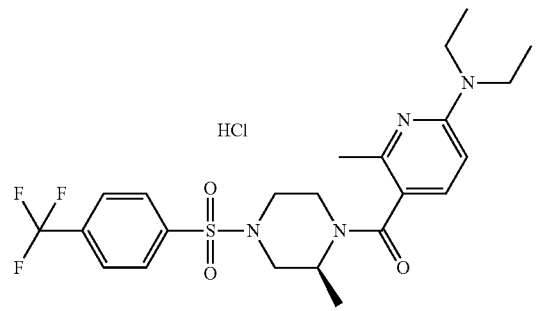

(2S)-1-[(6-Chloro-2-methyl-3-pyridinyl)carbonyl]-2-methyl-4-{[4-(trifluoromethyl)phenyl]sulfonyl}piperazine (may be prepared as described in Example 24) (55 mg, 0.12 mmol) was weighed into a microwave vial, and suspended in isopropanol (1.2 ml). The diethylamine (0.124 ml, 1.19 mmol) was added and the clear solution was heated in the microwave to 120° C. for 5 h with stirring. LCMS analysis showed very poor conversion (~5%). Further diethylamine (0.25 ml, 2.39 mmol) was added, the vial was resealed and was heated with stirring to 140° C. in the microwave for 5 h, after which LCMS analysis showed ~24% conversion. Further diethylamine (0.25 ml, 2.39 mmol) was added, the vial was resealed and was heated with stirring to 140° C. in the microwave for 15 h, giving ca. 65% conversion by LCMS analysis. The reaction mixture was concentrated to give a dark gum (68 mg). This was purified by MDAP to give the free base of the title compound as a colourless gum (26 mg).

m/z (API-ES) 499 [M+H]⁺

The material was dissolved in THF (0.5 ml) and treated with ethereal HCl (0.5 ml) and reconcentrated. The resulting colourless gum was triturated with ether, then dried, to give the title compound (19 mg) as a colourless solid.

m/z (API-ES) 499 [M+H]⁺

Example 33

4-[((3S)-4-{[6-(Diethylamino)-2-methyl-3-pyridinyl]carbonyl}-3-methyl-1-piperazinyl)sulfonyl]-3-methylbenzonitrile hydrochloride

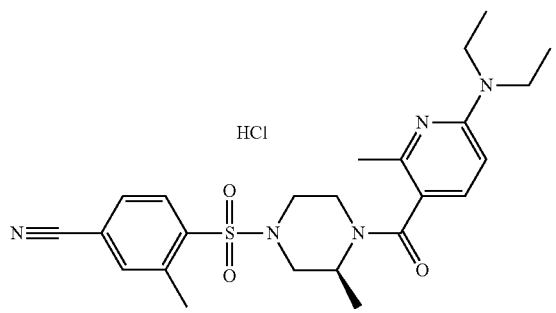

4-({(3S)-4-[(6-Chloro-2-methyl-3-pyridinyl)carbonyl]-3-methyl-1-piperazinyl}sulfonyl)-3-methylbenzonitrile (may be prepared as described in Example 25) (49 mg, 0.11 mmol) was weighed into a microwave vial, and suspended in isopropanol (1.1 ml). Diethylamine (0.237 ml, 2.26 mmol) was added and the mixture was heated in the microwave to 140° C. for 15 h with stirring. LCMS analysis showed ~34% conversion. The reaction was treated with further diethylamine (0.237 ml, 2.26 mmol), and returned to the microwave at 140° C., set for 18 h. However, the microwave stopped during this run after an unknown reaction time, and LCMS analysis showed little additional conversion. Further diethylamine (0.118 ml, 1.13 mmol) was added and the reaction was again heated with stirring in the microwave at 140° C. for 16.5 h. LCMS analysis now showed ~65% conversion.

The reaction mixture was concentrated to give the crude material as a dark brown gum (68 mg). This was purified by MDAP to give the free base of the title compound as a pale brown gum (26 mg).

m/z (API-ES) 470 [M+H]$^+$

The material was dissolved in THF (0.5 ml) and treated with ethereal HCl (0.5 ml) and reconcentrated. The resulting colourless gum was triturated with ether, then dried, to give the title compound (24 mg) as a pale brown solid.

m/z (API-ES) 470 [M+H]$^+$

Example 34

4-{6-Methyl-5-[((2S)-2-methyl-4-{[4-(trifluoromethyl)phenyl]sulfonyl}-1-piperazinyl)carbonyl]-2-pyridinyl}morpholine hydrochloride

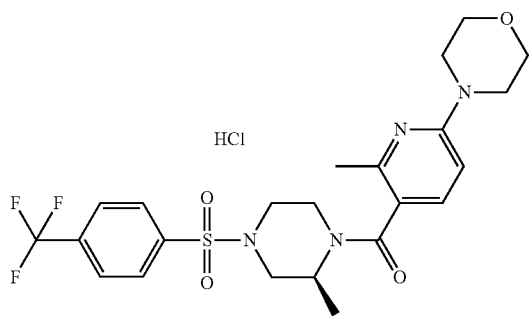

(2S)-1-[(6-Chloro-2-methyl-3-pyridinyl)carbonyl]-2-methyl-4-{[4-(trifluoromethyl)phenyl]sulfonyl}piperazine (may be prepared as described in Example 24) (67 mg, 0.15 mmol) was weighed into a microwave vial, and dissolved in isopropanol (1.4 ml). Morpholine (0.253 ml, 2.90 mmol) was added and the clear solution was heated in the microwave to 120° C. for 4 h with stirring. LCMS analysis showed ~40% conversion. Further morpholine (0.126 ml, 1.45 mmol) was added and the stirred reaction was heated to 120° C. for 6 h. LCMS analysis showed ~79% conversion. The reaction mixture was concentrated to give the crude material as a colourless gum (87 mg). This was purified by MDAP to give the free base of the title compound as a colourless gum (44 mg).

m/z (API-ES) 513 [M+H]$^+$

The material was dissolved in THF (0.5 ml) and treated with ethereal HCl (0.5 ml) and reconcentrated. The resulting colourless gum was triturated with ether, then dried, to give the title compound (40 mg) as a colourless solid.

m/z (API-ES) 513 [M+H]$^+$

Example 35

3-Methyl-4-[((3S)-3-methyl-4-{[2-methyl-6-(4-morpholinyl)-3-pyridinyl]carbonyl}-1-piperazinyl)sulfonyl]benzonitrile hydrochloride

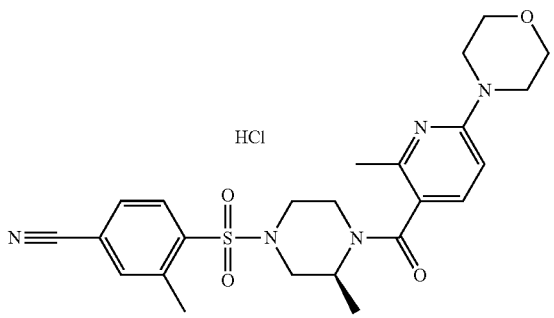

4-({(3S)-4-[(6-Chloro-2-methyl-3-pyridinyl)carbonyl]-3-methyl-1-piperazinyl}sulfonyl)-3-methylbenzonitrile (may be prepared as described in Example 25) (55 mg, 0.13 mmol) was weighed into a microwave vial, and suspended in isopropanol (1.3 ml). Morpholine (0.221 ml, 2.54 mmol) was added and the mixture was heated in the microwave to 120° C. for 12 h with stirring. LCMS analysis indicated >65% conversion. The reaction mixture was concentrated to give the crude material as a pale yellow gum (78 mg). This was purified by MDAP to give the free base of the title compound as a colourless gum (31 mg).

m/z (API-ES) 484 [M+H]$^+$

The material was dissolved in THF (0.5 ml) and treated with ethereal HCl (0.5 ml) and reconcentrated. The resulting colourless gum was triturated with ether, then dried, to the title compound (26 mg) as a colourless solid.

m/z (API-ES) 484 [M+H]$^+$

Example 36

N-Ethyl-6-methyl-5-[((2S)-2-methyl-4-{[4-(trifluoromethyl)phenyl]sulfonyl}-1-piperazinyl)carbonyl]-2-pyridinamine hydrochloride

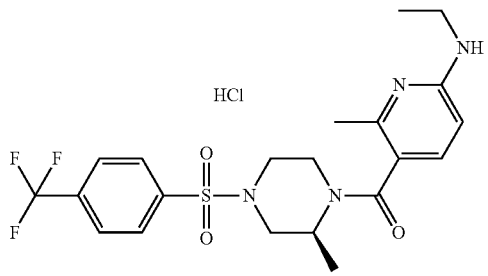

(2S)-1-[(6-Chloro-2-methyl-3-pyridinyl)carbonyl]-2-methyl-4-{[4-(trifluoromethyl)phenyl]sulfonyl}piperazine (may be prepared as described in Example 24) (67 mg, 0.15 mmol) was weighed into a microwave vial, and dissolved in isopropanol (0.7 ml). Ethylamine, 2.0M in methanol (1.5 ml, 3.0 mmol) was added, and the clear solution was heated in the microwave to 120° C. for 6 h with stirring. LCMS analysis showed <20% conversion. The mixture was treated with further ethylamine, 2.0M in methanol (0.75 ml, 1.50 mmol) and returned to the microwave for 18 h at 120° C. with stirring. LCMS analysis showed ~50% conversion. The reaction mixture was treated with further ethylamine, 2.0M in methanol (1.5 ml, 3.0 mmol), and again heated in the microwave for 18 h at 120° C. with stirring. LCMS now showed adequate conversion, >65%. The reaction mixture was concentrated to give the crude material as a yellow gum (76 mg). This was purified by MDAP to give the free base of the title compound as a pale yellow gum (34 mg).

m/z (API-ES) 471 [M+H]$^+$ $^1$H NMR (400MHz, DMSO-d$_6$) δ ppm 1.10 (t, J=7 Hz, 3 H), 1.15-1.28 (m, 3 H), 2.10 (s, 3 H), 2.28-2.38 (m, 1 H), 2.46-2.53 (m, 1 H), 3.21 (quint, J=6.5 Hz, 2 H) 3.10-3.76 (m, obscured by water, 3 H), 3.8-4.3 (v br, 1 H), 4.5-5.0 (v br, 1 H), 6.22 (d, J=8.5 Hz, 1 H), 6.65 (t, J=6 Hz, N—H), 7.13 (d, J=8.5 Hz, 1 H), 7.95 (d, J=8 Hz, 2 H), 8.05 (d, J=8 Hz, 2 H).

The material was dissolved in THF (0.5 ml) and treated with ethereal HCl (0.5 ml) and reconcentrated. The resulting pale yellow gum was triturated with ether, then dried, to give the title compound (25 mg) as a pale yellow solid.

m/z (API-ES) 471 [M+H]$^+$

Example 37

N,6-Dimethyl-5-[((2S)-2-methyl-4-{[4-(trifluoromethyl)phenyl]sulfonyl}-1-piperazinyl)carbonyl]-2-pyridinamine hydrochloride

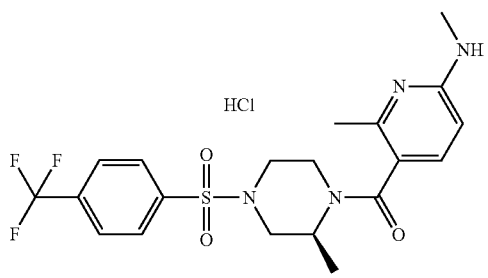

(2S)-1-[(6-chloro-2-methyl-3-pyridinyl)carbonyl]-2-methyl-4-{[4-(trifluoromethyl)phenyl]sulfonyl}piperazine (may be prepared as described in Example 24) (66 mg, 0.14 mmol) was weighed into a microwave vial, and treated with methylamine, 2 molar in THF (1.5 ml, 3.00 mmol). The clear solution was heated in the microwave to 120° C. for 24 h with stirring.

LCMS analysis showed only ~16% conversion. The mixture was treated with further methylamine, 2 molar in THF (0.75 ml, 1.50 mmol) and returned to the microwave for 16 h at 140° C. with stirring. LCMS analysis showed ~23% conversion. The reaction mixture was concentrated under a stream of argon. The crude residue was dissolved in methanol (0.5 ml). This solution was treated with further methylamine, 2 molar in THF (1.5 ml, 3.00 mmol) and returned to the microwave for 24 h at 150° C. with stirring. LCMS analysis now showed complete conversion to product. The reaction mixture was concentrated to give the crude material as a yellow gum (77 mg).

This was purified by MDAP (High pH system) to give the free base of the title compound as a colourless gum (49 mg).

m/z (API-ES) 457 [M+H]$^+$

1H NMR (400MHz, DMSO-d$_6$) δ ppm 1.17-1.25 (m, 3 H), 2.12 (s, 3 H), 2.28-2.37 (m, 1 H), 2.47-2.53 (m, 1 H, obscured by DMSO), 2.74 (d, J=4.5 Hz, 3 H) 3.08-3.45 (m, 1 H), 3.45-3.55 (m, 1 H), 3.56-3.75 (m, 1 H), 3.9-4.3 (v br, 1 H), 4.5-4.9 (v br, 1 H), 6.22 (d, J=8.5 Hz, 1 H), 6.62-6.68 (m, N—H), 7.15 (d, J=8.5 Hz, 1 H), 7.95 (d, J=8 Hz, 2 H), 8.05 (d, J=8 Hz, 2 H).

The material was dissolved in THF (0.5 ml) and treated with ethereal HCl (0.5 ml) and reconcentrated. The resulting colourless gum was triturated with ether, then dried, to give the title compound (49 mg) as a colourless solid.

m/z (API-ES) 457 [M+H]$^+$

Example 38

3-Methyl-4-[((3S)-3-methyl-4-{[2-methyl-6-(methylamino)-3-pyridinyl]carbonyl}-1-piperazinyl)sulfonyl]benzonitrile

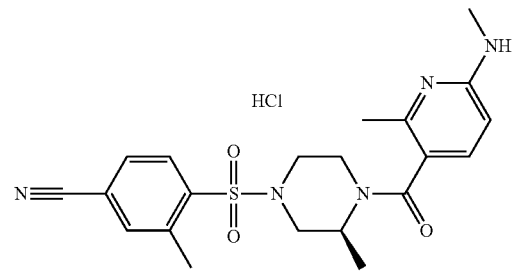

4-({(3S)-4-[(6-Chloro-2-methyl-3-pyridinyl)carbonyl]-3-methyl-1-piperazinyl}sulfonyl)-3-methylbenzonitrile (may be prepared as described in Example 25) (62 mg, 0.14 mmol) was weighed into a microwave vial with stirrer and treated with methylamine, 2 molar in THF (1.5 ml, 3.00 mmol). The vial was heated in the microwave to 140° C. for 12 h with stirring. LCMS analysis showed only ~13% conversion. The reaction mixture was treated with further methylamine, 2 molar in THF (0.75 ml, 1.50 mmol) and heated to 150° C. in the microwave for 24 h., then left to stand three days at ambient temperature. LCMS analysis showed ~52% conversion. The reaction mixture was concentrated under argon flow to decrease the total volume by about 0.75 ml. It was treated with further methylamine, 2 molar in THF (0.75 ml, 1.50 mmol). The vial was sealed and the reaction was heated in the microwave with stirring at 150° C. for 24 h. LCMS analysis showed ~60% conversion. The reaction mixture was concentrated under argon flow to give the crude material as a yellow gum (87 mg). This was purified by MDAP (High pH system) to give a colourless gum (25 mg). However, LCMS analysis showed the presence of an impurity. The material was again purified by MDAP (High pH system, extended run) to give a colourless gum (17 mg). During conversion to the hydrochloride salt, this compound proved slightly sensitive to acid, as LCMS analysis showed an impurity. The material was again purified by MDAP (High pH system, extended run) to give a colourless gum, which was re-dissolved in methanol, treated with water and reconcentrated to give the title compound (14 mg) as a colourless solid.

m/z (API-ES) 428 [M+H]+

$^1$H NMR (400 MHz, CHLOROFORM-d) δ ppm 1.23-1.35 (m, 3 H), 2.30 (s, 3 H), 2.61-2.73 (m, 4 H), 2.86-2.93 (m, 1 H), 2.91 (d, J=5 Hz, 3 H), 3.17-3.34 (m, 1 H), 3.51-3.62 (m, 1 H), 3.63-3.75 (m, 1 H), 3.9-4.4 (v br, 1 H), 4.68-4.75 (m, N—H), 4.9-5.2 (v br, 1 H), 6.21 (d, J=8.5 Hz, 1 H), 7.20 (d, J=8.5 Hz, 1 H), 7.62-7.66 (m, 2 H), 7.96 (d, J=8 Hz, 1 H).

Example 39

(2S)-1-{[6-(1-Azetidinyl)-2-methyl-3-pyridinyl]carbonyl}-2-methyl-4-{[4-(trifluoromethyl)phenyl]sulfonyl}piperazine hydrochloride

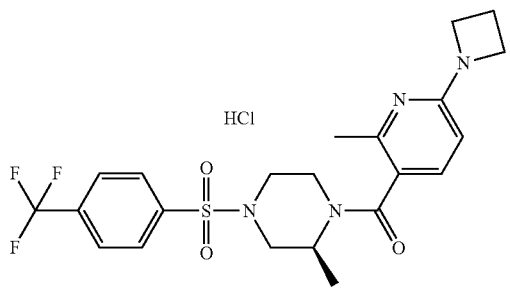

(2S)-1-[(6-Chloro-2-methyl-3-pyridinyl)carbonyl]-2-methyl-4-{[4-(trifluoromethyl)phenyl]sulfonyl}piperazine (may be prepared as described in Example 24) (66 mg, 0.14 mmol) was transferred into a microwave vial as a solution in isopropanol (1.4 ml). Azetidine (0.163 ml, 2.42 mmol) was added and the clear solution was heated in the microwave to 120° C. for 18 h with stirring. LCMS analysis showed >80% conversion. The reaction mixture was concentrated to give the crude material as a colourless gum (~200 mg). This was purified by MDAP to give the free base of the title compound as a brown gum (45 mg).

m/z (API-ES) 483 [M+H]+

$^1$H NMR (400 MHz, CHLOROFORM-d) δ ppm 1.28-1.43 (m, 3 H), 2.12-2.55 (m, 7 H), 3.20-3.52 (m, 1 H), 3.54-3.68 (m, 1 H), 3.69-3.90 (m, 1 H), 3.9-4.1 (v br, 1 H), 4.04 (t, J=7 Hz, 4 H), 4.2-5.2 (v br, 1 H), 6.05 (d, J=8.5 Hz, 1 H), 7.14 (br, 1 H), 7.80-7.90 (m, 4 H).

The material was dissolved in THF (0.5 ml) and treated with 4M HCl in dioxan (0.1 ml) and reconcentrated. The resulting brown gum was triturated with ether, then dried, to give the title compound (46 mg) as a solid.

m/z (API-ES) 483 [M+H]+

Example 40

4-[((3S)-4-{[6-(1-Azetidinyl)-2-methyl-3-pyridinyl]carbonyl}-3-methyl-1-piperazinyl)sulfonyl]-3-methylbenzonitrile hydrochloride

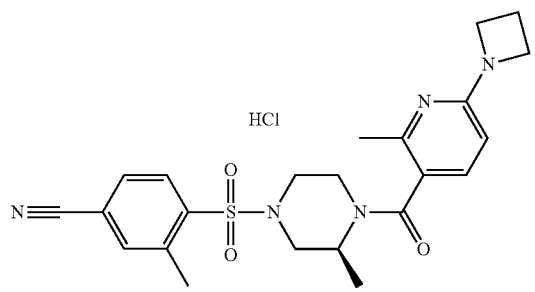

4-({(3S)-4-[(6-Chloro-2-methyl-3-pyridinyl)carbonyl]-3-methyl-1-piperazinyl}sulfonyl)-3-methylbenzonitrile (may be prepared as described in Example 25) (65 mg, 0.15 mmol) was weighed into a microwave vial and suspended in isopropanol (1.5 ml). Azetidine (0.203 ml, 3.01 mmol) was added and the mixture was heated in the microwave to 120° C. for 18 h with stirring. LCMS analysis showed >80% conversion. The reaction mixture was concentrated to give the crude material as a colourless gum (273 mg). This was purified by MDAP to give the free base of the title compound as a colourless gum (32 mg).

m/z (API-ES) 454 [M+H]+

$^1$H NMR (400 MHz, CHLOROFORM-d) δ ppm 1.21-1.32 (m, 3 H), 2.20-2.42 (m, 4 H), 2.39 (quintet, J=7.5 Hz, 2 H), 2.59-2.72 (m, 4 H), 2.82-2.95 (m, 1 H), 3.18-3.32 (m, 1 H), 3.50-3.61 (m, 1 H), 3.62-3.75 (m, 1 H), 4.05 (t, J=7.5 Hz, 4 H), 4.2-5.2 (v br, 1 H), 6.07 (d, J=8.5 Hz, 1 H), 7.17 (d, J=8 Hz, 1 H), 7.60-7.65 (m, 2 H), 7.96 (d, J=8.5 Hz, 1 H).

The material was dissolved in THF (0.5 ml) and treated with 4M HCl in dioxan (0.2 ml) and reconcentrated. The resulting colourless gum was triturated with ether, then dried, to give the title compound (29 mg) as a colourless solid.

m/z (API-ES) 454 [M+H]+

Example 41

N,N-Dimethyl-5-[((2S)-2-methyl-4-{[4-(trifluoromethyl)phenyl]sulfonyl}-1-piperazinyl)carbonyl]-2-pyridinamine hydrochloride

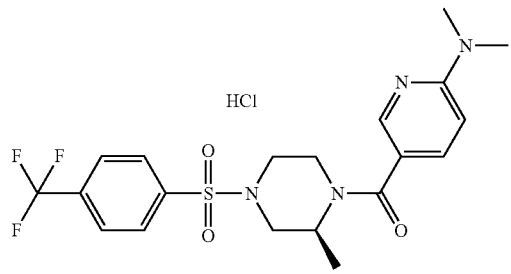

(2S)-1-[(6-Chloro-3-pyridinyl)carbonyl]-2-methyl-4-{[4-(trifluoromethyl)phenyl]sulfonyl}piperazine (may be prepared as described in Example 26) (67 mg, 0.15 mmol) was weighed into a microwave vial, suspended in isopropanol (0.75 ml) and treated with dimethylamine, 2M in methanol (0.75 ml, 1.50 mmol). The mixture was heated in the microwave to 120° C. for 18 h with stirring. LCMS analysis showed clean conversion to the product. The reaction mixture was concentrated to give the crude material as a pale yellow gum/solid. This was purified by MDAP (High pH system) to give the free base of the title compound as a colourless gum (61 mg).

m/z (API-ES) 457 [M+H]+

The material was dissolved in THF (0.5 ml) and treated with ethereal HCl (0.5 ml) and reconcentrated. The resulting colourless gum was triturated with ether, then dried, to give the title compound (73 mg) as a colourless solid.

m/z (API-ES) 457 [M+H]+

Example 42

4-{5-[((2S)-2-Methyl-4-{[4-(trifluoromethyl)phenyl]sulfonyl}-1-piperazinyl)carbonyl]-2-pyridinyl}morpholine hydrochloride

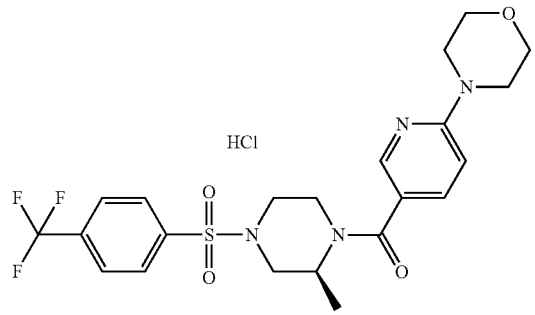

(2S)-1-[(6-Chloro-3-pyridinyl)carbonyl]-2-methyl-4-{[4-(trifluoromethyl)phenyl]sulfonyl}piperazine (may be prepared as described in Example 26) (67 mg, 0.15 mmol) was weighed into a microwave vial, suspended in isopropanol (1.5 ml) and treated with morpholine (0.261 ml, 2.99 mmol). The mixture was heated in the microwave to 120° C. for 18 h with stirring. LCMS analysis showed clean conversion to product. The reaction mixture was concentrated to give the crude material as a colourless gum. This was purified by MDAP (High pH system) to give the free base of the title compound as a colourless gum (69 mg).

m/z (API-ES) 499 [M+H]+

The material was dissolved in THF (0.5 ml) and treated with ethereal HCl (0.5 ml) and reconcentrated. The resulting colourless gum was triturated with ether, then dried, to give the title compound (77 mg) as a colourless solid.

m/z (API-ES) 499 [M+H]+

Example 43

N-Ethyl-5-[((2S)-2-methyl-4-{[4-(trifluoromethyl)phenyl]sulfonyl}-1-piperazinyl)carbonyl]-2-pyridinamine hydrochloride

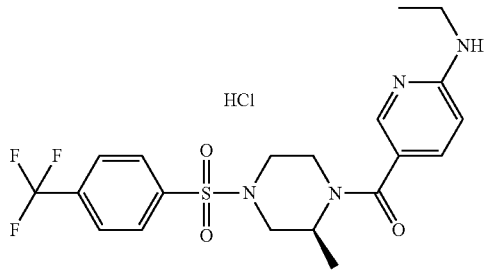

(2S)-1-[(6-Chloro-3-pyridinyl)carbonyl]-2-methyl-4-{[4-(trifluoromethyl)phenyl]sulfonyl}piperazine (may be prepared as described in Example 26) (67 mg, 0.15 mmol) was weighed into a microwave vial, and treated with ethylamine, 2.0M in methanol (1.5 ml, 3.0 mmol). The clear solution was heated in the microwave to 120° C. for 18 h with stirring. LCMS analysis showed complete conversion. The reaction mixture was concentrated to give the crude material as a yellow gum (76 mg). This was purified by MDAP to give the free base of the title compound as a colourless gum (59 mg).

m/z (API-ES) 457 [M+H]+

$^1$H NMR (400 MHz, DMSO-$d_6$) δ ppm 1.11 (t, J=7.5 Hz, 3 H), 1.24 (d, J=6.5 Hz, 3 H), 2.38 (td, J=6.5, 3.5 Hz, 1 H), 2.48-2.54 (m, obscured by DMSO, 1 H), 3.20-3.30 (m, 2 H) 3.30-3.40 (m, obscured by water, 1 H), 3.48 (d, J=12 Hz, 1 H), 3.66 (d, J=12 Hz, 1 H), 3.89-3.99 (m, 1 H), 4.36-4.50 (m, 1 H), 6.40 (d, J=8 Hz, 1 H), 6.96 (t, J=5 Hz, N—H), 7.36 (dd, J=8, 2 Hz, 1 H), 7.94 (d, J=8 Hz, 2 H), 8.01 (d, J=2 Hz, 1 H), 8.05 (d, J=8 Hz, 2 H).

The material was dissolved in THF (0.5 ml) and treated with ethereal HCl (0.5 ml) and reconcentrated. The resulting colourless gum was triturated with ether, then dried, to give the title compound (56 mg) as a cream solid.

m/z (API-ES) 457 [M+H]+

$^1$H NMR (400MHz, DMSO-$d_6$) δ ppm 1.19 (t, J=7.5 Hz, 3 H), 1.27 (d, J=6.5 Hz, 3 H), 2.37-2.47 (m, 1 H), 2.56 (dd, J=12, 3.5 Hz, 1 H), 3.20-3.80 (m, obscured by water, 5 H), 3.75-4.0 (v br, 1 H), 4.20-4.50 (v br, 1 H), 6.96 (d, J=8.5 Hz, 1 H), 7.76 (dd, J=8.5 Hz, 1 H), 7.93-7.99 (m, 3 H), 8.06 (d, J=8 Hz, 2 H), 8.7-9.2 (v br, N—H).

Example 44

Methyl-5-[((2S)-2-methyl-4-{[4-(trifluoromethyl)phenyl]sulfonyl}-1-piperazinyl)carbonyl]-2-pyridinamine hydrochloride

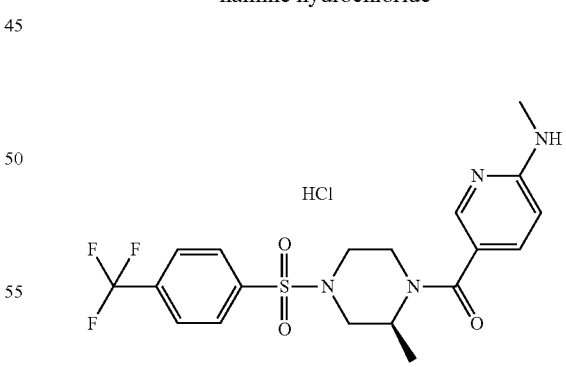

2S)-1-[(6-Chloro-3-pyridinyl)carbonyl]-2-methyl-4-{[4-(trifluoromethyl)phenyl]sulfonyl}piperazine (may be prepared as described in Example 26) (67 mg, 0.15 mmol) was weighed into a microwave vial, and treated with methylamine, 2 molar in THF (1.5 ml, 3.00 mmol). The clear solution was heated in the microwave to 120° C. for 12 h with stirring. LCMS analysis showed ~60% conversion.

The mixture was treated with further methylamine, 2 molar in THF (0.75 ml, 1.50 mmol) and returned to the microwave for 16 h at 120° C. with stirring. LCMS analysis showed >71% conversion. The reaction mixture was concentrated to give the crude material as a yellow gum (73 mg). This was purified by MDAP (High pH system) to give the free base of the title compound as a colourless gum (35 mg).

m/z (API-ES) 443 [M+H]$^+$ $^1$H NMR (400 MHz, CHLOROFORM-d) δ ppm 1.44 (d, J=6.5 Hz, 3 H), 2.34 (td, J=12, 3.5 Hz, 1 H), 2.48 (dd, J=12, 3.5 Hz, 1 H), 2.94 (d, J=6, 3 H), 3.40 (td, J=13, 3 Hz, 1 H), 3.59 (d, J=12 Hz, 1 H), 3.78 (brd, J=12 Hz, 1 H), 4.11-4.21 (m, 1 H), 4.53-4.64 (m, 1 H), 4.80-4.88 (m, N—H), 6.36 (d, J=8.5 Hz, 1 H), 7.48 (dd, J=8.5, 2 Hz, 1 H), 7.80-7.89 (m, 4 H), 8.10 (d, J=2 Hz, 1 H).

The material was dissolved in THF (0.5 ml) and treated with ethereal HCl (0.5 ml) and reconcentrated. The resulting colourless gum was triturated with ether, then dried, to give the title compound (29 mg) as an off-white solid.

m/z (API-ES) 443 [M+H]$^+$

Example 45

(2S)-1-{[6-(1-Azetidinyl)-3-pyridinyl]carbonyl}-2-methyl-4-{[4-(trifluoromethyl)phenyl]sulfonyl}piperazine hydrochloride

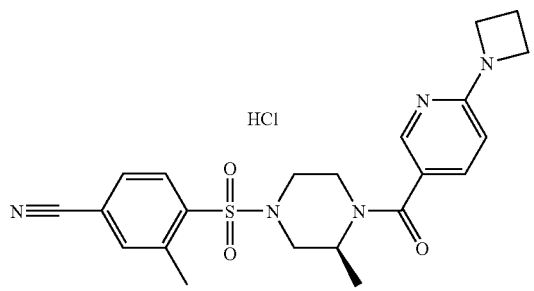

(2S)-1-[(6-Chloro-3-pyridinyl)carbonyl]-2-methyl-4-{[4-(trifluoromethyl)phenyl]sulfonyl}piperazine (may be prepared as described in Example 26) (69 mg, 0.154 mmol) was transferred into a microwave vial as a solution in isopropanol (1.5 ml). Azetidine (0.208 ml, 3.08 mmol) was added and the clear solution was heated in the microwave to 120° C. for 12 h with stirring. LCMS analysis showed complete conversion. The reaction mixture was concentrated to give the crude material as a colourless gum (206 mg). This was purified by MDAP (High pH system) to give the free base of the title compound as a colourless gum (65 mg).

m/z (API-ES) 469 [M+H]$^+$ $^1$H NMR (400 MHz, CHLOROFORM-d) δ ppm 1.42 (d, J=6.5 Hz, 3 H), 2.33 (td, J=12, 3 Hz, 1 H), 2.39-2.50 (m, 3 H), 3.38 (td, J=12.5, 3 Hz, 1 H), 3.55-3.62 (m, 1 H), 3.73-3.80 (m, 1 H), 4.08 (t, J=7.5 Hz, 4 H), 4.10-4.20 (m, 1 H), 4.52-4.63 (br, 1 H), 6.21 (d, J=8.5 Hz, 1 H), 7.49 (dd, J=8, 2 Hz, 1 H), 7.79-7.91 (m, 4 H), 8.12 (d, J=2 Hz, 1 H).

The material was dissolved in THF (0.5 ml) and treated with 4M HCl in dioxan (0.2 ml) and reconcentrated. The resulting colourless gum was triturated with ether, then dried, to give the title compound (79 mg) as a colourless solid.

m/z (API-ES) 469 [M+H]$^+$ $^1$H NMR (400 MHz, CHLOROFORM-d) δ ppm 1.42 (d, J=6.5 Hz, 3 H), 2.38 (td, J=12, 3 Hz, 1 H), 2.48-2.64 (m, 3 H), 3.38-3.50 (m, 1 H), 3.57-3.67 (m, 1 H), 3.68-3.87 (m, 5 H), 3.92-4.06 (br, 1 H), 4.4-4.6 (obscured by H$_2$O, 1 H), 6.48 (d, J=8.5 Hz, 1 H), 7.76 (dd, J=8, 2 Hz, 1 H), 7.82-7.91 (m, 4 H), 7.97 (d, J=2 Hz, 1 H).

Example 46

N,N,4-Trimethyl-5-[((2S)-2-methyl-4-{[4-(trifluoromethyl)phenyl]sulfonyl}-1-piperazinyl)carbonyl]-2-pyridinamine hydrochloride

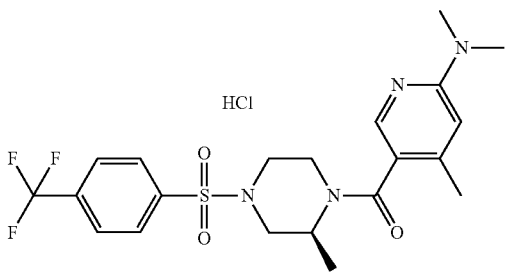

(2S)-1-[(6-Fluoro-4-methyl-3-pyridinyl)carbonyl]-2-methyl-4-{[4-(trifluoromethyl)phenyl]sulfonyl}piperazine (may be prepared as described in Example 27) (62 mg, 0.14 mmol) was weighed into a microwave vial, and dissolved in isopropanol (0.7 ml). The dimethylamine, 2M in methanol (0.7 ml, 1.40 mmol) was added, and the mixture was heated in the microwave to 120° C. for 4 h with stirring. LCMS analysis showed clean conversion to product. The reaction mixture was concentrated to give the crude material as a pale yellow gum (80 mg). This was purified by MDAP (High pH system) to give the free base of the title compound as a colourless gum (56 mg).

m/z (API-ES) 471 [M+H]$^+$

The material was dissolved in THF (0.5 ml) and treated with ethereal HCl (0.5 ml) and reconcentrated. The resulting colourless gum was triturated with ether, then dried, to give the title compound (56 mg) as a colourless solid.

m/z (API-ES) 471 [M+H]$^+$

Example 47

4-{4-Methyl-5-[((2S)-2-methyl-4-{[4-(trifluoromethyl)phenyl]sulfonyl}-1-piperazinyl)carbonyl]-2-pyridinyl}morpholine hydrochloride

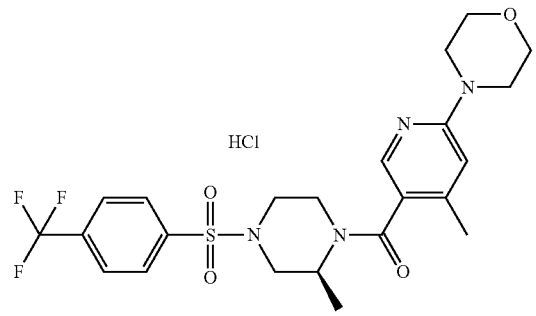

(2S)-1-[(6-fluoro-4-methyl-3-pyridinyl)carbonyl]-2-methyl-4-{[4-(trifluoromethyl)phenyl]sulfonyl}piperazine (may be prepared as described in Example 27) (60 mg, 0.14 mmol) was weighed into a microwave vial, and dissolved in isopropanol (1.4 ml). Morpholine (0.236 ml, 2.71 mmol) was added, and the mixture was heated in the microwave to 120° C. for 5 h with stirring. LCMS analysis showed clean conversion to product. The reaction mixture was concentrated to give the crude material as a colourless gum/glass (85 mg). This was purified by MDAP (High pH system) to give the free base of the title compound as a colourless gum (57 mg).

m/z (API-ES) 513 [M+H]$^+$

1H NMR (400 MHz, CHLOROFORM-d) δ ppm 1.32-1.45 (m, 3 H), 2.19 (s, 3 H), 2.25-2.36 (m, 1 H), 2.42-2.53 (m, 1 H), 3.28-3.41 (m, 1 H), 3.47-3.54 (m, 4 H), 3.56-3.66 (m, 1 H), 3.70-3.88 (m, 5 H), 4.0-4.50 (v br, 1 H), 4.8-5.1 (v br, 1 H), 6.44 (s, 1 H), 7.80-7.93 (m, 5 H).

The material was dissolved in THF (0.5 ml) and treated with ethereal HCl (0.5 ml) and reconcentrated. The resulting colourless gum was triturated with ether, then dried, to give the title compound (54 mg) as a colourless solid.

m/z (API-ES) 513 [M+H]$^+$

Example 48

N,4-Dimethyl-5-[((2S)-2-methyl-4-{[4-(trifluoromethyl)phenyl]sulfonyl}-1-piperazinyl)carbonyl]-2-pyridinamine hydrochloride

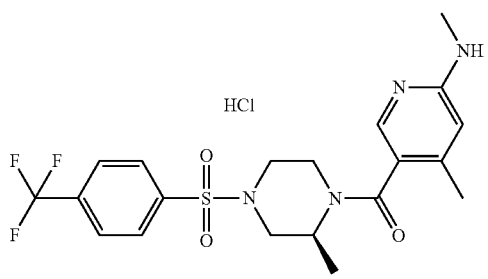

(2S)-1-[(6-Fluoro-4-methyl-3-pyridinyl)carbonyl]-2-methyl-4-{[4-(trifluoromethyl)phenyl]sulfonyl}piperazine (may be prepared as described in Example 27) (67 mg, 0.15 mmol) was weighed into a microwave vial. The methylamine, 2 molar in THF (1.5 ml, 3.00 mmol) was added, and the mixture was heated in the microwave to 120° C. for 18 h with stirring.

LCMS analysis showed clean conversion to product. The reaction mixture was concentrated to give the crude material as a pale yellow gum (70 mg). This was purified by MDAP (High pH system) to give the free base of the title compound as a colourless gum (60 mg).

m/z (API-ES) 457 [M+H]$^+$ $^1$H NMR (400 MHz, CHLOROFORM-d) δ ppm 1.32-1.43 (m, 3 H), 2.16 (s, 3 H), 2.30 (br t, J=11 Hz, 1 H), 2.43-2.52 (m, 1 H), 2.91 (d, J=5 Hz, 3 H), 3.27-3.41 (m, 1 H), 3.54-3.65 (m, 1 H), 3.70-3.84 (m, 1 H), 4.0-4.50 (v br, 1 H), 4.65 (q, J=4.5 Hz, N—H), 4.7-5.2 (v br, 1 H), 6.20 (s, 1 H), 7.70 (s, 1 H), 7.80-7.89 (m, 4 H).

The material was dissolved in THF (0.5 ml) and treated with 4M HCl in dioxan (0.1 ml) and reconcentrated. The resulting colourless gum was triturated with ether, then dried, to give the title compound (63 mg).

m/z (API-ES) 457 [M+H]$^+$ $^1$H NMR (400 MHz, CHLOROFORM-d) δ ppm 1.18-1.32 (m, 3 H), 2.16 (s, 3 H), 2.38-2.50 (m, 1 H), 2.53-2.65 (m, 1 H), 2.93 (s, 3H), 3.10-3.75 (m, obscured by water, 3H), 4.3-4.5 (v br, 1 H), 4.7-5.0 (v br, 1 H), 6.88 (br, 1 H), 7.87 (br s, 1 H), 7.96 (d, J=7.5 Hz, 2 H), 8.06 (d, J=7.5 Hz, 2 H), 8.4-9.2 (v br, N—H).

Example 49

(2S)-2-methyl-1-[(6-methyl-3-pyridinyl)carbonyl]-4-{[2-methyl-4-(trifluoromethyl)phenyl]sulfonyl}piperazine hydrochloride

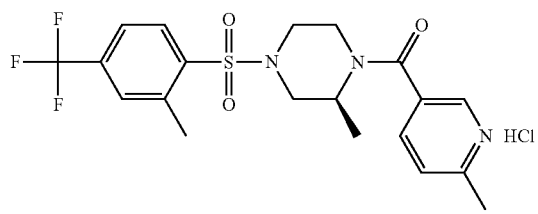

(2S)-4-{[2-bromo-4-(trifluoromethyl)phenyl]sulfonyl}-2-methyl-1-[(6-methyl-3-pyridinyl)carbonyl]piperazine (may be prepared as described in Description 31) (216 mg, 0.427 mmol), potassium carbonate (153 mg, 1.109 mmol) in 1,4-dioxane (9 ml) were stirred for 5 min then trimethylboroxin (0.154 ml, 1.109 mmol) and Pd(PPh$_3$)$_4$ (84 mg, 0.073 mmol) were added and the reaction mixture heated at 100° C. for 1 h. The reaction mixture was concentrated under vacuum, dissolved in MeOH and filtered through a 5 g SCX column. LCMS showed still some triphenylphosphine oxide and another small impurity so the product was dissolved in EtOAc (40 ml) and extracted with HCl 2N (40 ml). 2 N NaOH was added to the aqueous layer until pH12 and product extracted with EtOAc (100 ml). The organic phase was dried on a phase separation cartridge and concentrated under vacuum. LCMS of the first EtOAc layer showed it contained some of the product so was extracted again with 2 N HCl (40 ml). 2 N NaOH was added to the aqueous layer until pH12 and product extracted with EtOAc (100 ml). The organic layer was dried on a phase separation cartridge and the two batches were combined and concentrated under vacuum to give the free base of the product. The product was suspended in DCM, 0.5 ml of 1 N HCl in ether was added and the solvent was evaporated to give the title compound (193 mg).

m/z (API-ES) 442 [M+H]$^+$

1H NMR (400 MHz, DMSO-d$_6$) δ ppm 1.22 (d, J=6.8 Hz, 3H), 2.61 (s, 3H), 2.66 (s, 3H), 2.77 (m, 1H), 2.94 (d, J=9.2 Hz, 1H), 3.2-4.2 (5H hidden under broad water peak), 7.60 (d, J=8.0 Hz, 1H), 7.81 (d, J=8.4 Hz, 1H), 7.92 (s, 1H), 7.99 (d, J=8.4 Hz, 1H), 8.04 (d, J=8.0 Hz, 1H), 8.65 (s, 1H).

Example 50

4-({(3S)-4-[(6-iodo-3-pyridinyl)carbonyl]-3-methyl-1-piperazinyl}sulfonyl)-3-methylbenzonitrile

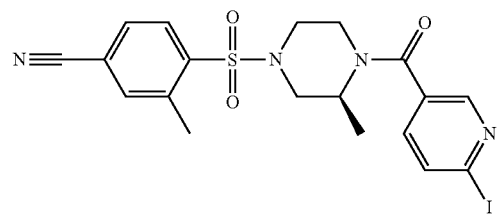

To a solution of 3-methyl-4-{[(3S)-3-methyl-1-piperazinyl]sulfonyl}benzonitrile (may be prepared as described in Description 11) (300 mg, 0.950 mmol) 6-iodo-3-pyridinecarboxylic acid (prepared from 6-chloronicotinic acid, according to the literature procedure: G. R. Newkome, C. N. Moorfield and B. Sabbaghian, *J. Org. Chem.*, 1986, 51, 953-954.) (248 mg, 0.997 mmol), HOBT (175 mg, 1.14 mmol) and Et$_3$N (0.331 ml, 2.38 mmol) in dry DMF (5 ml) at room temperature under Ar was added HBTU (432 mg, 1.14 mmol) and the resulting brown solution stirred at room temperature for 16 h. The mixture was concentrated under vacuum to leave a red gum (743 mg). Flash chromatography (silica; Flash 25S; linear gradient (6-50%) ethyl acetate in isohexane) gave the title compound as a pale yellow foam (301 mg).

m/z (API-ES) 511 [M+H]$^+$ $^1$H NMR (400 MHz, CHLOROFORM-d) δ ppm 1.37 (d, J=6.8 Hz, 3 H), 2.68 (s, 3 H), 2.69-2.78 (m, 1 H), 2.87-2.96 (m, 1 H), 3.37 (br. s., 1 H), 3.61 (d, J=12.4 Hz, 1 H), 3.74 (d, J=12.2 Hz, 1 H), 4.49 (br. s., 2 H), 7.35 (dd, J=8.1, 2.5 Hz, 1 H), 7.62-7.67 (br s, 2 H), 7.82 (dd, J=8.1, 0.6 Hz, 1 H), 7.96 (d, J=8.6 Hz, 1 H), 8.36 (d, J=2.0 Hz, 1 H)

Example 51

1-[(6-chloro-3-pyridinyl)carbonyl]-4-{[4-(trifluoromethyl)phenyl]sulfonyl}piperazine

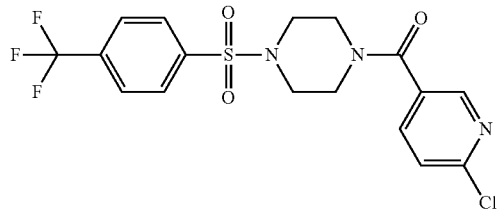

To a suspension of 6-chloro nicotinic acid (1.76 g, 11.2 mmol) in DCM (50 ml) at 0° C. was added EDC.HCl (2.93 g, 15.3 mmol), HOBt (2.34 g, 15.3 mmol) and DIPEA (7.52 ml, 40.8 mmol) and the mixture stirred for 20 min. 1-{[4-(Trifluoromethyl)phenyl]sulfonyl}piperazine (may be prepared as described in Description 1) (3.00 g, 10.2 mmol) was added and the solution allowed to warm to room temperature, then stirred overnight. The mixture was diluted with DCM (20 ml), washed with water (5×20 ml), then the organic layers dried (Na$_2$SO$_4$) and concentrated under vacuum to leave the crude compound. Flash chromatography (silica; 60% EtOAc in pet. ether) gave the title compound as a white solid (2.20 g).

m/z (API-ES) 434 [M+H]$^+$ $^1$H NMR (400 MHz, CDCl$_3$) δ ppm 3.10 (br s, 4H), 3.77 (br s), 7.39 (d, 1H), 7.66 (d, 1H), 7.85 (d, 2H), 7.89 (d, 2H), 8.38 (s, 1H).

Example 52

3-methyl-4-({(2S)-2-methyl-4-[(6-methyl-3-pyridinyl)carbonyl]-1-piperazinyl}sulfonyl)benzonitrile hydrochloride

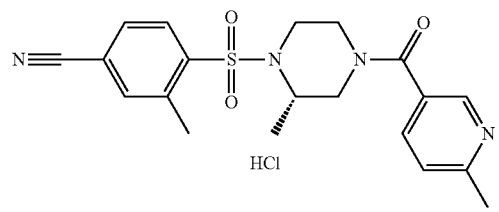

To a solution of 3-methyl-4-{[(2S)-2-methyl-1-piperazinyl]sulfonyl}benzonitrile (may be prepared as described in Description 17) (75.0 mg, 0.268 mmol), 6-methyl-3-pyridinecarboxylic acid (44.2 mg, 0.322 mmol) and DIPEA (0.070 ml, 0.403 mmol) in dry DMF (3 ml) at room temperature under Ar was added HATU (112 mg, 0.295 mmol) and the resulting yellow solution stirred at room temperature for 1 h. Concentration under vacuum gave a yellow oil, that was purified by MDAP; concentration of the desired fractions with a 2M aqueous HCl solution (2 ml) gave a clear film (110 mg). Flash chromatography (silica; Flash 12M; linear gradient (1.2-10%) [2M NH$_3$ in MeOH] in DCM) gave the title compound as a clear film (88.8 mg, 0.215 mmol), that became a white solid on standing under vacuum (2 mbar) for 18 h.

m/z (API-ES) 399 [M+H]$^+$ $^1$H NMR (400 MHz, CHLOROFORM-d) δ ppm 1.18 (br s, 3 H), 2.59 (s, 3 H), 2.62 (s, 3 H), 2.81-3.86 (m, 5 H), 4.09 (br s, 1 H), 4.32-4.91 (m, 1 H), 7.23 (d, J=7.9 Hz, 1 H), 7.60-7.66 (m, 3 H), 8.08 (d, J=8.6 Hz, 1 H), 8.52 (d, J=1.8 Hz, 1 H)

Example 53

4-({(3S)-4-[(6-ethyl-3-pyridinyl)carbonyl]-3-methyl-1-piperazinyl}sulfonyl)-3-methylbenzonitrile hydrochloride

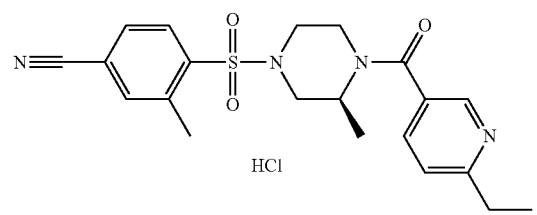

Ar was bubbled through a solution of 4-({(3S)-4-[(6-iodo-3-pyridinyl)carbonyl]-3-methyl-1-piperazinyl}sulfonyl)-3-methylbenzonitrile (may be prepared as described in Example 50) (50.0 mg, 0.098 mmol) in dry 1,4-dioxane (3 ml) for 30 min, then PdCl$_2$(dppf) (7.17 mg, 9.80 μmol) and diethylzinc (1M in hexanes, 0.118 ml, 0.118 mmol) were added, and the solution heated at 100° C. for 30 min. The solution was cooled to room temperature, then partitioned between a saturated aqueous NaHCO$_3$ solution (5 ml) and DCM (25 ml). The mixture was shaken, then applied to a phase separator; the organic layers were concentrated under vacuum to leave a dark brown oil (59 mg). Purification by MDAP and concentration of the desired fractions gave a clear film (21 mg). The film was re-dissolved in THF (1 ml), treated with HCl (1M in ether, 0.051 ml, 0.051 mmol) and dried at 35° C. under a stream of Ar to leave the title compound as a light brown gum, that became a pale yellow powder on trituration with ether (35.8 mg).

m/z (API-ES) 413 [M+H]$^+$ $^1$H NMR (400 MHz, CHLOROFORM-d) δ ppm 1.32 (t, J=7.6 Hz, 3 H), 1.38 (d, J=6.8 Hz, 3 H), 2.68 (s, 3 H), 2.73 (td, J=12.3, 3.1 Hz, 1 H), 2.87 (q, J=7.7 Hz, 2 H), 2.90 (m, 1 H), 3.37 (m, 1 H), 3.60 (d, J=12.3 Hz, 1 H), 3.74 (d, J=11.8 Hz, 1

H), 3.81-4.80 (m, 2 H), 7.26 (m, 1 H), 7.61-7.66 (m, 2 H), 7.68 (dd, J=8.1, 2.2 Hz, 1 H), 7.96 (d, J=8.6 Hz, 1 H), 8.55 (d, J=1.8 Hz, 1 H)

Example 54

3-Methyl-4-[((3S)-3-methyl-4-{[6-(1-methylethyl)-3-pyridinyl]carbonyl}-1-piperazinyl)sulfonyl]benzonitrile hydrochloride

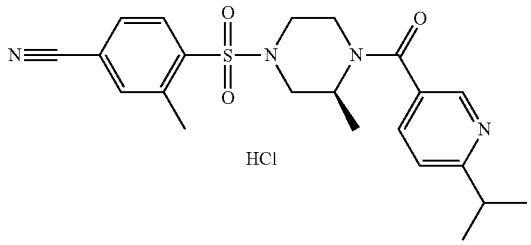

Ar was bubbled through a solution of 4-({(3S)-4-[(6-iodo-3-pyridinyl)carbonyl]-3-methyl-1-piperazinyl}sulfonyl)-3-methylbenzonitrile (may be prepared as described in Example 50) (50.0 mg, 0.098 mmol) in dry 1,4-dioxane (3 ml) for 30 min, then PdCl$_2$(dppf) (7.17 mg, 9.80 μmol) and diisopropylzinc (1M in toluene, 0.118 ml, 0.118 mmol) were added and the solution heated at 100° C. for 30 min. The solution was cooled to room temperature, then partitioned between a saturated aqueous NaHCO$_3$ solution (5 ml) and DCM (25 ml). The mixture was shaken, then applied to a phase separator; the organic layers were concentrated under vacuum to leave a dark brown oil (64 mg). Purification by MDAP and concentration of the desired fractions gave a pale yellow film. The film was re-dissolved in THF (1 ml) then treated with HCl (1M in ether, 0.045 ml, 0.045 mmol) and the solvent removed at 35° C. under a stream of Ar to leave the title compound as a pale brown gum, that became a pale yellow powder on trituration with ether (27.9 mg).

m/z (API-ES) 427 [M+H]$^+$ $^1$H NMR (400 MHz, CHLOROFORM-d) δ ppm 1.31 (d, J=6.9 Hz, 6 H), 1.38 (d, J=6.7 Hz, 3 H), 2.68 (s, 3 H), 2.74 (td, J=12.4, 3.1 Hz, 1 H), 2.91 (dd, J=12.2, 2.7 Hz, 1 H), 3.11 (spt, J=7.0 Hz, 1 H), 3.37 (m, 1 H), 3.60 (d, J=12.2 Hz, 1 H), 3.75 (d, J=12.3 Hz, 1 H), 3.87-4.81 (m, 2 H), 7.26 (m, 1 H), 7.61-7.69 (m, 3 H), 7.96 (d, J=8.7 Hz, 1 H), 8.54 (d, J=1.7 Hz, 1 H)

Example 55

(2S)-2-methyl-1-[(2-methyl-3-pyridinyl)carbonyl]-4-{[2-methyl-4-(trifluoromethyl)phenyl]sulfonyl}piperazine hydrochloride

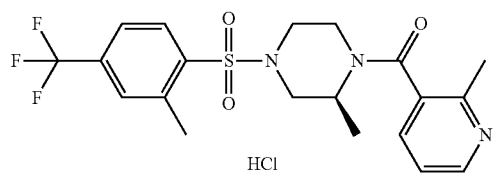

To a solution of (3S)-3-methyl-1-{[2-methyl-4-(trifluoromethyl)phenyl]sulfonyl}piperazine (may be prepared as described in Description 24) (100 mg, 0.279 mmol) and 2-methyl-3-pyridinecarboxylic acid (38.2 mg, 0.279 mmol) in DMF (5 mL), HOBt (46.9 mg, 0.307 mmol), N-ethylmorpholine (0.078 mL, 0.613 mmol) and HBTU (116 mg, 0.307 mmol) were added and the reaction mixture stirred at room temperature for 60 h. The mixture was concentrated under vacuum, then partitioned between water (10 ml) and DCM (10 ml). The aqueous was extracted with DCM (10 ml) and the organic layer separated by hydrophobic frit. The organic layers were concentrated under vacuum to leave a yellow oil that was re-dissolved in 1:1 DMSO/MeCN (1.7 ml), split into two batches and purified by MDAP. The relevant fractions were combined and concentrated under vacuum to leave yellow oil (91 mg). This was re-dissolved in THF (5 ml) and treated with 1M HCl in ether (0.2 ml). The solvent was removed at 40° C. under a flow of Ar to leave the title compound as a white solid (101 mg).

m/z (API-ES) 442 [M+H]$^+$ $^1$H NMR (400 MHz, METHANOL-d$_4$) δ ppm 1.26-1.44 (m, 3 H), 2.64-2.79 (m, 6 H), 2.83-2.98 (m, 1 H), 3.10 (d, J=10.1 Hz, 1 H), 3.37-3.76 (m, 3 H), 3.80-3.95 (m, 1 H), 4.95-5.03 (m, 1 H), 7.72 (d, J=6.5 Hz, 1 H), 7.76 (s, 1 H), 7.96 (br. s., 1 H), 8.06 (d, J=6.7 Hz, 1 H), 8.49 (br. s., 1 H), 8.80 (br. s., 1 H).

Example 56

N,N-diethyl-5-[(4-{[4-(trifluoromethyl)phenyl]sulfonyl}-1-piperazinyl)carbonyl]-2-pyridinamine

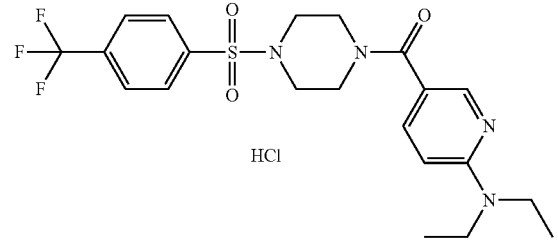

A solution of 1-[(6-chloro-3-pyridinyl)carbonyl]-4-{[4-(trifluoromethyl)phenyl]sulfonyl}piperazine (may be prepared as described in Example 51) (100 mg, 0.23 mmol) and diethylamine (0.45 ml, 2.3 mmol) in isopropanol (3 ml) was irradiated to 180° C. for 1 h. The mixture was concentrated, then the residue re-dissolved in EtOAc (100 ml), washed with water (25 ml), brine (25 ml), dried (Na$_2$SO$_4$) and concentrated under vacuum to leave an orange solid (110 mg). Flash chromatography (silica; 40% EtOAc in pet. ether) gave the title compound as a solid (35 mg).

m/z (API-ES) 471 [M+H]$^+$ $^1$H NMR (400 MHz, DMSO-d$_6$) δ ppm 1.08 (t, 6H), 3.04 (br s, 4H), 3.51 (m, 4H), 3.59 (br s, 4H), 6.55 (d, 1H), 7.48 (dd, 1H), 7.96 (d, 2H), 8.04 (d, 2H), 8.11 (d, 1H).

Example 57

N,N-dimethyl-5-[(4-{[4-(trifluoromethyl)phenyl]sulfonyl}-1-piperazinyl)carbonyl]-2-pyridinamine

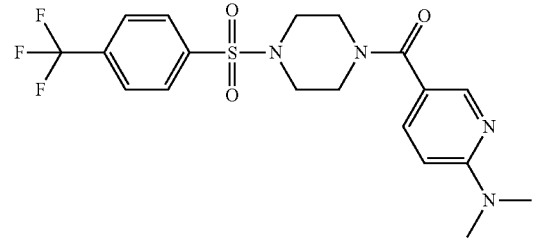

A solution of 1-[(6-chloro-3-pyridinyl)carbonyl]-4-{[4-(trifluoromethyl)phenyl]sulfonyl}piperazine (may be prepared as described in Example 51) (300 mg, 0.692 mmol) and dimethylamine (2M, 0.35 ml, 6.921 mmol) was irradiated to 100° C. for 3 h. The mixture was concentrated under vacuum, re-dissolved in DCM (20 ml), washed with water (3×10 ml), dried (Na$_2$SO$_4$) and concentrated under vacuum to leave the crude product. Flash chromatography (silica; 50% EtOAc in pet. ether) gave the title compound as a solid (169 mg).

m/z (API-ES) 443 [M+H]$^+$ $^1$H NMR (400 MHz, CHLOROFORM-d) δ ppm 3.08 (m, 4H), 3.13 (s, 6H), 3.67 (m, 4H), 6.48 (d, 1H), 7.56 (dd, 1H), 7.84 (d, 2H), 7.87 (d, 2H), 8.18 (d, 1H).

Examples 58 to 68

The compounds of Table 1 were prepared in a similar manner as the compound of Example 1 using the corresponding reactants.

TABLE 1

| Example no. | Name | Structure | m/z (API-ES) [M + H]$^+$ |
|---|---|---|---|
| 58 | (2R)-2-methyl-1-[(2-methyl-3-pyridinyl)carbonyl]-4-({4-[(trifluoromethyl)oxy]phenyl}sulfonyl)piperazine | 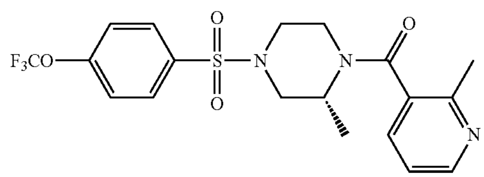 | 444 |
| 59 | (2S)-2-methyl-1-[(6-methyl-3-pyridinyl)carbonyl]-4-{[2-methyl-5-(trifluoromethyl)phenyl]sulfonyl}piperazine | 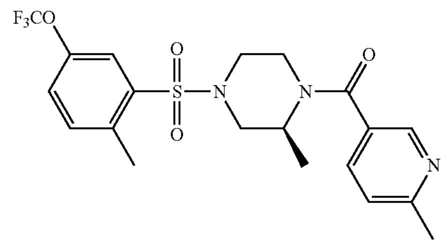 | 442 |
| 60 | (2S)-2-methyl-1-[(2-methyl-3-pyridinyl)carbonyl]-4-{[2-methyl-5-(trifluoromethyl)phenyl]sulfonyl}piperazine | 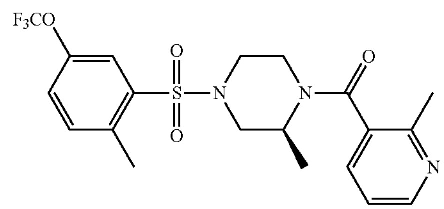 | 442 |
| 61 | 1-[(6-methyl-3-pyridinyl)carbonyl]-4-{[2-methyl-5-(trifluoromethyl)phenyl]sulfonyl}piperazine | 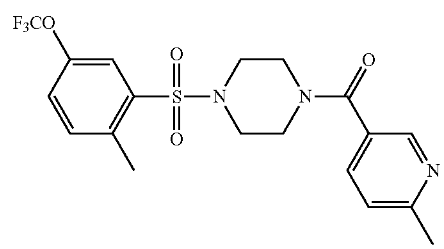 | 428 |
| 62 | 1-[(2-methyl-3-pyridinyl)carbonyl]-4-{[2-methyl-5-(trifluoromethyl)phenyl]sulfonyl}piperazine | 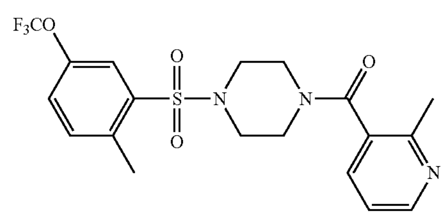 | 428 |
| 63 | 3-methyl-4-({(3R)-3-methyl-4-[(6-methyl-3-pyridinyl)carbonyl]-1-piperazinyl}sulfonyl)benzonitrile | 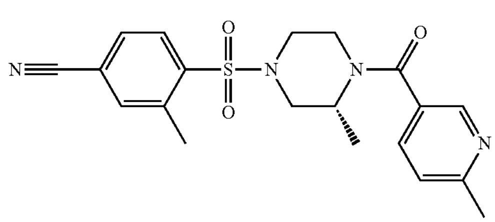 | 399 |

TABLE 1-continued

| Example no. | Name | Structure | m/z (API-ES) [M + H]+ |
|---|---|---|---|
| 64 | (2S)-2-methyl-1-[(2-methyl-3-pyridinyl)carbonyl]-4-({4-[(trifluoromethyl)oxy]phenyl}sulfonyl)piperazine | 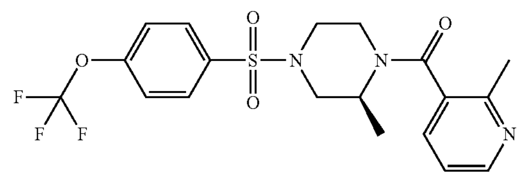 | 444 |
| 65 | (2R)-2-methyl-1-[(2-methyl-3-pyridinyl)carbonyl]-4-({4-[(trifluoromethyl)oxy]phenyl}sulfonyl)piperazine | 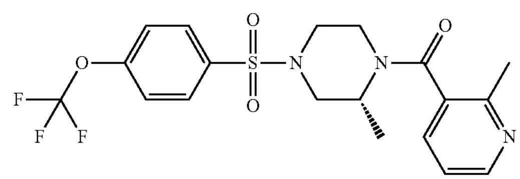 | 444 |
| 66 | 5-[(4-{[4-(trifluoromethyl)phenyl]sulfonyl}-1-piperazinyl)carbonyl]-2-pyridinamine | 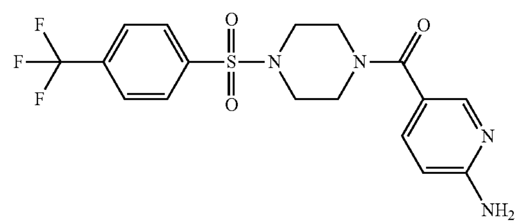 | 415 |
| 67 | 4-({(3S)-4-[(2,6-dimethyl-3-pyridinyl)carbonyl]-3-methyl-1-piperazinyl}sulfonyl)-3-methylbenzonitrile | 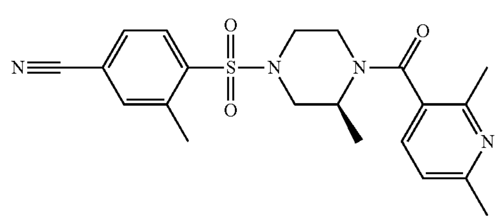 | 413 |
| 68 | 4-({(3S)-4-[(4,6-dimethyl-3-pyridinyl)carbonyl]-3-methyl-1-piperazinyl}sulfonyl)-3-methylbenzonitrile | 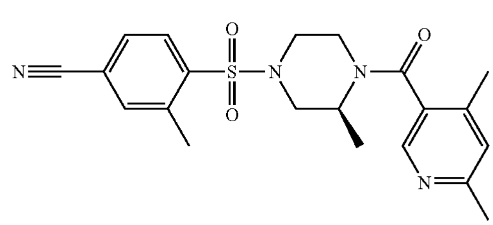 | 413 |

Examples 69 to 71

The compounds of Table 2 were prepared in a similar manner as the compounds of Example 56 and 57 using the corresponding reactants.

TABLE 2

| Example no. | Name | Structure | m/z (API-ES) [M + H]$^+$ |
|---|---|---|---|
| 69 | 1-{[6-(1-pyrrolidinyl)-3-pyridinyl]carbonyl}-4-{[4-(trifluoromethyl)phenyl]sulfonyl} piperazine | 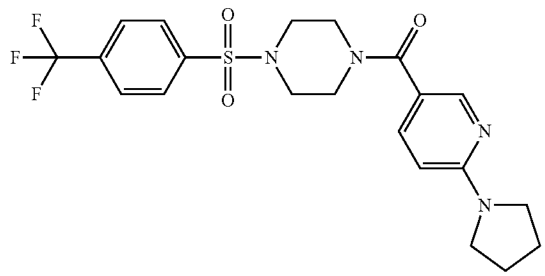 | 469 |
| 70 | N-(tetrahydro-2H-pyran-4-yl)-5-[(4-{[4-(trifluoromethyl)phenyl]sulfonyl}-1-piperazinyl)carbonyl]-2-pyridinamine | 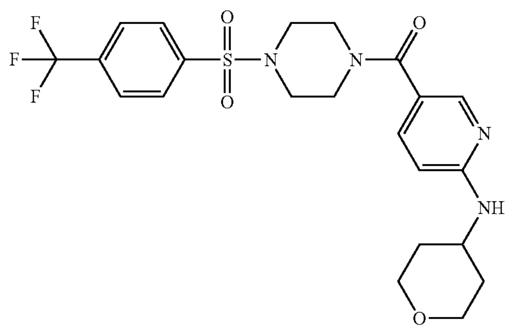 | 499 |
| 71 | 4-[((3S)-4-{[6-(dimethylamino)-3-pyridinyl]carbonyl}-3-methyl-1-piperazinyl)sulfonyl]-3-methylbenzonitrile | 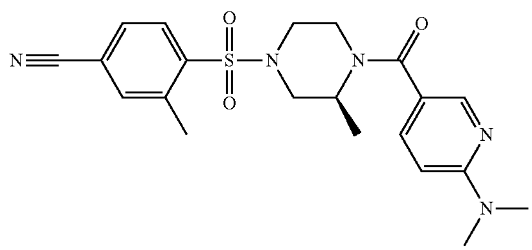 | 428 |

Examples 72 and 73

The compounds of Table 3 were prepared in a similar manner as the compound of Example 22 using the corresponding reactants.

TABLE 3

| Example no. | Name | Structure | m/z (API-ES) [M + H]$^+$ |
|---|---|---|---|
| 72 | 4-({(3S)-3-methyl-4-[(6-methyl-3-pyridinyl)carbonyl]-1-piperazinyl}sulfonyl) benzonitrile | 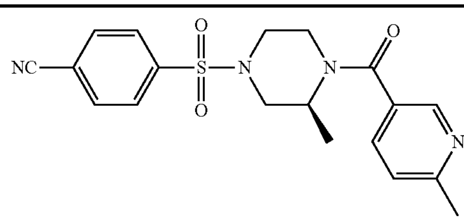 | 385 |

TABLE 3-continued

| Example no. | Name | Structure | m/z (API-ES) [M + H]+ |
|---|---|---|---|
| 73 | 1-({4-[(difluoromethyl)oxy]phenyl}sulfonyl)-4-[(6-methyl-3-pyridinyl)carbonyl]piperazine | 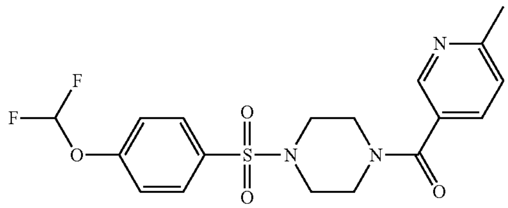 | 412 |

Example 74

1-[(6-methyl-3-pyridinyl)carbonyl]-4-{[2-methyl-4-(trifluoromethyl)phenyl]sulfonyl}piperazine

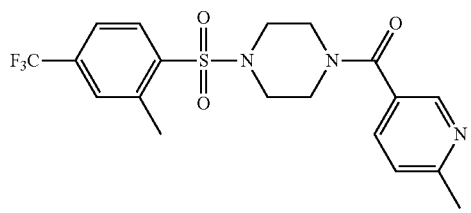

The compound of Example 74 was prepared in a similar manner as the compound of Example 49 using the corresponding reactants.

m/z (API-ES) 428 [M+H]+

Example 75

(2S)-1-{[6-(1-Azetidinyl)-4-methyl-3-pyridinyl]carbonyl}-2-methyl-4-{[4-(trifluoromethyl)phenyl]sulfonyl}piperazine

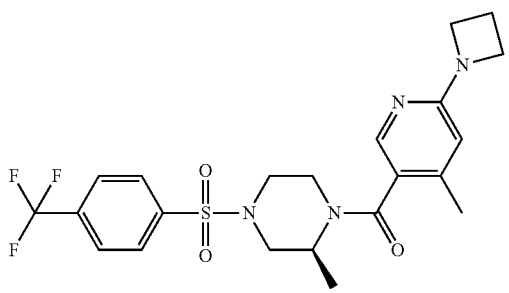

(2S)-1-[(6-Fluoro-4-methyl-3-pyridinyl)carbonyl]-2-methyl-4-{[4-(trifluoromethyl)phenyl]sulfonyl}piperazine (may be prepared as described in Example 27) (67 mg, 0.15 mmol) was weighed into a microwave vial and dissolved in isopropanol (1.5 ml). Azetidine (0.203 ml, 3.01 mmol) was added and the mixture was heated in the microwave to 120° C. for 12 h with stirring. The reaction mixture was concentrated to give the crude material as a colourless gum (~187 mg). This was purified by MDAP to give the title compound as a pale yellow gum (67 mg). The gum was redissolved in MeOH, water was added, and the mixture was concentrated under a flow of argon then dried in vacuo to give the title compound as a colourless solid.

m/z (API-ES) 483 [M+H]+

$^1$H NMR (400 MHz, CHLOROFORM-d) δ ppm 1.32-1.45 (m, 3 H), 2.16 (s, 3 H), 2.24-2.35 (m, 1 H), 2.36-2.53 (m, 3 H), 3.26-3.41 (m, 1 H), 3.55-3.67 (m, 1 H), 3.70-3.83 (m, 1 H), 4.04 (t, J=7.5 Hz, 4 H), 4.0-4.5 (v br, 1 H), 4.6-5.1 (v br, 1 H), 6.05 (s, 1 H), 7.77-7.90 (m, 5 H).

Example 76

4-({(3S)-4-[(6-cyclopropyl-3-pyridinyl)carbonyl]-3-methyl-1-piperazinyl}sulfonyl)-3-methylbenzonitrile

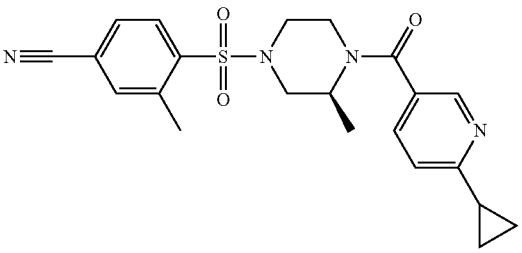

Argon was bubbled through a solution of 4-({(3S)-4-[(6-iodo-3-pyridinyl)carbonyl]-3-methyl-1-piperazinyl}sulfonyl)-3-methylbenzonitrile (50.0 mg, 0.098 mmol) (may be prepared as described in Example 50), potassium phosphate (72.8 mg, 0.343 mmol) and cyclopropylboronic acid (25.2 mg, 0.294 mmol) in toluene (3 mL) and water (200 μl) for 30 min. Tricyclohexylphosphine (2.75 mg, 9.80 μmol) and palladium(II) acetate (1.100 mg, 4.90 μmol) were added and the resulting pale yellow solution heated at 100° C. for 2 h. LCMS had not changed from 1 min, at 45° C. The solution was cooled and concentrated under vacuum to leave a pale yellow solid. Purification by MDAP and concentration of the desired fractions gave the title compound (1.0 mg) as a clear film, and a batch of recovered 4-({(3S)-4-[(6-iodo-3-pyridinyl)carbonyl]-3-methyl-1-piperazinyl}sulfonyl)-3-methylbenzonitrile (28.2 mg) starting material.

m/z (API-ES) 425 [M+H]+

$^1$H NMR (400 MHz, CHLOROFORM-d) δ ppm 1.03-1.07 (m, 4H), 1.36 (d, J=7.2 Hz, 3H), 2.06 (m, 1H), 2.68 (s, 3H), 2.71 (td, J=12.0, 3.2 Hz, 1H), 2.89 (dd, J=12.0, 3.2 Hz, 1H), 3.35 (m, 1H), 3.58 (m, 1H), 3.73 (m, 1H), 4.12 (brm, 1H), 4.53 (brm, 1H), 7.19 (d, J=8.4 Hz,1H), 7.56 (dd, J=8.4, 2.4 Hz,1H), 7.60-7.67 (m, 2H), 7.95 (d, J=8.4 Hz, 1H), 8.42 (d, J=2.4 Hz, 1H)

Equipment:
Mass-Directed Automated HPLC/Mass-Directed Automated Preparation (MDAP)

Where indicated in the above compounds, purification by mass-directed automated HPLC was carried out using the following apparatus and conditions:

Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
Waters MassLynx version 4 SP2
Column The columns used are Waters Atlantis, the dimensions of which are 19 mm×100 mm (small scale) and 30 mm×100 mm (large scale). The stationary phase particle size is 5 µm.

Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods There are five methods used depending on the analytical retention time of the compound of interest. They have a 13.5-minute runtime, which comprises of a 10-minute gradient followed by a 3.5 minute column flush and re-equilibration step.

Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow Rate

All of the above methods have a flow rate of either 20 mls/min (Small Scale) or 40 mls/min (Large Scale).

Liquid Chromatography/Mass Spectrometry

Analysis of the above compounds by Liquid Chromatography/Mass Spectrometry (LC/MS) was carried out using the following apparatus and conditions:

Hardware
Waters Acquity Binary Solvent Manager
Waters Acquity Sample Manager
Waters Acquity PDA
Waters ZQ Mass Spectrometer
Sedere Sedex 75
Software
Waters MassLynx version 4.1
Column The column used is a Waters Acquity BEH UPLC C18, the dimensions of which are 2.1 mm×50 mm. The stationary phase particle size is 1.7 µm.

Solvents
A: Aqueous solvent=Water+0.05% Formic Acid
B: Organic solvent=Acetonitrile+0.05% Formic Acid
Weak Wash=1:1 Methanol:Water
Strong Wash=Water Method The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40° C.
The UV detection range is from 220 to 330 nm Biotage SP4®

Biotage-SP4® is an automated purification system. It uses preloaded silica gel columns. The user applies their material to the top of the column and chooses solvents, gradients, flow rates, column size, collection method and eluting volumes.

Phase Separators (Hydrophobic Frit)

Phase separators are a range of ISOLUTE® columns fitted with an optimized frit material that easily separates aqueous phase from chlorinated solvents under gravity.

SCX—Strong Cation Exchange Cartridge

Where indicated in the compounds, an SCX cartridge was used as part of the compound purification process. Typically an ISOLUTE SCX-2 cartridge was used. ISOLUTE SCX-2 is a silica-based sorbent with a chemically bonded propylsulfonic acid functional group.

ISOLUTE SCX-2 Chemical Data
Base Material: Silica, 50 µm
Functional Group: Propylsulfonic acid
Capacity: 0.6 meq/g
Counter Ion: Proton Pharmacological Data Compounds of the invention may be tested for in vitro biological activity in the hCa$_v$2.2 assay in accordance with the following studies:

Methods
Cell Biology

Stable cell lines expressing the human Ca$_v$2.2 α ($\alpha 1_B$) subunit, along with the human β3 and α2δ1 auxiliary subunits were created following sequential transfection and selection of human embryonic kidney (HEK293) cells. HEK293 cells were cultured in Dulbecco's modified Eagles media/F12 media (Invitrogen, Cat #041-95750V) containing 10% foetal bovine serum, with added L-glutamine (2 mM; Invitrogen, Cat #25030-024) and non-essential amino acids (5%; Invitrogen, Cat #11140-035). Initially HEK293 cells were transfected with two plasmid vectors for expression of the hCa$_v$2.2 α subunit (pCIN5-hCa$_v$2.2 which carries a neomycin resistance marker) and the hCa$_v$ β3 subunit (pCIH-hCa$_v$ β3 which carries a hygromycin resistance marker). Clonal cell lines were isolated following selection in media supplemented with 0.4 mg ml$^{-1}$ Geneticin G418 (Invitrogen, Cat #10131-027) and 0.1 mg ml$^{-1}$ hygromycin (Invitrogen, Cat #10687-010). These clonal cell lines were assessed for Ca$_v$2.2 α/β3-mediated current expression using the IonWorks planar array electrophysiology technology (described below). A clonal line was identified that gave a reasonable level of functional Ca$_v$2.2 α/β3 current expression. This cell line was transfected with a plasmid vector for expression of the human α2δ1 subunit (pCIP-α2δ1 which carries a puromycin resistance marker) and clonal cell lines isolated following selection in media containing 0.62 µg ml$^{-1}$ puromycin (Sigma, Cat

P-7255), in addition to 0.4 mg ml$^{-1}$ Geneticin G418 and 0.1 mg ml$^{-1}$ hygromycin. Several cell lines were identified that gave robust levels of Ca$_v$2.2 α/β3/α2δ1-mediated current expression and one of these was selected for compound profiling. Expression of all three subunits within this cell line was continuously maintained by the inclusion of G418 (0.4 mg ml$^{-1}$), hygromycin (0.1 mg ml$^{-1}$) and puromycin (0.62 μg ml$^{-1}$). Cells were maintained at 37° C. in a humidified environment containing 5% CO$_2$ in air. Cells were liberated from the T175 culture flasks for passage and harvesting using TrpLE (Invitrogen, Cat #12604-013).

Cell Preparation

Cells were grown to 30-60% confluence in T175 flasks and maintained at 30° C. for 24 hrs prior to recording. Cells were lifted by removing the growth media, washing with Ca$^{2+}$ free PBS (Invitrogen, Cat #14190-094) and incubating with 3 ml of warmed (37° C.) TrpLE (Invitrogen, Cat #12604-013) for 6 minutes. Lifted cells were suspended in 10 ml of extracellular buffer. Cell suspension was then placed into a 15 ml tube and centrifuged for 2 minutes at 700 rpm. After centrifugation, the supernatant was removed and the cell pellet was resuspended in 4.5 ml of extracellular solution.

Electrophysiology

Currents were recorded at room temperature (21-23° C.) using the IonWorks planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential ($V_H$) of −90 mV to +10 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 120, KCl 20 mM, MgCl$_2$ 5, EGTA 5, HEPES 10, adjusted to pH 7.3. Amphotericin was prepared as 30 mg/ml stock solution and diluted to a final working concentration of 0.2 mg ml$^{-1}$ in intracellular buffer solution. The extracellular solution contained the following (in mM): Na-gluconate 120, NaCl 20, MgCl$_2$ 1, HEPES 10, BaCl$_2$ 5, adjusted to pH 7.4.

Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using seal resistance (>40 MΩ), resistance reduction (>35%) and peak current amplitude (>200 pA) in the absence of compound to eliminate unsuitable cells from further analysis. Paired comparisons between pre-compound and post-compound additions were used to determine the inhibitory effect of each compound. The concentrations of compounds required to inhibit current elicited by the 1$^{st}$ depolarising pulse by 50% (tonic pIC50) were determined by fitting of the Hill equation to the concentration response data. In addition the use-dependent inhibitory properties of the compounds were determined by assessing the effect of compounds on the 10$^{th}$ versus 1$^{st}$ depolarising pulse. The ratio of the 10$^{th}$ over 1$^{st}$ pulse was determined in the absence and presence of drug and the % use-dependent inhibition calculated. The data was fitted using the same equation as for the tonic pIC$_{50}$ and the concentration producing 30% inhibition (use-dependent pUD$_{30}$) determined.

The compounds of Examples 1 to 49 and 52 to 74 were tested in the hCa$_v$2.2 assay and demonstrated the following pUD$_{30}$ and pIC$_{50}$ values. Compounds were tested in the form as described in the Examples. All compounds tested have been tested one or more times (up to 11 times). Variations in pUD$_{30}$ and pIC$_{50}$ values may arise between tests.

The compounds 1 to 49 and 52 to 74 exhibited a pUD$_{30}$ value of 4.5 or more than 4.5. The compounds 1 to 4, 6, 7, 9, 11 to 19, 21 to 25, 28 to 49, 53 to 57, 59, 61, 63, 65 to 69, 71 and 74 exhibited a pUD$_{30}$ value of 5.0 or more than 5.0. The compounds 1, 6, 7, 14, 21, 24, 25, 28, 30 to 34, 36, 37, 39 to 41, 43 to 49, 54 to 57, 61, 69, 71 and 74 exhibited a pUD$_{30}$ value of 5.5 or more than 5.5.

The compounds 1 to 25, 28 to 30, 34, 35, 38 to 42, 44, 45, 47, 52 to 53, 56 to 74 exhibited a mean pIC$_{50}$ value of 5.0 or less than 5.0. The compounds 1 to 23, 38 to 40, 52, 53, 57 to 59, 61 to 74 exhibited a mean pIC$_{50}$ value of 4.5 or less than 4.5.

The invention claimed is:

1. A method for the treatment of pain in a human in need thereof comprising administering to said human a therapeutically effective amount of a compound of formula (I), or a pharmaceutically acceptable salt thereof, wherein:

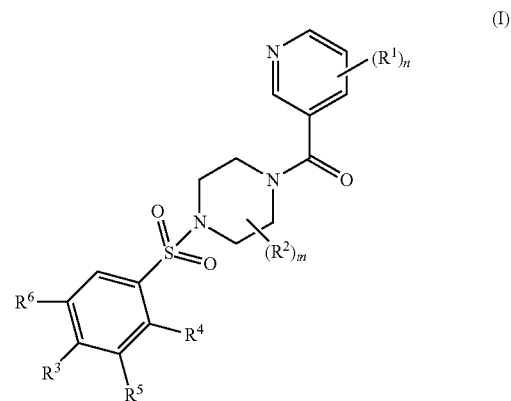

m and n are independently selected from 0, 1 and 2;

where present, each R$^1$ is independently selected from C$_{1-4}$ alkyl, C$_{1-4}$ alkoxy, C$_{3-6}$ cycloalkyl, cyano, NR$^{1a}$R$^{1b}$ and halogen;

R$^{1a}$ and R$^{1b}$ are independently selected from hydrogen, C$_{1-4}$ alkyl, C$_{3-6}$ cycloalkyl and a 4 to 6 membered heterocyclyl; or R$^{1a}$ and R$^{1b}$ together with the nitrogen atom to which they are attached form a 4 to 6 membered heterocyclic ring;

where present, each R$^2$ is C$_{1-4}$ alkyl;

R$^3$ is hydrogen, halogen, cyano, C$_{1-4}$ haloalkyl or C$_{1-4}$ haloalkoxy;

$R^4$ is hydrogen or $C_{1-4}$ alkyl;

$R^5$ is hydrogen, halogen, cyano, $C_{1-4}$ haloalkyl or $C_{1-4}$ haloalkoxy;

$R^6$ is hydrogen, halogen, cyano, $C_{1-4}$ haloalkyl or $C_{1-4}$ haloalkoxy;

such that at least 1 of $R^3$, $R^4$, $R^5$ and $R^6$ is a group other than hydrogen.

2. The method according to claim 1 wherein $R^1$ is selected from $C_{1-4}$ alkyl, $C_{1-4}$ alkoxy, cyano and $NR^{1a}R^{1b}$.

3. The method according to claim 2 wherein $R^1$ is selected from $C_{1-4}$ alkyl and $C_{1-4}$ alkoxy.

4. The method according to claim 3 wherein $R^1$ is selected from methyl and methoxy.

5. The method according to claim 4 wherein $R^1$ is selected from 2-methyl, 6-methyl, 2-methoxy and 6-methoxy.

6. The method according to claim 5 wherein $R^1$ is 2-methyl.

7. The method according to claim 1 wherein $R^1$ is $NR^{1a}R^{1b}$ and $R^{1a}$ and $R^{1b}$ are independently selected from hydrogen and $C_{1-4}$ alkyl, or $R^{1a}$ and $R^{1b}$ together with the nitrogen atom to which they are attached form a 4 to 6 membered heterocyclic ring.

8. The method according to claim 7 wherein $R^{1a}$ and $R^{1b}$ are $C_{1-4}$ alkyl, or $R^{1a}$ and $R^{1b}$ together with the nitrogen atom to which they are attached form a 4 or 5 membered heterocyclic ring.

9. The method according to claim 8 wherein $R^{1a}$ and $R^{1b}$ are $C_{1-4}$ alkyl, or $R^{1a}$ and $R^{1b}$ together with the nitrogen atom to which they are attached form a morpholinyl, pyrrolidinyl or azetidinyl ring.

10. The method according to claim 9 wherein $R^{1a}$ and $R^{1b}$ are $C_{1-4}$ alkyl.

11. The method according to claim 10 wherein $R^{1a}$ and $R^{1b}$ are selected from methyl and ethyl.

12. The method according to claim 1 wherein n is 0 or 1.

13. The method according to claim 12 wherein n is 1.

14. The method according to claim 1 wherein $R^2$ is methyl.

15. The method according to claim 14 wherein $R^2$ is methyl and m is 1.

16. The method according to claim 1 wherein the compound is a compound of formula (Ia)

(Ia)

or a pharmaceutically acceptable salt thereof.

17. The method according to claim 16 wherein the compound is a compound of formula (Ib)

(Ib)

or a pharmaceutically acceptable salt thereof.

18. The method according to claim 1 wherein $R^3$ is $C_{1-4}$ haloalkyl or $C_{1-4}$ haloalkoxy.

19. The method according to claim 18 wherein $R^3$ is trifluoromethyl, trifluoromethoxy or difluoromethoxy.

20. The method according to claim 1 wherein $R^4$ is hydrogen or methyl.

21. The method according to claim 20 wherein $R^4$ is hydrogen.

22. The method according to claim 1 wherein $R^5$ and $R^6$ are independently selected from hydrogen and $C_{1-4}$ haloalkyl.

23. The method according to claim 22 wherein $R^5$ and $R^6$ are independently selected from hydrogen and trifluoromethyl.

24. The method according to claim 23 wherein $R^5$ and $R^6$ are hydrogen.

25. The method according to claim 1, which is (2S)-2-Methyl-1-[(2-methyl-3-pyridinyl)carbonyl]-4-{[4-(trifluoromethyl)phenyl]sulfonyl}piperazine of formula or a pharmaceutically acceptable salt thereof.

26. A pharmaceutical composition comprising (a) a compound of formula (I), or a pharmaceutically acceptable salt thereof,
wherein:

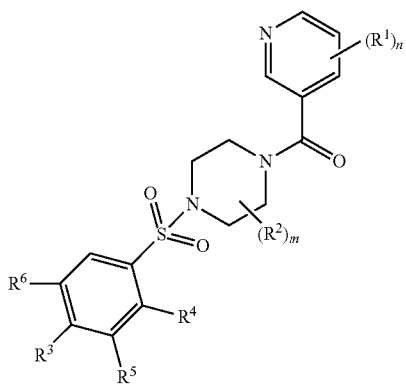

m and n are independently selected from 0, 1 and 2;
where present, each $R^1$ is independently selected from $C_{1-4}$ alkyl, $C_{1-4}$ alkoxy, $C_{3-6}$ cycloalkyl, cyano, $NR^{1a}R^{1b}$ and halogen;
$R^{1a}$ and $R^{1b}$ are independently selected from hydrogen, $C_{1-4}$ alkyl, $C_{3-6}$ cycloalkyl and a 4 to 6 membered heterocyclyl; or $R^{1a}$ and $R^{1b}$ together with the nitrogen atom to which they are attached form a 4 to 6 membered heterocyclic ring;
where present, each $R^2$ is $C_{1-4}$ alkyl;
$R^3$ is hydrogen, halogen, cyano, $C_{1-4}$ haloalkyl or $C_{1-4}$ haloalkoxy;
$R^4$ is hydrogen or $C_{1-4}$ alkyl;
$R^5$ is hydrogen, halogen, cyano, $C_{1-4}$ haloalkyl or $C_{1-4}$ haloalkoxy;
$R^6$ is hydrogen, halogen, cyano, $C_{1-4}$ haloalkyl or $C_{1-4}$ haloalkoxy;
such that at least 1 of $R^3$, $R^4$, $R^5$ and $R^6$ is a group other than hydrogen;
and (b) a pharmaceutically acceptable excipient.

27. A compound, (2S)-2-Methyl-1-[(2-methyl-3-pyridinyl)carbonyl]-4-{[4-(trifluoromethyl)phenyl]sulfonyl}piperazine of formula

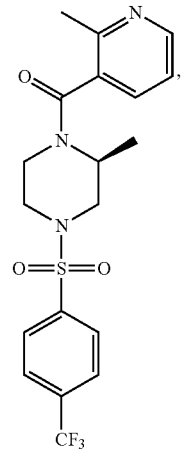

or a salt thereof.

* * * * *